US012797379B2

(12) United States Patent
Shibata et al.

(10) Patent No.: US 12,797,379 B2

(45) Date of Patent: Nov. 17, 2026

(54) THERAPEUTIC AGENT FOR BILE DUCT CANCER

(71) Applicants: NATIONAL CANCER CENTER, Tokyo (JP); Eisai R&D Management Co., Ltd., Tokyo (JP)

(72) Inventors: Tatsuhiro Shibata, Tokyo (JP); Yasuhito Arai, Tokyo (JP); Kenichi Nomoto, Andover, MA (US); Tomio Nakamura, Tokyo (JP); Akihiko Tsuruoka, Tokyo (JP); Saori Miyano, Tsukuba (JP)

(73) Assignees: National Cancer Center, Tokyo (JP); Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/547,139

(22) PCT Filed: Mar. 23, 2016

(86) PCT No.: PCT/JP2016/059162

§ 371 (c)(1),
(2) Date: Jul. 28, 2017

(87) PCT Pub. No.: WO2016/152907

PCT Pub. Date: Sep. 29, 2016

(65) Prior Publication Data

US 2018/0015079 A1 Jan. 18, 2018

Related U.S. Application Data

(60) Provisional application No. 62/138,058, filed on Mar. 25, 2015.

(51) Int. Cl.
*A61K 31/4545* (2006.01)
*A61P 1/16* (2006.01)
*A61P 35/00* (2006.01)

(52) U.S. Cl.
CPC ................................ *A61K 31/4545* (2013.01)

(58) Field of Classification Search
CPC .......................... C07D 401/14; A61K 31/4545
See application file for complete search history.

(56) References Cited

U.S. PATENT DOCUMENTS

| | | | |
|---|---|---|---|
| 6,831,175 B2 | 12/2004 | Li et al. | |
| 7,109,219 B2 | 9/2006 | Tsuruoka et al. | |
| 7,253,286 B2 | 8/2007 | Funahashi et al. | |
| 8,131,527 B1 | 3/2012 | Saxty et al. | |
| 8,614,216 B2 | 12/2013 | Okhamafe et al. | |
| 8,933,099 B2 * | 1/2015 | Funasaka | C07D 409/14 514/318 |
| 9,951,047 B2 | 4/2018 | Ozaki et al. | |
| 11,219,619 B2 | 1/2022 | Yamaguchi et al. | |
| 2004/0053908 A1 | 3/2004 | Funahashi et al. | |
| 2004/0122029 A1 | 6/2004 | Liu et al. | |
| 2004/0204427 A1 | 10/2004 | Chen et al. | |
| 2005/0187236 A1 | 8/2005 | Tsuruoka et al. | |
| 2005/0256154 A1 | 11/2005 | Luk et al. | |
| 2008/0108648 A1 | 5/2008 | Alcouffe et al. | |
| 2009/0069296 A1 | 3/2009 | Peglion et al. | |
| 2011/0060215 A1 | 3/2011 | Tupin et al. | |
| 2012/0270918 A1 | 10/2012 | Abecassis et al. | |
| 2013/0338134 A1 | 12/2013 | Wu et al. | |
| 2014/0142084 A1 | 5/2014 | Kameda et al. | |
| 2014/0155385 A1 | 6/2014 | Barf et al. | |
| 2014/0235614 A1 | 8/2014 | Funasaka et al. | |
| 2014/0378422 A1 | 12/2014 | Yovine et al. | |
| 2015/0191791 A1 | 7/2015 | Shibata | |
| 2016/0243228 A1 | 8/2016 | Holash et al. | |
| 2017/0145102 A1 | 5/2017 | Pierce et al. | |
| 2017/0145103 A1 | 5/2017 | Pierce et al. | |
| 2017/0217935 A1 | 8/2017 | Ozaki et al. | |
| 2018/0303817 A1 | 10/2018 | Miyano et al. | |
| 2020/0277387 A1 | 9/2020 | Currie | |
| 2020/0375970 A1 | 12/2020 | Yamaguchi et al. | |
| 2023/0052212 A1 | 2/2023 | Pierce et al. | |
| 2023/0149381 A1 | 5/2023 | Nishibata et al. | |

FOREIGN PATENT DOCUMENTS

| | | |
|---|---|---|
| AU | 2014219811 | 8/2014 |
| CA | 3091153 | 10/2019 |
| CL | 201400130 | 8/2014 |
| CN | 1678607 | 10/2005 |
| CN | 101024627 | 8/2007 |
| CN | 103917545 | 7/2014 |
| CN | 106660997 | 5/2017 |
| CN | 107205996 | 9/2017 |
| EP | 1415987 | 5/2004 |
| EP | 1522540 | 4/2005 |
| EP | 2657233 | 8/2014 |
| JP | 2008-533111 | 3/2006 |

(Continued)

OTHER PUBLICATIONS

European Search Report in European Application No. 15834302.0, dated Mar. 15, 2018, 6 pages.
Notice of Allowance in Gulf Cooperation Council Patent Application GCC/P/2014/26467, dated Jan. 7, 2018, 2 pages (English Translation).
Notice of Allowance in Russian Patent Application No. 2015134558, dated Jan. 10, 2018, 25 pages (English Translation).
Notice of Allowance in U.S. Appl. No. 15/500,429, dated Jan. 18, 2018, 6 pages.
Notice of Allowance in Ukraine Patent Application a201508149, dated Jan. 3, 2018, 16 pages. (English Translation).
Office Action in Israel Patent Application No. 240623, dated Dec. 20, 2017, 8 pages (English Translation).

(Continued)

*Primary Examiner* — Irina Neagu
(74) *Attorney, Agent, or Firm* — Fish & Richardson P.C.

(57) ABSTRACT

The present invention provides a therapeutic agent for bile duct cancer comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide or a pharmacologically acceptable salt thereof.

9 Claims, 7 Drawing Sheets

Specification includes a Sequence Listing.

(56) References Cited

FOREIGN PATENT DOCUMENTS

| | | | |
|---|---|---|---|
| JP | 2006-522756 | | 10/2006 |
| JP | 2009-108032 | A | 5/2009 |
| JP | 2009-215313 | | 9/2009 |
| JP | 5600229 | | 10/2014 |
| JP | 2014-237707 | | 12/2014 |
| JP | 2015-505562 | | 2/2015 |
| JP | 5925978 | | 4/2016 |
| JP | 2017-206437 | A | 11/2017 |
| JP | 2018-507220 | A | 3/2018 |
| JP | 2018-538274 | A | 12/2018 |
| KR | 10-2005-0059151 | | 6/2005 |
| KR | 10-2017-0035927 | | 3/2017 |
| KR | 102050128 | | 11/2019 |
| RU | 2257380 | | 7/2005 |
| RU | 2005108999 | | 8/2005 |
| RU | 2345077 | | 2/2006 |
| RU | 2310651 | | 11/2007 |
| TW | 200413353 | | 8/2004 |
| WO | WO 2002/032872 | | 4/2002 |
| WO | WO 2004/002410 | A2 | 1/2004 |
| WO | WO 2004/020434 | | 3/2004 |
| WO | WO 2006/000420 | | 1/2006 |
| WO | WO 2006/097625 | | 9/2006 |
| WO | WO 2007/071752 | | 6/2007 |
| WO | WO 2008/008747 | | 1/2008 |
| WO | WO 2008/012690 | | 1/2008 |
| WO | WO 2008/075068 | | 6/2008 |
| WO | WO 2008/078091 | | 7/2008 |
| WO | WO 2008/078100 | | 7/2008 |
| WO | WO 2009/001070 | | 12/2008 |
| WO | WO 2009/019518 | | 2/2009 |
| WO | WO 2009/047506 | | 4/2009 |
| WO | WO 2009/047522 | | 4/2009 |
| WO | WO 2009/056886 | | 5/2009 |
| WO | WO 2009/076602 | | 6/2009 |
| WO | WO 2009/117421 | A2 | 9/2009 |
| WO | WO 2009/141386 | | 11/2009 |
| WO | WO 2009/150240 | | 12/2009 |
| WO | WO 2009/153592 | | 12/2009 |
| WO | WO 2010/078421 | | 7/2010 |
| WO | WO 2010/078427 | | 7/2010 |
| WO | WO 2010/078430 | | 7/2010 |
| WO | WO 2010/119284 | | 10/2010 |
| WO | WO 2010/119285 | | 10/2010 |
| WO | WO 2011/001122 | | 1/2011 |
| WO | WO 2011/001413 | | 1/2011 |
| WO | WO 2011/016528 | | 2/2011 |
| WO | WO 2011/051425 | | 5/2011 |
| WO | WO 2011/071821 | | 6/2011 |
| WO | WO 2011/135376 | | 11/2011 |
| WO | WO 2012/004732 | | 1/2012 |
| WO | WO 2012/073017 | | 6/2012 |
| WO | WO 2012/088266 | | 6/2012 |
| WO | WO 2013/010380 | | 1/2013 |
| WO | WO 2013/061074 | | 5/2013 |
| WO | WO 2013/061077 | | 5/2013 |
| WO | WO 2013/061080 | | 5/2013 |
| WO | WO 2013/061081 | | 5/2013 |
| WO | WO 2013/087744 | | 6/2013 |
| WO | WO 2013/108809 | | 7/2013 |
| WO | WO 2013/116293 | | 8/2013 |
| WO | WO 2013/129369 | | 9/2013 |
| WO | WO 2013/151913 | | 10/2013 |
| WO | WO 2013/179034 | | 12/2013 |
| WO | WO 2014/007369 | | 1/2014 |
| WO | WO 2014/011900 | | 1/2014 |
| WO | WO 2014/026125 | | 2/2014 |
| WO | WO 2014/044846 | | 3/2014 |
| WO | WO 2014/048878 | | 3/2014 |
| WO | WO 2014/051022 | | 3/2014 |
| WO | WO 2014/129477 | | 8/2014 |
| WO | WO 2014/145751 | | 9/2014 |
| WO | WO 2014/162039 | | 10/2014 |
| WO | WO 2016/027781 | | 2/2016 |
| WO | WO 2016/084883 | | 6/2016 |
| WO | WO 2016/134234 | | 8/2016 |
| WO | WO 2016/152907 | | 9/2016 |
| WO | WO 2017/091577 | | 6/2017 |
| WO | WO 2017/104739 | | 6/2017 |
| WO | WO 2018/049233 | | 3/2018 |
| WO | WO 2019/189241 | | 10/2019 |
| WO | WO 2020/014440 | A1 | 1/2020 |
| WO | WO 2021/210636 | | 10/2021 |

OTHER PUBLICATIONS

Office Action in Russian Patent Application No. 2017103439, dated Feb. 6, 2018, 6 pages (English Translation).

Submission Document in Chilean Patent Application No. 2015-02311, dated Dec. 18, 2017, 40 pages (English Translation).

Submission Document in Jordan Patent Application No. 39/2014, dated Mar. 15, 2018, 12 pages (English Translation).

Submission Document in Russian Patent Application No. 2015134558, dated Nov. 22, 2017, 21 pages (English Translation).

Submission Document in Russian Patent Application No. 2017103439, dated Mar. 20, 2018, 19 pages (English Translation).

Submission Document in Taiwan Patent Application No. 103105419, dated Jan. 23, 2018, 30 pages (English Translation).

Submission Document in Thailand Patent Application No. 1501004679, dated Nov. 20, 2017, 6 pages (English Translation).

Notice of Allowance in U.S. Appl. No. 15/500,429, dated Oct. 19, 2017, 11 pages.

Notice of Allowance in Vietnam Patent Application No. 1-2015-02994, dated Oct. 23, 2017, 2 pages (English Translation).

Office Action in Australian Patent Application No. 2014219811, dated Jun. 16, 2017, 2 pages.

Office Action in Chilean Patent Application No. 2015-02311, dated Mar. 22, 2017, 21 pages (English Translation).

Office Action in Chilean Patent Application No. 2015-02311, dated Sep. 13, 2017, 13 pages (English Translation).

Office Action in Gulf Cooperation Council Patent Application No. GCC/P/2014/26467, dated Jun. 7, 2017, 7 pages (English Translation).

Office Action in Russian Patent Application No. 2015134558, dated Oct. 21, 2015, 3 pages (English Translation).

Office Action in Thai Patent Application No. 1501004679, dated Sep. 26, 2017, 4 pages (English Translation).

Office Action in Taiwan Patent Application No. 103105419, dated Oct. 24, 2017, 7 pages (English Translation).

Office Action in Ukraine Patent Application No. a201508149, dated Oct. 6, 2015, 2 pages (English Translation).

Office Action in Vietnam Patent Application No. 1-2015-02994, dated Jun. 21, 2017, 2 pages (English Translation).

Office Action in Vietnam Patent Application No. 1-2015-02994, dated Sep. 30, 2015, 4 pages (English Translation).

Response in Malaysia Patent Application No. PI2015702696, dated Nov. 6, 2017, 8 pages (English Translation).

Submission Document in Ukraine Patent Application No. a201508149, dated Nov. 20, 2017, 20 pages (English Translation).

"Cancer classification, NCI, from internet", 2008, p. 1-p. 3.

Applicant's unpublished experimental data, 2014, 1 page.

Arai et. al, "Fibroblast Growth Factor Receptor 2 Tyrosine Kinase Fusions Define a Unique Molecular Subtype of Cholangiocarcinoma", Hepatology, 2014, vol. 59, No. 4, p. 1427-p. 1434.

Bono et al., "Inhibition of Tumor Angiogenesis and Growth by a Small-Molecule Multi-FGF Receptor Blocker with Allosteric Properties", Cancer Cell, 2013, p. 477-p. 488.

Borad et al., "Integrated Genomic Characterization Reveals Novel, Therapeutically Relevant Drug Targets in FGFR and EGFR Pathways in Sporadic Intrahepatic Cholangiocarcinoma", PLOS Genetics, 2014, vol. 10, Issue 2, p. 1-p. 21.

Bucci et al., "channels contribute", Nature.chem.bio., Jun. 2013.

Cancer Genome Atlas Research Network, "Comprehensive genomic characterization of squamous cell lung cancers," Nature, 2012, 489(7417):519-525.

(56) References Cited

OTHER PUBLICATIONS

Celina Ang, "Role of the fibroblast growth factor receptor axis incholangiocarcinoma", Journal of Gastroenterology and Hepatology, 2015, vol. 30, p. 1116-p. 1122.
Chen et al., "Inhibition of endogenous SPARC enhances pancreatic-cancer cell growth: modulation by FGFR1-III isoform expression", Br J Cancer, 2010(102), p. 188-p. 195.
Daniele et al., "FGF Receptor Inhibitors: Role in Cancer Therapy", Curr Oncol Rep., 2012(14), p. 111-p. 119.
European Search Report in European Application No. 14754294.8, dated Jul. 15, 2016, 5 pages.
French et al., "Targeting FGFR4 Inhibits Hepatocellular Carcinoma in Preclinical Mouse Models", PLoS One, 2012(7), p. 1-p. 12.
Gavine et al., "AZD4547:An Orally Bioavailable, Potent, and Selective Inhibitor of the Fibroblast Growth Factor Receptor Tyrosine Kinase Family", Cancer Res, 2012(72), p. 2045-p. 2056.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", J Med Chem, 2011(54).
Guagnano et al., "FGFR Genetic Alterations Predict for Sensitivity to NVP-BGJ398, a Selective Pan-FGFR Inhibitor", Cancer Discovery, Sep. 20, 2012, p. 1118-p. 1133.
Harbinski et al., "Rescue Screens with Secreted Proteins Reveal Compensatory Potential of Receptor Tyrosine Kinases in Driving Cancer Growth", Cancer Discovery, Aug. 8, 2012, p. 948-p. 958.
International Preliminary Report on Patentability in International Application No. PCT/JP2014/053819, dated Sep. 3, 2015, 7 pages.
International Search Report in International Application No. PCT/JP2016/059162, dated May 24, 2016, 2 pages (English Translation).
Ishiwata et al., "Enhanced Expression of Fibroblast Growth Factor Receptor 2 IIIc Promotes Human Pancreatic Cancer Cell Proliferation", Am J Pathol, 2012(180), p. 1928-p. 1941.
Li et al., "Preparation of heteroaryls for therapeutic use in pharmaceutical compositions as kinase inhibitors for treatment of hyperproliferative diseases, including cancer, CA139:323437", Abbott Laboratories, USA, 2003.
Logie et al., "Activating mutations of the tyrosine kinase receptor FGFR3 are associated with benign skin tumors in mice and humans", Hum Mol Genet, 2005(14), p. 1153-p. 1160.
Mohammadiet al., "Crystal structure of an angiogenesis inhibitor bound to the FGF receptor tyrosine kinase domain", The EMBO Journal vol. 17 No. 20, 1998, p. 5896-p. 5904.
Nicholas et al., "Fibroblast growth factor signalling: from development to cancer", Nature Reviews Cancer, 2010(10), p. 116-p. 129.
Norman et al., "Protein—Ligand Crystal Structures Can Guide the Design of Selective Inhibitors of the FGFR Tyrosine Kinase", Journal of Medicinal Chemistry, May 21, 2012, p. 5003-p. 5012.
Notice of Allowance in U.S. Appl. No. 14/183,864, dated Nov. 19, 2014, 11 pages.
Office Action in Chinese Application No. 201480009370.X, dated May 26, 2016, 7 pages.
Office Action in U.S. Appl. No. 14/183,864, dated Jun. 4, 2014, 7 pages.
Office Action in U.S. Appl. No. 14/183,864, dated Sep. 16, 2014.
Patani et al., "Bioisosterism: A Rational Approach in Drug Design", Chemical—Reviews, vol. 96, No. 8, 1996, p. 3147-p. 3176.
Rubini et al., "Synthesis of Isosteric Methylene-Oxy Pseudodipeptide Analogues as Novel Amide Bond Surrogate Units", Tetrahedron, vol. 42, No. 21, 1986, p. 6039-p. 6045.
Sasaki et al., "Increased FGFR1 copy number in lung squamous cell carcinomas", Mol Med Report, 2012(5), p. 725-p. 728.
Shibata, "Clinical significance of Expression oFGFR2 Fusion Genes in Bile Duct Cancer", The Bilialy Tract & Pancreas, Feb. 12, 2015, vol. 36(2), p. 137-p. 142.
St. Bernard et al., "Fibroblast Growth Factor Receptors as Molecular Targets in Thyroid Carcinoma", Endocrinology, 2005(146), p. 1145-p. 1153.
Tsimafeyeu et al., "Overexpression of fibroblast growth factor receptors FGFR1 and FGFR2 in renal cell carcinoma", Scand J Urol Nephrol, 2011(45), p. 190-p. 195.
Weiss et al., "Frequent and Focal FGFR1 Amplification Associates with Therapeutically Tractable FGFR1 Dependency in Squamous Cell Lung Cancer", Sci Transl Med, Apr. 18, 2012, p. 1-p. 7.
Wesche et al., "Fibroblast growth factors and their receptors in cancer", Biochem J., 2011(437), p. 199-p. 213.
Zhang et al., "Translating the Therapeutic Potential of AZD4547 in FGFR1-Amplified Non-Small Cell Lung Cancer through the Use of Patient-Derived Tumor Xenograft Models", Clinical Cancer Research, May 24, 2013, p. 6657-p. 6667.
International Preliminary Report on Patentability in International Application No PCT/JP2015/073047, dated Mar. 2, 2017, 6 pages (English Translation).
International Preliminary Report on Patentability in Patent Application No. PCT/JP2016/059162, dated Oct. 5, 2017, 8 pages (English Translation).
International Search Report for PCT/JP2015/073047 dated Nov. 17, 2015 (English translation).
International Search Report in International Application No. PCT/JP2014/053819, dated Apr. 15, 2014, 9 pages.
Notice of Allowance in Australian Patent Application No. 2014219811, dated Sep. 13, 2017, 3 pages.
Notice of Allowance in Chinese Patent Application No. 201480009370.X dated Jul. 25, 2017, 4 pages (English Translation).
Notice of Allowance in European Patent Application No. 14754294.8, dated Jan. 4, 2017, 239 pages.
Notice of Allowance in European Patent Application No. 14754294.8, dated Mar. 9, 2017, 2 pages.
Notice of Allowance in Japanese Patent Application No. P2015-560425, dated Apr. 19, 2016, 6 pages (English Translation).
Notice of Allowance in Singapore Patent Application No. 11201506488W, dated Sep. 20, 2017 (English Translation).
Notice of Allowance in Singapore Patent Application No. 11201700703X, dated Sep. 12, 2017, 5 pages (English Translation).
Notice of Allowance in South African Application No. 2015/05941, dated May 24, 2016, 6 pages.
Office Action in Chinese Application No. 201480009370.X, dated Jan. 9, 2017, 10 pages (English Translation).
Office Action in Israeli Application No. 240623, dated Jan. 19, 2016, 5 pages (English Translation).
Office Action in Japanese Application No. P2015-560425, dated Mar. 8, 2016, 4 pages (English Translation).
Office Action in Pakistan Application No. 94/2014, dated May 13, 2016, 2 pages.
Office Action in Russian Patent Application No. 2015134558, dated Aug. 24, 2017, 11 pages (English Translation).
Office Action in Singapore Patent Application No. 11201700703X, dated Jun. 8, 2017, 5 pages (English Translation).
Office Action in U.S. Appl. No. 15/500,429, dated Jul. 31, 2017, 8 pages.
Office Action in Ukraine Patent Application No. a201508149, dated Aug. 11, 2017, 6 pages (English Translation).
Request to Amend Application Before Grant in Singapore Patent Application No. 11201506488W, dated Aug. 3, 2017, 21 pages (English Translation).
Response in Gulf Cooperation Council Patent Application No. GCC/P/2014/26467, dated Aug. 27, 2017, 18 pages (English Translation).
Response in U.S. Appl. No. 15/500,429, dated Sep. 27, 2017, 6 pages.
Response in Vietnam Patent Application No. 1-2015-02994, dated Aug. 7, 2017, 2 pages (English Translation).
Submission Document in Egypt Patent Application No. PCT1285/2015, dated Aug. 19, 2015, 2 pages (English Translation).
Submission Document in Argentine Patent Application No. P140100495, dated Jan. 23, 2015, 7 pages (English Translation).
Submission Document in Australian Patent Application No. 2014219811, dated Aug. 22, 2017, 6 pages.
Submission Document in Brazil Patent Application No. BR112015019790-6, dated Dec. 22, 2015, 12 pages (English Translation).

(56) References Cited

OTHER PUBLICATIONS

Submission Document in Brazil Patent Application No. BR112015019790-6, dated Apr. 28, 2016, 19 pages (English Translation).
Submission Document in Chilean Patent Application No. 2015-02311, dated Jun. 13, 2017, 38 pages (English Translation).
Submission Document in Chilean Patent Application No. 2015-02311, dated Jan. 8, 2016, 8 pages.
Submission Document in Chinese Patent Application No. 201480009370.X, dated Feb. 25, 2016, 18 pages (English Translation).
Submission Document in Chinese Patent Application No. 201480009370.X, dated Oct. 10, 2016, 59 pages (English Translation).
Submission Document in Chinese Patent Application No. 201480009370.X, dated Mar. 21, 2017, 41 pages (English Translation).
Submission Document in European Patent Application No. 14754294.8, dated Nov. 10, 2016, 9 pages.
Submission Document in Indian Patent Application No. 4989/CHENP/2015, dated May 9, 2016, 7 pages (English Translation).
Submission Document in Indonesia Patent Application No. P-00201505035, dated Apr. 27, 2016, 10 pages (English Translation).
Submission Document in Indonesia Patent Application No. P-00201505035, dated Dec. 5, 2016, 3 pages.
Submission Document in Israeli Patent Application No. 240623, dated May 18, 2016, 3 pages (English Translation).
Submission Document in Japanese Patent Application No. 2014-526292, dated May 30, 2014, 14 pages (English Translation).
Submission Document in Japanese Patent Application No. P2015-560425, dated Mar. 24, 2016, 8 pages (English Translation).
Submission Document in Malaysian Patent Application No. PI 2015702696, dated Jan. 6, 2016, 207 pages.
Submission Document in Malaysian Patent Application No. PI 2015702696, dated Apr. 7, 2016, 4 pages.
Submission Document in New Zealand Patent Application No. 711101, dated Jan. 20, 2016, 5 pages.
Submission Document in New Zealand Patent Application No. 711101, dated Apr. 12, 2016, 9 pages.
Submission Document in Pakistan Patent Application No. 94/2014, dated Aug. 25, 2016, 14 pages.
Submission Document in Peru Patent Application No. 001748-2015, dated Dec. 21, 2015, 9 pages (English Translation).
Submission Document in Philippines Patent Application No. 1-2015-501813, dated Dec. 21, 2015, 3 pages (English Translation).
Submission Document in Philippines Patent Application No. 1-2015-501813, dated Apr. 4, 2016, 1 page (English Translation).
Submission Document in Russian Patent Application No. 2015134558, dated Apr. 22, 2016, 14 pages (English Translation).
Submission Document in Russian Patent Application No. 2015134558, dated Dec. 25, 2015, 16 pages.
Submission Document in Singapore Patent Application No. 11201506488W, dated Dec. 23, 2015, 5 pages.
Submission Document in Singapore Patent Application No. 11201700703X, dated Jul. 19, 2017, 16 pages (English Translation).
Submission Document in Ukraine Patent Application No. a201508149, dated Oct. 6, 2015, 4 pages (English Translation).
Submission Document in Vietnam Patent Application No. 1-2015-02994, dated May 25, 2016, 12 pages (English Translation).
Submission Document in Vietnam Patent Application No. 1-2015-02994, dated Oct. 28, 2015, 22 pages (English Translation).
Turner et al., "Fibroblast growth factor signaling: from development to cancer", Nature Reviews Cancer, 2010 vol. 10, p. 116-p. 129.
Andre et al., "Targeting FGFR with Dovitinib (TKI258): Preclinical and Clinical Data in Breast Cancer", Clinical Cancer Research, vol. 19, No. 13, Jul. 1, 2013, p. 3693-p. 3702.
Berrada et al., "Treatment of triple-negative metastatic breast cancer: toward individualized targeted treatments or chemosensitization?," Annals of Oncology, vol. 21, Supplement 7, 2010, p. vii30-p. vii35.
Dey et al., "Targeting Fibroblast Growth Factor Receptors Blocks PI3K/AKT Signaling, Induces Apoptosis, and Impairs Mammary Tumor Outgrowth and Metastasis," Cancer Research, vol. 70, No. 10, May 15, 2010, p. 4151-p. 4162.
Foulkes et al., "Triple-Negative Breast Cancer," The New England Journal of Medicine, Nov. 11, 2010, 363:1938-1948.
International Preliminary Report on Patentability in Patent Application No. PCT/JP2016/087349, dated Jun. 28, 2018, 9 pages (English Translation).
Koziczak et al., "Blocking of FGFR signaling inhibits breast cancer cell proliferation through downregulation of D-type cyclins", Oncogene, vol. 23, 2004, p. 3501-p. 3508.
Miyano et al., "E7090, a Novel Selective Inhibitor of Fibroblast Growth Factor Receptors, Displays Potent Antitumor Activity and Prolongs Survival in Preclinical Models," Molecular Cancer Therapeutics, vol. 15, No. 11, Nov. 2016, p. 2630-p. 2639.
Notice of Allowance in Russian Patent Application No. 2017103439, dated Apr. 10, 2018, 14 pages (English Translation).
Notice of Allowance in U.S. Appl. No. 15/500,429, dated Mar. 29, 2018, 4 pages.
Office Action in New Zealand Patent Application 711101, dated May 1, 2018, 2 pages.
Office Action in Pakistan Patent Application No. 94/2014, dated May 3, 2018, 2 pages (English Translation).
Office Action in Pakistan Patent Application No. 523/2016, dated May 3, 2018, 2 pages (English Translation).
Office Action in Thai Patent Application No. 1501004679, dated Jun. 11, 2018, 4 pages (English Translation).
Office Action in Taiwan Patent Application No. 103105419, dated May 14, 2018, 4 pages (English Translation).
Submission Document in Israeli Patent Application No. 240623, dated Apr. 16, 2018, 15 pages (English Translation).
Submission Document in Pakistan Patent Application No. 523/2016, dated Jun. 4, 2018, 1 page (English Translation).
Turner et al., "FGFRI Amplification Drives Endocrine Therapy Resistance and is a Therapeutic Target in Breast Cancer," Cancer Research, vol. 70, No. 5, Mar. 1, 2010, p. 2085-p. 2094.
Submission Document in U.S. Appl. No. 16/225,772, dated Dec. 19, 2018, 104 pages.
Submission Document in Israeli Patent Application No. 250290, dated Dec. 26, 2018, 4 pages.
European Search Report in European Application No. 16768810.0, dated Dec. 11, 2018, 7 pages.
European Search Report in European Application No. 16768810.0, dated Aug. 17, 2018, 7 pages.
Office Action in Chinese Patent Application No. 201580042132.3, dated Aug. 8, 2018, 11 pages (English Translation).
Office Action in Mexican Patent Application No. MX/a/2015/010698, dated Jun. 15, 2018, 9 pages (English Translation).
Submission Document in Mexican Patent Application No. MX/a/2015/010698, dated Aug. 2, 2018, 17 pages (English Translation).
Submission Document in New Zealand Patent Application No. 711101, dated Jul. 20, 2018, 6 pages.
Submission Document in Pakistani Patent Application No. 94/2014, dated Jul. 7, 2018, 4 pages.
Submission Document in Taiwanese Patent Application No. 103105419, dated Aug. 8, 2018, 19 pages (English Translation).
Submission Document in Thai Patent Application No. 1501004679, dated Jul. 20, 2018, 4 pages (English Translation).
Notice of Allowance in Mexican Patent Application No. MX/a/2015/010698, dated Nov. 8, 2018, 4 pages (English Translation).
Notice of Allowance in Taiwanese Application No. 103105419, dated Sep. 11, 2018, 5 pages (English Translation).
Office Action in Israeli Patent Application No. 253701, dated Oct. 17, 2018, 7 pages (with English Translation).
Office Action in Israeli Patent Application No. 250290, dated Sep. 2, 2018, 5 pages (English Translation).
Submission Document in Chinese Application No. 201580042132.3, dated Oct. 22, 2018, 15 pages (with English Translation).

(56) References Cited

OTHER PUBLICATIONS

Submission Document in Chinese Patent Application No. 201680068110.9, dated Oct. 8, 2018, 11 pages (English Translation).
Submission Document in European Patent Application No. 15834302.0, dated Oct. 2, 2018, 80 pages.
Office Action in Peruvian Patent Application No. 001748-2015, dated Apr. 19, 2019, 19 pages (with English Translation).
Submission Document in U.S. Appl. No. 15/771,193, dated May 14, 2019, 8 pages.
Notice of Allowance in Canadian Patent Application No. 2901585, dated Jun. 5, 2019, 1 page (with English Translation).
Office Action in Chinese Patent Application No. 201680007472.7, dated Jun. 14, 2019, 14 pages (with English Translation).
Submission Document in Peruvian Patent Application No. 001748-2015, dated Jul. 6, 2019, 6 pages (with English Translation).
Notice of Allowance in Jordanian Patent Application No. 39/2014, dated Apr. 16, 2018, 2 pages (with English Translation).
Notice of Allowance in New Zealand Patent Application No. 711101, dated Jul. 27, 2018, 1 page.
International Search Report in International Application No. PCT/JP2019/037690, dated Jan. 15, 2019, 7 pages.
Office Action in U.S. Appl. No. 15/771,193, dated Jun. 7, 2019, 44 pages.
Submission Document in Singaporean Patent Application No. 11201706143S, dated May 30, 2019, 13 pages.
Notice of Allowance in Chinese Patent Application No. 201580042132.3, dated Mar. 6, 2019, 4 pages (with English Translation).
Notice of Allowance in Israeli Patent Application No. 240623, dated Jan. 7, 2019, 7 pages (English Translation).
Notice of Allowance in Japanese Patent Application No. P2017-508383, dated Mar. 5, 2019, 6 pages (with English Translation).
Office Action in Australian Patent Application No. 2015304465, dated Jan. 21, 2019, 2 pages.
Office Action in Canadian Patent Application No. 2901585, dated Jan. 30, 2019, 3 pages.
Office Action in Indian Patent Application No. 4989/CHENP/2015, dated Jan. 31, 2019, 5 pages (with English Translation).
Office Action in Indonesian Patent Application No. P-00201505035, dated Feb. 1, 2019, 5 pages, (with English Translation).
Office Action in U.S. Appl. No. 15/771,193, dated Apr. 1, 2019, 5 pages.
Submission Document in Australian Patent Application No. 2015304465, dated Apr. 5, 2019, 16 pages.
Submission Document in Brazilian Patent Application No. BR1120170163926, dated Mar. 6, 2019, 16 pages (with English Translation).
Submission Document in Canadian Patent Application No. 2901585, dated Mar. 25, 2019, 42 pages.
Submission Document in European Patent Application No. 16768810.0, dated Feb. 11, 2019, 9 pages.
Submission Document in Indian Patent Application No. 4989/CHENP/2015, Apr. 15, 2019, 24 pages.
Submission Document in Israeli Patent Application No. 253701, dated Feb. 4, 2019, 8 pages (English Translation).
Submission Document in Japanese Patent Application No. P2017-508383, dated Feb. 8, 2019, 80 pages (English Translation).
Choi et al., "Molecular Targeted Therapy for Hepatocellular Carcinoma: Present Status and Future Directions," Biological and Pharmaceutical Bulletin, 2015, 38:986-991.
International Search Report in International Application No. PCT/JP2019/012971, dated May 14, 2019, 9 pages.
Notice of Allowance in Australian Patent Application No. 2015304465, dated Apr. 24, 2019, 3 pages.
Submission Document in Indonesian Patent Application No. P-00201505035, dated Apr. 26, 2019, 8 pages (with English Translation).
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Abstract).
Office Action in Israeli Patent Application No. 250290, dated Aug. 15, 2019, 8 pages (with English Translation).
Notice of Allowance in Indonesian Patent Application No. P-00201505035, dated Sep. 27, 2019, 4 pages (with English Translation).
Submission Document in U.S. Appl. No. 16/225,772, dated Sep. 30, 2019, 10 pages.
Office Action in Korean Patent Application No. 10-2015-7022252, dated Sep. 5, 2019, 11 pages (with English Translation).
Office Action in Sri Lankan Patent Application No. 18355, dated Aug. 19, 2019, 1 page.
European Search Report in European Application No. 16875716.9, dated Jul. 29, 2019, 9 pages.
Notice of Allowance in Taiwanese Application No. 107134522, dated Jul. 29, 2019, 7 pages (with English Translation).
Notice of Allowance in Taiwanese Application No. 107134526, dated Jul. 29, 2019, 7 pages (with English Translation).
Notice of Allowance in Taiwanese Application No. 107134529, dated Jul. 29, 2019, 7 pages (with English Translation).
Office Action in Indian Patent Application No. 201747003469, dated Aug. 2, 2019, 5 pages (with English Translation).
Office Action in Israeli Patent Application No. 258671, dated Aug. 4, 2019, 5 page (with English Translation).
Office Action in Mexican Patent Application No. MX/a/2017/001624, dated Jun. 25, 2019, 8 pages (with English Translation).
Office Action in Russian Patent Application No. 2017127135, dated Aug. 22, 2019, 16 pages (with English Translation).
Office Action in U.S. Appl. No. 16/225,722, dated Jul. 9, 2019, 33 pages.
Submission Document in Mexican Patent Application No. MX/a/2017/001624, dated Aug. 21, 2019, 11 pages (with English Translation).
Submission Document in Peruvian Patent Application No. 001748-2015, dated Jun. 21, 2019, 4 pages (with English Translation).
Submission Document in U.S. Appl. No. 15/771,193, dated Aug. 22, 2019, 9 pages.
Watanabe et al., "Abstract 770: E7090: A potent and selective FGFR inhibitor with activity in multiple FGFR-driven cancer models with distinct mechanisms of activation," Cancer Research, 2015, 75(Suppl. 15):1-4, XP002792860 (Abstract Only).
Office Action in U.S. Appl. No. 15/774,193, dated Oct. 16, 2019, 44 pages.
Submission Document in Chinese Patent Application No. 201680007472.7, dated Oct. 10, 2019, 16 pages (with English Translation).
Notice of Allowance in Korean Patent Application No. 10-2015-7022252, dated Nov. 11, 2019, 5 pages (with English Translation).
Notice of Allowance in Mexican Patent Application No. MX/a/2017/001624, dated Oct. 23, 2019, 5 pages (with English Translation).
Office Action in European Patent Application No. 15834302.0, dated Oct. 28, 2019, 4 pages.
Submission Document in Korean Patent Application No. 10-2015-7022252, dated Oct. 25, 2019, 43 pages (with English Translation).
Notice of Allowance in U.S. Appl. No. 16/225,772, dated Oct. 22, 2019, 19 pages.
Notice of Allowance in Chilean Patent Application No. 2015-02311, dated Dec. 12, 2019, 6 pages (with English Translation).
Notice of Allowance in U.S. Appl. No. 16/225,772, dated Dec. 16, 2019, 9 pages.
Office Action in Argentine Patent Application No. P140100495, dated Nov. 11, 2019, 4 pages (with English Translation).
Submission Document in Israeli Patent Application No. 250290, dated Nov. 28, 2019, 8 pages (with English Translation).
Submission Document in Israeli Patent Application No. 258671, dated Nov. 26, 2019, 4 pages (with English Translation).
Submission Document in Russian Patent Application No. 2017127135, dated Nov. 14, 2019, 21 pages (with English Translation).
Submission Document in Sri Lankan Patent Application No. 18355, dated Nov. 21, 2019, 3 pages.

(56) References Cited

OTHER PUBLICATIONS

Wu et al., "Identification of Targetable FGFR Gene Fusions in Diverse Cancers," Cancer Discovery, 2013 American Association for Cancer, Research Brief, 2013, 13 pages.
Notice of Allowance in U.S. Appl. No. 16/225,772, dated Jan. 15, 2020, 9 pages.
Submission Document in Brazilian Patent Application No. BR112015019790-6, dated Dec. 30, 2019, 16 pages (with English Translation).
Submission Document in Indian Patent Application No. 201747003469, dated Jan. 13, 2020, 12 pages.
Notice of Allowance in Pakistani Patent Application No. 94/2014, dated Dec. 31, 2019, 3 pages.
Notice of Allowance in Pakistani Patent Application No. 523/2016, dated Dec. 31, 2019, 3 pages.
Submission Document in Argentine Patent Application No. P140100495, dated Dec. 17, 2019, 7 pages (with English Translation).
Office Action in Chinese Patent Application No. 201680007472.7, dated Jan. 15, 2020, 8 pages (with English Translation).
Notice of Allowance in Russian Patent Application No. 2017127135, dated Dec. 17, 2019, 16 pages (with English Translation).
Office Action in Israeli Patent Application No. 253701, dated Nov. 28, 2019, 7 pages (with English Translation).
Submission Document in U.S. Appl. No. 15/771,193, dated Jan. 16, 2020, 20 pages.
Office Action in Israeli Patent Application No. 250290, dated Jan. 29, 2020, 10 pages (with English Translation).
Official Notification in Brazilian Patent Application No. BR112015019790-6, dated Jan. 21, 2020, 2 pages (with English Translation).
Submission Document in Israeli Patent Application No. 253701, dated Feb. 5, 2020, 7 pages (with English Translation).
Gould, "Salt selection for basic drugs," International Journal of Pharmaceutics, 1986, 33:201-217.
Office Action in Indian Patent Application No. 201747027065, dated Jan. 28, 2020, 6 pages (with English Translation).
Office Action in Russian Patent Application No. 2018119102, dated Feb. 4, 2020, 12 pages (with English Translation).
Office Action in U.S. Appl. No. 15/771,193, dated Mar. 24, 2020, 12 pages.
Submission Document in Chinese Patent Application No. 201680007472.7, dated Mar. 19, 2020, 8 pages (with English Translation).
Submission Document in European Patent Application No. 15834302.0, dated Feb. 19, 2020, 74 pages.
Notice of Allowance in European Patent Application No. 16875716.9, dated Oct. 28, 2020, 18 pages.
Notice of Allowance in Singaporean Patent Application No. 11201706143S, dated Oct. 29, 2020, 4 pages.
Submission Document in Indian Patent Application No. 201847015401, dated Oct. 29, 2020, 20 pages.
Submission Document in Israeli Patent Application No. 258671, dated Sep. 30, 2020, 35 pages (with English Translation).
Submission Document in Mexican Patent Application No. MX/a/2018/006329, dated Oct. 8, 2020, 7 pages (with English Translation).
Notice of Allowance in Brazilian Patent Application No. BR112015019790-6, dated Aug. 11, 2020, 2 pages (with English Translation).
Submission Document in Indian Patent Application No. 201747027065, dated Aug. 18, 2020, 6 pages.
International Search Report and Written Opinion in International Application No. PCT/JP2019/012971, dated May 14, 2019, 11 pages (with Partial Translation).
International Search Report in International Application No. PCT/JP2018/037690, dated Jan. 15, 2019, 7 pages.
Kim et al., "Regorafenib in advanced hepatocellular carcinoma (HCC): considerations for treatment," Cancer Chemotherapy and Pharmacology, 2017, 80:945-954.
Llovet et al., "Sorafenib in Advanced Hepatocellular Carcinoma," The New England Journal of Medicine, 2008, 359:378-390.
Notice of Allowance in Israeli Patent Application No. 250290, dated Mar. 17, 2020, 10 pages (with English Translation).
Notice of Allowance in Russian Patent Application No. 2018119102, dated Jun. 26, 2020, 12 pages (with English Translation.
Notice of Allowance in U.S. Appl. No. 16/225,772, dated Apr. 14, 2020, 22 pages.
Notice of Allowance in U.S. Appl. No. 16/225,772, dated Jul. 24, 2020, 10 pages.
Office Action in Brazilian Patent Application No. BR112015019790-6, dated Apr. 7, 2020, 14 pages (with English Translation).
Office Action in Chinese Patent Application No. 201680007472.7, dated May 6, 2020, 8 pages (with English Translation).
Office Action in Chinese Patent Application No. 201680068110.9, dated Mar. 20, 2020, 15 pages (with English Translation).
Office Action in European Patent Application No. 16768810.0, dated Jun. 18, 2020, 5 pages.
Office Action in Indian Patent Application No. 201747027065, dated Jul. 8, 2020, 2 pages (with English Translation).
Office Action in Indian Patent Application No. 201847015401, dated May 5, 2020, 7 pages (with English Translation).
Office Action in Israeli Patent Application No. 258671, dated Jun. 25, 2020, 8 pages (with English Translation).
Office Action in Mexican Patent Application No. MX/a/2017/009892, dated Jul. 14, 2020, 7 pages (with English Translation).
Office Action in Mexican Patent Application No. MX/a/2018/006329, dated Jul. 17, 2020, 6 pages (with English Translation).
Official Notification in Brazilian Patent Application No. BR112015019790-6, dated Mar. 10, 2020, 4 pages (with English Translation).
Official Notification in U.S. Appl. No. 15/771,193, dated Aug. 10, 2020, 3 pages.
Submission Document in Chinese Patent Application No. 201680068110.9, dated Jul. 8, 2020, 8 pages.
Submission Document in European Patent Application No. 18865416.4, dated Jul. 29, 2020, 11 pages.
Submission Document in Indian Patent Application No. 201747027065, dated May 21, 2020, 23 pages.
Submission Document in Russian Patent Application No. 2018119102, dated Apr. 27, 2020, 14 pages (with English Translation).
Submission Document in U.S. Appl. No. 16/642,105, dated Jun. 8, 2020, 99 pages.
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Translation).
Office Action in Japanese Application No. P2017-556119, dated Sep. 8, 2020, 6 pages (with English Translation).
Submission Document in European Patent Application No. 16768810.0, dated Sep. 30, 2020, 5 pages.
Notice of Allowance in Israeli Patent Application No. 253701, dated Nov. 11, 2020, 9 pages (with English Translation).
Office Action in Chinese Patent Application No. 201680068110.9, dated Nov. 24, 2020, 9 pages (with English Translation).
Office Action in Israeli Patent Application No. 272887, dated Nov. 23, 2020, 5 pages (with English Translation).
Submission Document in Chinese Patent Application No. 201980013339.6, dated Oct. 23, 2020, 6 pages (with English Translation).
Submission Document in U.S. Appl. No. 16/225,772, dated Oct. 21, 2020, 5 pages.
Submission Document in U.S. Appl. No. 16/970,683, dated Dec. 23, 2020, 22 pages.
Forner et al., "Hepatocellular Carcinoma," The Lancet, Mar. 2012, 379:1245-1255.
International Preliminary Report on Patentability in International Application No. PCT/JP2019/012971, dated Oct. 8, 2020, 8 pages.
Notice of Allowance in U.S. Appl. No. 15/771,193, dated Oct. 22, 2020, 29 pages.
Office Action in U.S. Appl. No. 16/970,683, dated Oct. 9, 2020, 29 pages.

(56) References Cited

OTHER PUBLICATIONS

Office Action in Australian Patent Application No. 2016237222, dated Sep. 2, 2020, 6 pages.
Submission Document in Brazilian Patent Application No. BR1120170022680, dated Aug. 31, 2020, 21 pages (with English Translation).
Notice of Allowance in European Patent Application No. 16768810.0, dated Mar. 16, 2021, 71 pages.
Notice of Allowance in Japanese Patent Application No. P2017-556119, dated Mar. 16, 2021, 6 pages (with English Translation).
Notice of Allowance in Mexican Patent Application No. MX/a/2017/009892, dated Dec. 15, 2020, 6 pages (with English Translation).
Notice of Allowance in U.S. Appl. No. 15/771,193, dated Feb. 4, 2021, Feb. 4, 2021, 15 pages.
Notice of Allowance in U.S. Appl. No. 16/225,772, dated Mar. 29, 2021, 22 pages.
Notice of Allowance in U.S. Appl. No. 16/970,683, dated Jan. 15, 2021, 9 pages.
Notice of Allowance in U.S. Appl. No. 16/970,683, dated Feb. 10, 2021, 5 pages.
Notice of Allowance in U.S. Appl. No. 16/970,683, dated Apr. 16, 2021, 11 pages.
Office Action in Argentine Patent Application No. P140100495, dated Jan. 22, 2021, 10 pages (with English Translation).
Office Action in Australian Patent Application No. 2016237222, dated Jan. 29, 2021, 4 pages.
Office Action in Brazilian Patent Application No. BR1120170163926, dated Dec. 8, 2020, 10 pages (with English Translation).
Office Action in Brazilian Patent Application No. BR1120180101036, dated Feb. 9, 2021, 9 pages (with English Translation).
Office Action in Indian Patent Application No. 201747003469, dated Jan. 8, 2021, 2 pages (with English Translation).
Office Action in Mexican Patent Application No. MX/a/2018/006329, dated Jan. 19, 2021, 8 pages (with English Translation).
Submission Document in Australian Patent Application No. 2016237222, dated Jan. 19, 2021, 20 pages.
Submission Document in Australian Patent Application No. 2016237222, dated Mar. 22, 2021, 10 pages.
Submission Document in Brazilian Patent Application No. BR1120170163926, dated Mar. 5, 2021, 19 pages (with English Translation).
Submission Document in Chinese Patent Application No. 201680068110.9, dated Mar. 1, 2021, 14 pages (with English Translation).
Submission Document in Indian Patent Application No. 201747003469, dated Feb. 9, 2021, 8 pages.
Submission Document in Israeli Patent Application No. 272887, dated Mar. 16, 2021, 7 pages (with English Translation).
Submission Document in Mexican Patent Application No. MX/a/2018/006329, dated Mar. 11, 2021, 9 pages (with English Translation).
Submission Document in U.S. Appl. No. 15/771,193, dated Jan. 21, 2021, 12 pages.
Submission Document in U.S. Appl. No. 16/970,683, dated Apr. 9, 2021, 5 pages.
Submission Document in Korean Patent Application No. 10-2020-7005278, dated Jul. 29, 2021, 12 pages (with English Translation).
Submission Document in European Patent Application No. 15834302.0, dated Sep. 14, 2021, 75 pages.
Submission Document in U.S. Appl. No. 15/771,193, dated Aug. 9, 2021, 5 pages.
Submission Document in Indian Patent Application No. 201847015401, dated Aug. 11, 2021, 6 pages.
Notice of Allowance in U.S. Appl. No. 15/771,193, dated Aug. 27, 2021, 26 pages.
Office Action in Korean Patent Application No. 10-2017-7002791, dated Aug. 29, 2021, 7 pages (with English Translation).
Office Action in Chinese Patent Application No. 201680007472.7, dated Aug. 9, 2021, 10 pages (with English Translation).
[No Author], "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Pharmacology and Toxicology, Jul. 2005, 30 pages.
European Search Report in European Application No. 18865416.4, dated May 28, 2021, 9 pages.
Koyama et al., "Abstract B160: First-in-human phase 1 study of E7090, a novel selective inhibitor of FGFRs, in patients with advanced solid tumors," Abstract, AACR-NCI-EORTC International Conference: Molecular Targets and Cancer Therapeutics, Jan. 2018, [Retrieved on May 18, 2021], retrieved from: URL<https://mct.aacrjournals.org/content/17/1_Supplement/B160>, 4 pages.
Notice of Allowance in Australian Patent Application No. 2016237222, dated Apr. 16, 2021, 4 pages.
Notice of Allowance in Malaysian Patent Application No. PI2015702696, dated Jul. 9, 2020, 2 pages (with English Translation).
Notice of Allowance in U.S. Appl. No. 15/771,193, dated May 11, 2021, 12 pages.
Notice of Allowance in U.S. Appl. No. 16/225,772, dated Jul. 12, 2021, 14 pages.
Notice of Allowance in U.S. Appl. No. 16/225,772, dated Jul. 23, 2021, 10 pages.
Notice of Allowance in U.S. Appl. No. 16/970,683, dated Jul. 30, 2021, 12 pages.
Office Action in Australian Patent Application No. 2016374441, dated May 31, 2021, 4 pages.
Office Action in Canadian Patent Application No. 2956270, dated Apr. 22, 2021, 4 pages.
Office Action in European Patent Application No. 15834302.0, dated May 14, 2021, 4 pages.
Office Action in Indian Patent Application No. 201847015401, dated Jun. 29, 2021, 3 pages (with English Translation).
Office Action in Israeli Patent Application No. 258671, dated May 10, 2021, 18 pages (with English Translation).
Office Action in Israeli Patent Application No. 276935, dated Apr. 22, 2021, 5 pages (with English Translation).
Office Action in Mexican Patent Application No. MX/a/2018/006329, dated May 14, 2021, 5 pages (with English Translation).
Office Action in U.S. Appl. No. 16/642,105, dated Jun. 28, 2021, 65 pages.
Submission Document in Brazilian Patent Application No. BR1120180101036, dated Apr. 26, 2021, 20 pages (with English Translation).
Submission Document in Canadian Patent Application No. 2956270, dated Jun. 22, 2021, 26 pages.
Submission Document in Israeli Patent Application No. 258671, dated Aug. 3, 2021, 4 pages (with English Translation).
Submission Document in Israeli Patent Application No. 276935, dated Jul. 13, 2021, 4 pages (with English Translation).
Submission Document in U.S. Appl. No. 15/771,193, dated May 3, 2021, 5 pages.
Submission Document in U.S. Appl. No. 16/970,683, dated Jul. 14, 2021, 5 pages.
Formisano et al., "Association of FGFRI with ERα Maintains Ligand-Independent ER Transcription and Mediates Resistance to Estrogen Deprivation in $ER^+$ Breast Cancer," Clinical Cancer Research, 2017, 23(20):6138-6150.
International Search Report and Written Opinion in International Application No. PCT/JP2021/028008, dated Aug. 31, 2021 21 pages (with English Translation).
Katoh, "Fibroblast growth factor receptors as treatment targets in clinical oncology," Nature Reviews, Clinical Oncology, 2019, 16(2):105-122.
Musolino et al., "Phase II, randomized, placebo-controlled study of dovitinib in combination with fulvestrant in postmenopausal patients with $Hr^+$, $HER2^-$ breast cancer that had progressed during or after prior endocrine therapy," Breast Cancer Research, 2017, 19:18.

(56) References Cited

OTHER PUBLICATIONS

Quintela-Fandino et al., "Nintedanib plus letrozole in early breast cancer: a phase 0/1 pharmacodynamic, pharmacokinetic, and safety clinical trial of combined FGFR1 and aromatase inhibition, " Breast Cancer Research, 2019, 21:69.
Seckl et al., "Radical trial: A phase Ib/IIa study to assess the safety and efficacy of AZD4547 in combination with either anastrozole or letrozole in ER positive breast cancer patients progressing on these aromatase inhibitors (Als)," Journal of Clinical Oncology, 2017, 35(15):Supplement 1, 4 pages.
Submission Document in U.S. Appl. No. 16/642,105, dated Sep. 15, 2021, 7 pages.
Submission Document in Australian Patent Application No. 2016374441, dated Sep. 22, 2021, 9 pages.
Notice of Allowance in U.S. Appl. No. 16/225,772, dated Jan. 11, 2022, 9 pages.
Official Notification in Indian Patent Application No. 201847015401, dated Dec. 13, 2021, 21 pages.
Stahl et al., "Handbook of Pharmaceutical Salts Properties, Selection, and Use," 1st ed., Cover Page with Table of Contents, John Wiley & Sons, 2002, 4 pages.
Office Action in Chinese Patent Application No. 201680068110.9, dated Jan. 24, 2022, 10 pages (with English Translation).
Submission Document in Egyptian Patent Application No. PCT1285/2015, dated Jan. 4, 2022, 17 pages (with English Translation).
Submission Document in Canadian Patent Application No. 2956270, dated Jan. 13, 2022, 5 pages.
Submission Document in U.S. Appl. No. 16/642,105, dated Jan. 5, 2022, 17 pages.
European Search Report in European Application No. 19777797.2, dated Nov. 15, 2021, 8 pages.
Futami et al., "ASP5878, a Novel Inhibitor of FGFR1, 2, 3, and 4, Inhibits the Growth of FGF19-Expressing Hepatocellular Carcinoma," Molecular Cancer Therapeutics, 2017, 16(1):68-75, XP055858063.
Notice of Allowance in Australian Patent Application No. 2016374441, dated Oct. 8, 2021, 3 pages.
Notice of Allowance in European Patent Application No. 15834302.0, dated Oct. 21, 2021, 56 pages.
Notice of Allowance in European Patent Application No. 15834302.0, dated Dec. 22, 2021, 56 pages.
Notice of Allowance in Korean Patent Application No. 10-2017-7002791, dated Nov. 29, 2021, 3 pages (with English Translation).
Notice of Allowance in U.S. Appl. No. 15/771,193, dated Dec. 10, 2021, 42 pages.
Notice of Allowance in U.S. Appl. No. 16/225,772, dated Dec. 21, 2021, 38 pages.
Notice of Allowance in U.S. Appl. No. 16/970,683, dated Nov. 3, 2021, 16 pages.
Notice of Allowance in U.S. Appl. No. 16/970,683, dated Nov. 10, 2021, 6 pages.
Office Action in Brazilian Patent Application No. BR1120170022680, dated Apr. 7, 2020, 9 pages (with English Translation).
Office Action in Canadian Patent Application No. 2956270, dated Sep. 28, 2021, 3 pages.
Office Action in Egyptian Patent Application No. PCT1285/2015, dated Oct. 5, 2021, 11 pages (with English Translation).
Office Action in Indian Patent Application No. 202047007881, dated Nov. 12, 2021, 5 pages (with English Translation).
Office Action in U.S. Appl. No. 16/642,105, dated Oct. 18, 2021, 19 pages.
Submission Document in Brazilian Patent Application No. BR1120200038490, dated Sep. 9, 2021, 51 pages (with English Translation).
Submission Document in Canadian Patent Application No. 2956270, dated Oct. 25, 2021, 7 pages.
Submission Document in European Patent Application No. 15834302.0, dated Dec. 3, 2021, 6 pages.
Submission Document in European Patent Application No. 18865416.4, dated Dec. 16, 2021, 13 pages.
Submission Document in Korean Patent Application No. 10-2017-7002791, dated Oct. 8, 2021, 23 pages (with English Translation).
Submission Document in U.S. Appl. No. 15/771,193, dated Nov. 22, 2021, 5 pages.
Submission Document in U.S. Appl. No. 16/970,683, dated Oct. 28, 2021, 5 pages.
Yu et al., "A FGFR1 inhibitor patent review: progress since 2010," Expert Opinion on Therapeutic Patents, 2016, pp. 1-16, XP055339480.
Office Action in Russian Patent Application No. 2020127993, dated Dec. 27, 2021, 21 pages (with English Translation).
Notice of Allowance in Canadian Patent Application No. 2956270, dated Apr. 12, 2022, 1 page (with English Translation).
Notice of Allowance in Russian Patent Application No. 2020127993, dated May 4, 2022, 12 pages (with English Translation).
Notice of Allowance in U.S. Appl. No. 15/771,193, dated Mar. 24, 2022, 14 pages.
Notice of Allowance in U.S. Appl. No. 16/225,772, dated Apr. 7, 2022, 11 pages.
Notice of Allowance in U.S. Appl. No. 16/225,772, dated Apr. 20, 2022, 13 pages.
Office Action in Canadian Patent Application No. 2974937, dated May 2, 2022, 5 pages.
Office Action in Chinese Patent Application No. 201680007472.7, dated Feb. 25, 2022, 14 pages (with English Translation).
Office Action in Indian Patent Application No. 202047036696, dated Feb. 24, 2022, 6 pages (with English Translation).
Office Action in Israeli Patent Application No. 258671, dated Apr. 12, 2022, 12 pages (with English Translation).
Office Action in Mexican Patent Application No. MX/a/2020/002083, dated May 12, 2022, 9 pages (with English Translation).
Office Action in Mexican Patent Application No. MX/a/2020/008610, dated Apr. 12, 2022, 7 pages (with English Translation).
Office Action in Sri Lankan Patent Application No. 18355, dated Feb. 28, 2022, 1 page.
Office Action in U.S. Appl. No. 16/642,105, dated Mar. 10, 2022, 25 pages.
Official Notification in U.S. Appl. No. 16/970,683, dated May 10, 2022, 4 pages.
Submission Document in Chinese Patent Application No. 201680068110.9, dated Mar. 8, 2022, 40 pages (with English Translation).
Submission Document in European Patent Application No. 19777797.2, dated May 2, 2022, 18 pages.
Submission Document in Indian Patent Application No. 201847015401, dated Mar. 10, 2022, 16 pages.
Submission Document in Indian Patent Application No. 202047007881, dated May 11, 2022, 13 pages.
Submission Document in Russian Patent Application No. 2020108284, dated Mar. 17, 2022, 16 pages (with English Translation).
Submission Document in Russian Patent Application No. 2020127993, dated Mar. 11, 2022, 9 pages (with English Translation).
Submission Document in U.S. Appl. No. 15/771,193, dated Mar. 7, 2022, 5 pages.
Submission Document in U.S. Appl. No. 16/642,105, dated Jun. 7, 2022, 10 pages.
Submission Document in U.S. Appl. No. 15/771,193, dated Jun. 23, 2022, 5 pages.
Office Action in Chinese Patent Application No. 201680068110.9, dated Jun. 1, 2022, 15 pages (with English Translation).
Office Action in Russian Patent Application No. 2020108284, dated May 17, 2022, 30 pages (with English Translation).
Office Action in Indian Patent Application No. 202047007881, dated Jun. 1, 2022, 3 pages (with English Translation).
Submission Document in Mexican Patent Application No. MX/a/2020/008610, dated Jun. 15, 2022, 7 pages (with English Translation).
ClinicalTrials.gov [online], "History of Changes for Study: NCT02275910 Phase 1 Study of E7090 in Subjects With Solid Tumor," Versions A & B of Jun. 26, 2017, retrieved from: URL<https://clinicaltrials.gov/ct2/history/NCT02275910?A=5&B=5&C=merged#StudyPageTop>, 4 pages.

(56) References Cited

OTHER PUBLICATIONS

Li et al., "Research and Development Progress on the Relationship between Small Molecule Anti-Tumor FGFR Inhibitor and FGFR Protein," Acta Pharmaceutica Sinica, 2016, 51(11):1689-1697 (with English Translation).
Notice of Allowance in Mexican Patent Application No. MX/a/2020/008610, dated Jul. 15, 2022, 4 pages (with English Translation).
Notice of Allowance in U.S. Appl. No. 15/771,193, dated Jul. 12, 2022, 4 pages.
Notice of Allowance in U.S. Appl. No. 15/771,193, dated Jul. 6, 2022, 19 pages.
Notice of Allowance in U.S. Appl. No. 16/225,772, dated Sep. 8, 2022, 23 pages.
Notice of Allowance in U.S. Appl. No. 16/225,772, dated Sep. 21, 2022, 10 pages.
Office Action in Argentine Patent Application No. P140100495, dated Sep. 6, 2022, 6 pages (with English Translation).
Office Action in Australian Patent Application No. 2018349961, dated Jul. 19, 2022, 1 page.
Office Action in Brazilian Patent Application No. BR1120200038490, dated Sep. 13, 2022, 11 pages (with English Translation).
Office Action in Chinese Patent Application No. 201880055615.0, dated Aug. 1, 2022, 21 pages (with English Translation).
Office Action in Egyptian Patent Application No. PCT1285/2015, dated Aug. 7, 2022, 10 pages (with English Translation).
Office Action in Indian Patent Application No. 201847015401, dated Aug. 4, 2022, 3 pages (with English Translation).
Office Action in Israeli Patent Application No. 272887, dated Aug. 17, 2022, 3 pages.
Office Action in Japanese Application No. P2020-512051, dated Sep. 13, 2022, 8 pages (with English Translation).
Office Action in Mexican Patent Application No. MX/a/2020/002083, dated Jul. 21, 2022, 11 pages (with English Translation).
Office Action in United States Application No. 16/642,105, dated Jul. 25, 2022, 17 pages.
Submission Document in Indian Patent Application No. 202047036696, dated Jul. 15, 2022, 11 pages.
Submission Document in Israeli Patent Application No. 258671, dated Jul. 25, 2022, 24 pages.
Submission Document in Mexican Patent Application No. MX/a/2020/002083, dated Jul. 11, 2022, 21 pages (with English Translation).
Submission Document in Mexican Patent Application No. MX/a/2020/002083, dated Sep. 22, 2022, 2 pages (with English Translation).
Submission Document in Russian Patent Application No. 2020108284, dated Aug. 10, 2022, 11 pages (with English Translation).
Submission Document in Indian Patent Application No. 201847015401, dated Oct. 18, 2022, 3 pages.
Office Action in Chinese Patent Application No. 201980013339.6, dated Feb. 12, 2023, 9 pages (with English Translation).
Submission Document in Argentine Patent Application No. P140100495, dated Feb. 10, 2023, 8 pages (with English Translation).
Submission Document in Canadian Patent Application No. 2974937, dated Mar. 9, 2023, 8 pages.
Submission Document in Japanese Patent Application No. P2020-510951, dated Feb. 28, 2023, 15 pages (with English Translation).
Office Action in Russian Patent Application No. 2020108284, dated Oct. 12, 2022, 11 pages (with English Translation).
[No Author], "Progress on molecular mechanism of liver cancer in general surgery department of Ruijin Hospital, Shanghai Jiaotong University School Of Medicine," Journal of Shanghai Jiaotong University (Medical Science), 2016, 36(7):1022 (with English Translation).
Bøttcher et al., "Treatment of advanced HR+/HER2− breast cancer with new targeted agents in combination with endocrine therapy: a review of efficacy and tolerability based on available randomized trials on everolimus, ribociclib, palbociclib and abemaciclib," Acta Oncologica, 2019, 58(2):147-153.
Deeks et al., "Exemestane—A Review of its Use in Postmenopausal Women with Breast Cancer," Drugs, 2009, 69(7):889-918.
Formisano et al., "Aberrant FGFR signaling mediates resistance to CDK4/6 inhibitors in ER+ breast cancer," Nature Communications, 2019, 10:1373, 14 pages.
Howell et al., "Comparison of fulvestrant versus tamoxifen for the treatment of advanced breast cancer in postmenopausal women previously untreated with endocrine therapy: a multinational, double-blind, randomized trial," Journal of Clinical Oncology, 2004, 22(9):1605-1613.
International Search Report in International Application No. PCT/JP2021/015546, dated May 25, 2021, 4 pages (with English Translation).
International Search Report in International Application No. PCT/JP2021/028008, dated Aug. 31, 2021, 6 pages (with English Translation).
Miyano et al., "E7090, a novel selective inhibitor of fibroblast growth factor receptors, displays potent antitumor activity and prolongs survival in preclinical models," Molecular Cancer Therapeutics, 2016, 15(11):2630-2639.
Nayar et al., "Acquired HER2 mutations in $ER^+$ metastatic breast cancer confer resistance to estrogen receptor-directed therapies," Nature Genetics, 2019, 51:207-216.
Notice of Allowance in Brazilian Patent Application No. BR1120170163926, dated Jan. 3, 2023, 6 pages (with English Translation).
Notice of Allowance in Korean Patent Application No. 10-2018-7014626, dated Dec. 19, 2022, 6 pages (with English Translation).
Notice of Allowance in U.S. Appl. No. 15/771,193, dated Oct. 26, 2022, 14 pages.
Notice of Allowance in U.S. Appl. No. 16/225,772, dated Jan. 12, 2023, 27 pages.
Notice of Allowance in U.S. Appl. No. 16/225,772, dated Jan. 24, 2023, 7 pages.
Office Action in Brazilian Patent Application No. BR1120170163926, dated Oct. 11, 2022, 5 pages (with English Translation).
Office Action in Canadian Patent Application No. 2974937, dated Dec. 6, 2022, 3 pages.
Office Action in Canadian Patent Application No. 3001969, dated Nov. 9, 2022, 4 pages.
Office Action in Chinese Patent Application No. 201980013339.6, dated Oct. 10, 2022, 16 pages (with English Translation).
Office Action in Indian Patent Application No. 202047036696, dated Jan. 11, 2023, 2 pages (with English Translation).
Office Action in Israeli Patent Application No. 258671, dated Jan. 19, 2023, 13 pages (with English Translation).
Office Action in Japanese Application No. P2020-510951, dated Jan. 4, 2023, 7 pages (with English Translation).
Office Action in Mexican Patent Application No. MX/a/2020/002083, dated Nov. 29, 2022, 11 pages (with English Translation).
Official Notification in Australian Patent Application No. 2019241625, Jan. 4, 2023, 1 page.
Seki et al., "Efficacy and Safety of Palbociclib and Fulvestrant in Japanese Patients With ER+/HER2− Advanced/Metastatic Breast Cancer," In Vivo, 2019, 33:2037-2044.
Submission Document in Brazilian Patent Application No. BR1120170163926, dated Dec. 23, 2022, 18 pages (with English Translation).
Submission Document in Brazilian Patent Application No. BR1120200038490, dated Dec. 9, 2022, 37 pages (with English Translation).
Submission Document in Chinese Patent Application No. 201980013339.6, dated Feb. 3, 2023, 14 pages (with English Translation).
Submission Document in Singaporean Patent Application No. 10201913213W, dated Dec. 1, 2022, 8 pages.
Submission Document in Sri Lankan Patent Application No. 18355, dated Nov. 14, 2022, 2 pages.
Submission Document in U.S. Appl. No. 15/771,193, dated Oct. 5, 2022, 5 pages.
Submission Document in U.S. Appl. No. 16/642,105, dated Oct. 25, 2022, 17 pages.

(56) References Cited

OTHER PUBLICATIONS

Wang et al., "Downregulation of microRNA-214 and overexpression of FGFR-1 contribute to hepatocellular carcinoma metastasis," Biochemical and Biophysical Research Communications, 2013, 439(1):47-53.
Ye et al., "Expression and Significance of FGFR2 in Colon Cancer," China Modern Doctor, 2012, 50(5):1-3 (with English Translation).
International Preliminary Report on Patentability in Patent Application No. PCT/JP2021/028008, dated Feb. 9, 2023, 6 pages.
Notice of Allowance in U.S. Appl. No. 15/771,193, dated Feb. 17, 2023, 15 pages.
Office Action in Korean Patent Application No. 10-2017-7021185, dated Feb. 10, 2023, 10 pages (with English Translation).
Office Action in U.S. Appl. No. 16/642,105, dated Feb. 17, 2023, 24 pages.
Submission Document in Canadian Patent Application No. 3001969, dated Feb. 15, 2023, 7 pages.
Submission Document in U.S. Appl. No. 15/771,193, dated Jan. 25, 2023, 5 pages.
Office Action in Israeli Patent Application No. 276935, dated Jan. 3, 2023, 4 pages (with English Translation).
International Search Report in International Application No. PCT/JP2016/087349, dated Feb. 7, 2017, 2 pages (English Translation).
Notice of Allowance in Brazilian Patent Application No. BR1120180101036, dated Apr. 11, 2023, 7 pages (with English translation).
Notice of Allowance in Canadian Patent Application No. 2974937, dated Jun. 2, 2023, 1 page (with English Translation).
Notice of Allowance in Canadian Patent Application No. 3001969, dated May 26, 2023, 1 page (with English Translation).
Notice of Allowance in Korean Patent Application No. 10-2017-7021185, dated Apr. 27, 2023, 7 pages (with English Translation).
Notice of Allowance in U.S. Appl. No. 16/225,772, dated May 17, 2023, 13 pages.
Notice of Allowance in U.S. Appl. No. 16/225,772, dated May 26, 2023, 9 pages.
Office Action in Egyptian Patent Application No. PCT1285/2015, dated Apr. 10, 2023, 8 pages (with English Translation).
Office Action in Japanese Application No. P2020-512051, dated Mar. 7, 2023, 2 pages (with English Translation).
Official Notification in Australian Patent Application No. 2019241625, dated Apr. 13, 2023, 1 page.
Submission Document in Korean Patent Application No. 10-2017-7021185, dated Apr. 3, 2023, 18 pages (with English translation).
Notice of Allowance in U.S. Appl. No. 15/771,193, dated Jun. 14, 2023, 14 pages.
Notice of Allowance in U.S. Appl. No. 16/225,772, dated Jun. 14, 2023, 8 pages.
Submission Document in U.S. Appl. No. 15/771,193, dated May 16, 2023, 5 pages.
Notice of Allowance in U.S. Appl. No. 15/771,193, dated Jul. 10, 2023, 6 pages.
Office Action in Chinese Patent Application No. 202180028460.3 dated Jun. 12, 2023, 13 pages (English Translation).
Office Action in Australian Patent Application No. 2018349961, dated Aug. 15, 2023, 4 pages.
Submission Document in Chinese Patent Application No. 202180028460.3, dated Sep. 25, 2023, 31 pages (with English Translation).
Zhou et al., "CDK4/6 inhibitor resistance in estrogen receptor positive breast cancer, a 2023 perspective," Frontiers in Cell and Developmental Biology, Mar. 22, 2023, 11:1-12.
Office Action in Chinese Patent Application No. 202180028460.3, dated Oct. 13, 2023, 10 pages (with English Translation).
Submission Document in Chinese Patent Application No. 202180028460.3, dated Dec. 21, 2023, 6 pages (with English Translation).
Office Action in Chinese Patent Application No. 202180028460.3, dated Jan. 10, 2024, 9 pages (with English Translation).
Notice of Allowance in U.S. Appl. No. 16/225,772, dated Dec. 6, 2023, 39 pages.
Notice of Allowance in U.S. Appl. No. 15/771,193, dated Apr. 4, 2024, 17 pages.
Notice of Allowance in U.S. Appl. No. 16/225,772, dated Apr. 2, 2024, 15 pages.
European Search Report in European Application No. 21787967.5, dated Feb. 16, 2024, 9 pages.
European Search Report in European Application No. 21850938.8, dated Mar. 6, 2024, 8 pages.
International Preliminary Report on Patentability in International Application No. PCT/JP2022/032309, dated Mar. 14, 2024, 7 pages.
International Preliminary Report on Patentability in International Application No. PCT/JP2022/032310, dated Mar. 14, 2024, 7 pages.
Mouron et al., "FGFR1 amplification or overexpression and hormonal resistance in luminal breast cancer: rationale for a triple blockade of ER, CDK4.6, and FGFR1," Breast Cancer Research (Online Edition), Feb. 12, 2021, 23(1):1-16.
Notice of Allowance in U.S. Appl. No. 15/771,193, dated Dec. 26, 2023, 13 pages.
Notice of Allowance in U.S. Appl. No. 15/771,193, dated Sep. 20, 2023, 11 pages.
Office Action in Indian Patent Application No. 201847015401, dated Dec. 22, 2023, 3 pages.
Office Action in Indian Patent Application No. 201847015401, dated Mar. 8, 2023, 6 pages.
Submission Document in U.S. Appl. No. 15/771,193, dated Dec. 18, 2023, 8 pages.
Submission Document in European Patent Application No. 21787967.5, dated May 13, 2024, 15 pages.
Submission Document in U.S. Appl. No. 15/771,193, dated Mar. 25, 2024, 9 pages.
Notice of Allowance in U.S. Appl. No. 15/771,193, dated Aug. 21, 2024, 4 pages.
Notice of Allowance in U.S. Appl. No. 16/225,772, dated Sep. 20, 2024, 21 pages.
European Search Report in European Application No. 21886203.5, dated Sep. 4, 2024, 10 pages.
Office Action in Russian Patent Application No. 2022127618, dated Aug. 14, 2024, 37 pages (with English Translation).
Cheng et al., "An overview of the binding models of FGFR tyrosine kinases in complex with small molecule inhibitors," European Journal of Medicinal Chemistry, 2017, 126:476-490.
Kawano et al., "Antitumor Activity of Tasurgratinib as an Orally Available FGFR1-3 Inhibitor in Cholangiocarnoma Models With FGFR2-fusion," Anticancer Research, 2024, 44:2393-2406.
Submission Document in European Patent Application No. 21850938.8, dated Sep. 23, 2024, 12 pages (Responses to the Communication pursuant to Rule 70(2)).
Submission Document in European Patent Application No. 21850938.8, dated Sep. 23, 2024, 39 pages (Responses to the Invitation to file a translation of a previous application pursuant to R.53(3) EPC, Translations of the priority documents (JP2020130935 and JP2020163258)).
Notice of Allowance in U.S. Appl. No. 15/771,193, dated Jul. 26, 2024, 12 pages.
Notice of Allowance in U.S. Appl. No. 16/225,772, dated Jul. 26, 2024, 14 pages.
Office Action in Chinese Patent Application No. 202180045666.7, dated Jul. 31, 2024, 23 pages (with English Translation).
Office Action in Korean Patent Application No. 10-2020-7024300, dated Jul. 15, 2024, 8 pages (with English Translation).
Submission Document in U.S. Appl. No. 15/771,193, dated Jul. 3, 2024, 11 pages.
Office Action in Chinese Patent Application No. 202210570963.X, dated Oct. 18, 2024, 12 pages (with English Translation).
Submission Document in Chinese Patent Application No. 202210570963.X, dated Feb. 5, 2025, 9 pages (with English Translation).
Submission Document in Russian Patent Application No. 2022127618, dated Oct. 10, 2024, 23 pages (with English Translation).
Office Action in Chinese Patent Application No. 202210570963.X, dated Feb. 20, 2025, 10 pages (with English Translation).

(56) References Cited

OTHER PUBLICATIONS

Notice of Allowance in U.S. Appl. No. 16/225,772, dated Feb. 14, 2025, 6 pages.
[No Author Listed], "Process Chemistry It is," from Pharmaceutical Synthesis to Manufacturing, 2nd Edition, 2014, pp. 143-144, Maruzen Publication Inc., Co., 5 pages (with partial English Translation).
European Search Report in European Patent Application No. 22864455.5, dated Apr. 30, 2025, 16 pages.
European Search Report in European Patent Application No. 22864456.3, dated Apr. 30, 2025, 11 pages.
Imakura et al., "*Regioselective cleavage Reaction of the Aromatic methylenedioxy Ring.* v. *Cleavage with Sodium Alkoxides-Alcohols, Potassium tert-Butoxide-Alcohols, Dimsyl Anion-Methyl Alcohol, Metallic Sodium-Alcohols, and Sodium Cyanide in Dipolar Aprotic Solvents*," Chemical & Pharmaceutical Bulletin, 1992, 40(7):1691-1696.
Kwapisz, "Cyclin-dependent kinase 4/6 inhibitors in breast cancer: palbociclib, ribociclib, and abemaciclib," Breast Cancer Research and Treatment, Nov. 2017, 166:41-54.
Numura et al., "Endocrine Adjuvant Therapy with the Antiestrogen, Mepitiostane, in Operable Breast Cancer Patients on the Basis of Estrogen Receptor Assay," GANN, Apr. 30, 1978, 69(2):281-282.
Notice of Allowance in U.S. Appl. No. 16/225,772, dated Mar. 27, 2025, 7 pages.
Notice of Allowance in U.S. Appl. No. 16/225,772, dated Mar. 9, 2025, 7 pages.
Office Action in Chinese Patent Application No. 202180072012.3, dated Apr. 25, 2025, 20 pages (with English Translation).
Office Action in Japanese Patent Application No. 2022-515429, dated Apr. 22, 2025, 13 pages (with English Translation).
Office Action in Taiwanese Patent Application No. 110127880, dated Apr. 10, 2025, 29 pages (with English Translation).
Office Action in Taiwanese Patent Application No. 110139617, dated Apr. 15, 2025, 8 pages (with English Translation).
Office Action in U.S. Appl. No. 17/918,829, dated May 22, 2025, 76 pages.
Office Action in U.S. Appl. No. 18/008,304, dated May 15, 2025, 98 pages.
Submission Document in Chinese Patent Application No. 202210570963.X, dated May 20, 2025, 8 pages (with English Translation).
Yin et al., "A General and Efficient 2-Amination of Pyridines and Quinolines," Journal of Organic Chemistry, 2007, 72(12):4554-4557.
Office Action in Chinese Patent Application No. 202210570963.X, dated Aug. 19, 2025, 10 pages (with English translation).
Reexamination Decision for Chinese Patent Application No. 202210570963.X, dated Jan. 5, 2026, 17 pages (with English translation).
Submission Document in Chinese Patent Application No. 202210570963.X, dated Nov. 3, 2025, 9 pages (with English translation).

* cited by examiner

1: FGFR2-BICC1 type2 wild
2: FGFR2-BICC1 type2 KD
3: FGFR2-TXLNA wild
4: FGFR2-TXLNA KD
5: FGFR2-KCTD1 wild
6: FGFR2-KCTD1 KD

THERAPEUTIC AGENT FOR BILE DUCT CANCER

TECHNICAL FIELD

The present invention relates to a therapeutic agent for bile duct cancer comprising a monocyclic pyridine derivative or a pharmacologically acceptable salt thereof having an FGFR inhibitory activity.

BACKGROUND ART

The compound represented by the formula (I) is known as 5-((2-(4-(1-(2-hydroxyethyl)piperidin-4-yl)benzamide)pyridin-4-yl)oxy)-6-(2-methoxyethoxy)-N-methyl-1H-indole-1-carboxamide. It has been reported that the compound represented by the formula (I) has an inhibitory activity on fibroblast growth factor receptors (FGFRs) 1, 2 and 3 and has a cell growth suppressing activity in gastric cancer, lung cancer, bladder cancer and endometrial cancer (Patent Literature 1).

[Chemical Formula 1]

(I)

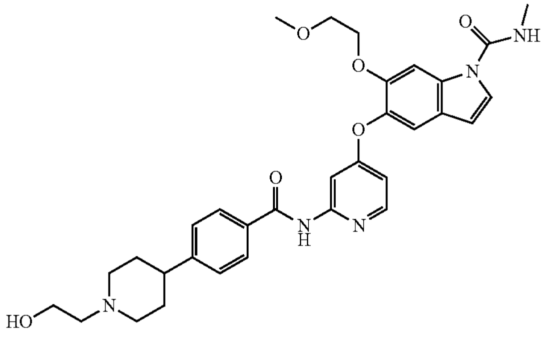

Bile duct cancer is low in incidence, but is known as a tumor with poor prognosis. The main therapeutic method for the bile duct cancer is surgical extirpation of the bile duct, but in many cases cancer cells cannot be completely removed. In such a case, a combined administration of gemcitabine and cisplatin is carried out after the surgery (Non Patent Literature 1).

CITATION LIST

Patent Literature

Patent Literature 1: US 2014-235614

Non Patent Literature

Non Patent Literature 1: Celina Ang, "Role of the fibroblast growth factor receptor axis in cholangiocarcinoma", Journal of Gastroenterology and Hepatology, vol. 30, p. 1116-1122, 2015.

SUMMARY OF INVENTION

Technical Problem

However, a sufficient therapeutic activity cannot be obtained by the so far reported therapeutic agents for bile duct cancer.

Solution to Problem

In view of such a situation, the present inventors have conducted intensive studies and as a result, have found that the compound represented by the formula (I) is effective for the treatment of bile duct cancer, and have completed the present invention.

That is, the present invention provides the following [1] to [12]:

[1] A therapeutic agent for bile duct cancer comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by the formula (I) or a pharmaceutically acceptable salt thereof.

[Chemical Formula 2]

(I)

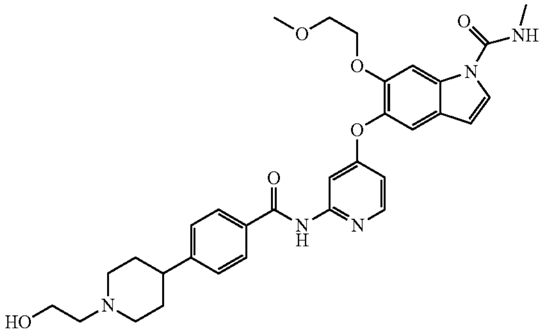

[2] The therapeutic agent according to [1], wherein the bile duct cancer is intrahepatic bile duct cancer.

[3] A pharmaceutical composition for the treatment of bile duct cancer, comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by the formula (I) or a pharmaceutically acceptable salt thereof as an active ingredient.

[4] The pharmaceutical composition according to [3], wherein the bile duct cancer is intrahepatic bile duct cancer.

[5] A method for treating bile duct cancer, comprising administering to a patient a pharmacologically effective amount of 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by the formula (I) or a pharmaceutically acceptable salt thereof.

[6] The method according to [5], wherein the patient has been confirmed to have a gene encoding FGFR2-fusion protein before the administration.

[7] The method according to [6], wherein the gene encoding the FGFR 2-fusion protein is FGFR2-AHCYL1, FGFR2-BICC1 type1, FGFR2-BICC1 type2, FGFR2-TXLNA or FGFR2-KCTD1.

[8] The method according to any one of [5] to [7], wherein the bile duct cancer is intrahepatic bile duct cancer.

[9] 5-((2-(4-(1-(2-Hydroxyethyl)piperidin-4-yl)benzamide)pyridin-4-yl)oxy)-6-(2-methoxyethoxy)-N-methyl-1H-indole-1-carboxamide represented by the formula (I) or pharmaceutically acceptable salts thereof for the treatment of bile duct cancer.

[10] The compound or pharmaceutically acceptable salts thereof according to [9], wherein the bile duct cancer is intrahepatic bile duct cancer.

[11] Use of 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by the formula (I) or pharmaceutically acceptable salts thereof for the preparation of a therapeutic agent for bile duct cancer.

[12] The use according to [11], wherein the bile duct cancer is intrahepatic bile duct cancer.

Advantageous Effects of Invention

According to the present invention, the therapeutic agent which may be effective for the treatment of bile duct cancer can be provided.

DESCRIPTION OF EMBODIMENTS

Figure 1:
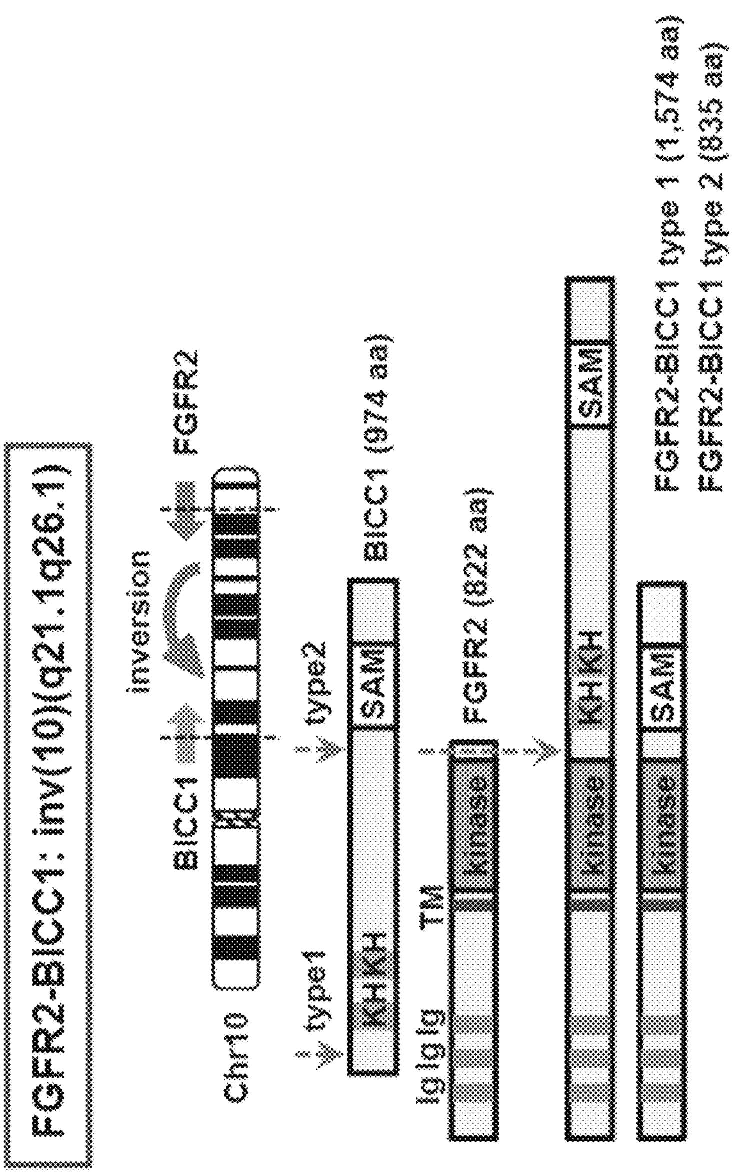
FIG. 1 is a schematic diagram illustrating structures of FGFR2-BICC1 type1 and type2 genes.

One embodiment of the present invention is a therapeutic agent for bile duct cancer comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by the formula (I) or a pharmaceutically acceptable salt thereof.

[Chemical Formula 3]

(I)

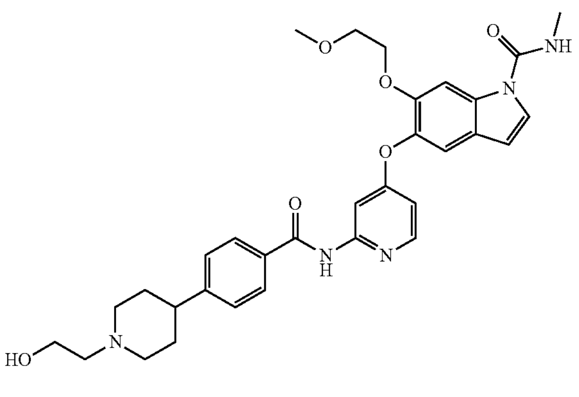

In the present specification, examples of pharmacologically acceptable salts may include salts with inorganic acids, salts with organic acids or salts with acidic amino acids.

Suitable examples of salts with inorganic acids include salts with hydrochloric acid, hydrobromic acid, sulfuric acid, nitric acid and phosphoric acid.

Suitable examples of salts with organic acids include salts with carboxylic acids such as acetic acid, succinic acid, fumaric acid, maleic acid, tartaric acid, citric acid, lactic acid, stearic acid and benzoic acid, and salts with sulfonic acids such as methanesulfonic acid, ethanesulfonic acid and p-toluenesulfonic acid.

Suitable examples of salts with acidic amino acids include salts with aspartic acid and glutamic acid.

A preferred pharmacologically acceptable salt is a succinate or maleate, and a more preferred salt is a succinate. As the pharmacologically acceptable salt, a salt containing succinic acid 1.5 times on a mass basis more than the compound represented by the formula (I) (1.5 succinate) is particularly preferable.

The compound represented by the formula (I) or pharmacologically acceptable salts thereof according to the present invention can be produced by the process described in the Patent Literature 1.

In the present specification, the term "biliary duct" is used synonymously with "biliary tract". That is, bile duct cancer refers to intrahepatic bile duct cancer, extrahepatic bile duct cancer, cystic duct cancer, gallbladder cancer or duodenum papilla cancer. The bile duct cancer also include these cancers metastasized to sites other than the bile duct. The therapeutic agent for bile duct cancer of the present invention is particularly effective against intrahepatic bile duct cancer.

The therapeutic agent for bile duct cancer of the present invention may be in the form of a preparation for oral administration, for example, a solid preparation such as a tablet, a granule, a subtle granule, a powder or a capsule, or a solution, a jelly or a syrup. The therapeutic agent for bile duct cancer of the present invention may also be in the form of a preparation for parenteral administration such as an injection, a suppository, an ointment or a cataplasm.

When preparing the preparation for oral administration, a pharmaceutically acceptable carrier such as an excipient, a binder, a disintegrator, a lubricant and a colorant may be added as appropriate to the compound represented by the formula (I) or a pharmaceutically acceptable salt thereof. The preparation such as a tablet, a granule, a powder and a capsule may also be coated as appropriate.

When preparing an injection (such as for intravenous administration, intramuscular administration, subcutaneous administration or intraperitoneal administration), a pharmaceutically acceptable carrier such as a pH adjuster, a buffer, a suspending agent, a solubilizing agent, an antioxidant, a preservative (an antiseptic agent) or an isotonizing agent may be added as appropriate to the compound represented by the formula (I) or a pharmaceutically acceptable salt thereof, and then the injection may be prepared by the conventional method. The injection may also be lyophilized to provide a lyophilized preparation which is dissolved before use.

When preparing an external preparation, a base material may be added to the compound represented by the formula (I) or a pharmaceutically acceptable salt thereof, and the above-mentioned pharmaceutically acceptable carrier such as a preservative, an stabilizer, a pH adjuster, an antioxidant or a colorant may be then added thereto as appropriate, and thereafter, for example, a transdermal preparation (such as an ointment or a patch), an eye dropper, a nasal preparation, or a suppository may be prepared by the conventional method.

Examples of base materials which can be used include various materials usually used in pharmaceuticals, quasi drugs, cosmetics and the like.

The therapeutic agent for bile duct cancer of the present invention can be prepared with the compound represented by the formula (I) or a pharmacologically acceptable salt thereof according to the method described in the Japanese Pharmacopoeia 16th edition.

The dosage of the compound represented by the formula (I) or a pharmacologically acceptable salt thereof in the therapeutic agent for bile duct cancer of the present invention can be appropriately selected depending on the severity of the symptoms, the age, sex, body weight and differential sensitivity of the patient, the method of administration, time of administration, interval of administration, the type of pharmaceutical preparation, and the like. The therapeutic agent for bile duct cancer of the present invention, when administered orally, can be administered so that the dosage of the compound represented by the formula (I) or a pharmacologically acceptable salt thereof is 100 μg to 10 g per day, preferably 500 μg to 10 g per day, more preferably 1 mg to 5 g per day for an adult (body weight: 60 kg). The therapeutic agent for bile duct cancer of the present invention can be administered in 1 to 3 divided portions daily.

According to the present invention, a method for treating bile duct cancer, comprising administering to a patient the compound represented by the formula (I) or a pharmaceutically acceptable salt thereof can be provided. It is preferable that the subject for administration is a patient with bile duct cancer, it is more preferable that the subject is a patient with intrahepatic bile duct cancer, and it is particularly preferable that the subject is a patient with bile duct cancer having a gene encoding FGFR 2-fusion protein (FGFR2 fusion gene).

The FGFR2 fusion gene refers to a gene in which the FGFR2 and a particular other gene are fused, and examples of the FGFR2 fusion gene include FGFR2-BICC1 type1, FGFR2-BICC1 type2 (SEQ ID NO: 5), FGFR2-TXLNA (SEQ ID NO: 1), FGFR2-AHCYL1, FGFR2-CCDC6, FGFR2-KCTD1 (SEQ ID NO: 3), FGFR2-MGEA5, FGFR2-TACC3, FGFR2-PPHLN1, FGFR2-KIAA1598, FGFR2-CCAR1, FGFR2-NOL4 and FGFR2-PARK2. Herein, as shown in FIG. 1, FGFR2-BICC1 type1 refers to a gene having FGFR2 fused to the 5' terminal side of KHKH sequence of BICC1 gene, while FGFR2-BICC1 type2 refers to a gene having FGFR2 fused to the 5' terminal side of SAM region (sterile c motif) of BICC1 gene. FGFR2-BICC1 type1 encodes a peptide consisting of 1,574 amino acids, whereas FGFR2-BICC1 type2 encodes a peptide consisting of 835 amino acids (SEQ ID NO: 6). BICC1 type1 was also referred to as BICC1 until BICC1 type2 was discovered.

As the patient with bile duct cancer, the patient having FGFR2-AHCYL1, FGFR2-BICC1 type1, FGFR2-BICC1 type2, FGFR2-TXLNA or FGFR2-KCTD1 is preferable, the patient having FGFR2-BICC1 type2, FGFR2-TXLNA or FGFR2-KCTD1 is more preferable, and the patient with FGFR2-BICC1 type2 is particularly preferable.

Before administering the therapeutic agent for bile duct cancer of the present invention, it may be diagnosed whether the subject to be administered has the FGFR2 fusion gene. The method for diagnosing the presence or absence of the FGFR2 fusion gene may be a genetic diagnosis commonly used.

EXAMPLES

The present invention will be described in greater detail by the following examples.

Production Example 1: Production of 5-((2-(4-(1-(2-hydroxyethyl)piperidin-4-yl)benzamide)pyridin-4-yl)oxy)-6-(2-methoxyethoxy)-N-methyl-1H-indole-1-carboxamide 1.5 succinate (hereinafter also referred to as Compound A)

[Chemical Formula 4]

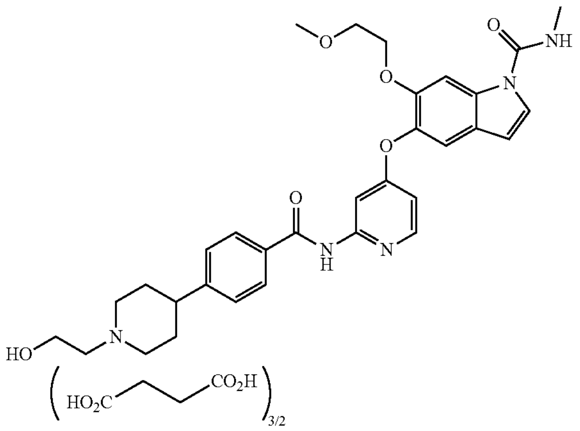

2.93 g of 5-((2-(4-(1-(2-hydroxyethyl)piperidin-4-yl)benzamide)pyridin-4-yl)oxy)-6-(2-methoxyethoxy)-N-methyl-1H-indole-1-carboxamide was weighed out in an eggplant flask, 60 mL of ethanol was added thereto, and the reaction mixture was heated to 70° C. while stirring in an oil bath to dissolve it. Succinic acid (1.23 g) was added, then the heating of the oil bath was stopped, and the reaction mixture was slowly cooled. The reaction mixture was stirred at room temperature for about 2 hours, and further stirred at 5° C. for one hour. The resulting solid was collected by filtration to obtain Compound A (3.70 g).

$^1$H-NMR Spectrum (600 MHz, $CD_3OD$) δ (ppm): 1.96-2.10 (4H, m), 2.52 (6H, s), 2.93 (1H, m), 2.96 (3H, s), 3.01 (2H, m), 3.16 (2H, t, J=5.4 Hz), 3.22 (3H, s), 3.56 (2H, t, J=4.7 Hz), 3.61 (2H, m), 3.87 (2H, t, J=5.4 Hz), 4.14 (2H, t, J=4.6 Hz), 6.61 (1H, d, J=3.6 Hz), 6.68 (1H, dd, J=5.8, 2.3 Hz), 7.37 (1H, s), 7.42 (2H, d, J=8.3 Hz), 7.58 (1H, d, J=3.6 Hz), 7.73 (1H, d, J=2.2 Hz), 7.88 (2H, d, J=8.3 Hz), 8.08 (1H, s), 8.15 (1H, d, J=5.8 Hz).

$^{13}$C-NMR Spectrum (100 MHz, solid state) δ (ppm): 27.1, 28.3, 29.7, 34.8, 38.0, 41.3, 54.0, 57.3, 59.7, 60.9, 72.1, 72.5, 103.3, 104.2, 108.5, 116.9, 126.9, 128.6, 134.5, 136.7, 140.7, 149.4, 151.3, 155.1, 169.5, 170.1, 175.6, 179.9, 183.7.

Construction of the FGFR2 Fusion Genes cDNAs of three types of FGFR2 fusion genes (FGFR2-BICC1 type2 (SEQ ID NO: 5), FGFR2-TXLNA (SEQ ID NO: 1), FGFR2-KCTD1 (SEQ ID NO: 3)) were prepared from cancer tissues from a patient with biliary tract cancer, respectively. A nucleotide sequence encoding a FLAG epitope tag was ligated to the N-terminal of the resulting cDNA of each FGFR2 fusion gene in accordance with the reading frame of translation, and cloned in a pMXs retrovirus vector to construct a retrovirus. Herein, the above ligated FGFR2 fusion gene is also referred to as "wild-type FGFR2 fusion gene". The peptide sequence of the FLAG epitope tag is $H_2N$-DYKDDDDK-COOH (molecular weight: 1,012 Da).

Herein, the polynucleotide sequences of each cDNA of FGFR2, TXLNA and KCTD1 correspond to SEQ ID NOs: 7, 9 and 11, respectively, and the sequences of the peptides encoded by FGFR2, TXLNA and KCTD1 correspond to SEQ ID NOs: 8, 10 and 12, respectively.

Next, a retrovirus having the wild-type FGFR2 fusion gene in which two amino acids in the region encoding FGFR2 kinase were further mutated was constructed. The mutation means that the tyrosine which is a residue at position 568 was replaced by phenylalanine (Y568F) and the tyrosine which is a residue at position 569 was replaced by phenylalanine (Y569F). Herein, the gene obtained by subjecting the wild-type FGFR2 fusion gene to the above-mentioned mutation is also referred to as "KD mutant FGFR2 fusion gene"

Each of these retroviruses was infected to a mouse immortalized fibroblast cell line NIH3T3 cell to transfect the wild-type FGFR2 fusion gene or the KD mutant FGFR2 fusion gene into the cell, to obtain a cell line stably expressing the protein encoded by each fusion gene.

cDNA Cloning:
pMXs Vector (CellBiolabs), Plat-Eretrovirus Packaging Cell Line (CellBiolabs)

Test Example 1: Immunoblot Analysis

First, the wild-type FGFR2 fusion gene or KD mutant FGFR2 fusion gene was transfected into the mouse fibroblast cell line NIH3T3 using the retrovirus, and the obtained cell line was cultured in a liquid culture medium. The cultured cell line was subjected to serum starvation, and then treated with a culture medium containing an FOR inhibitor before extracting the total proteins. Herein, the protein encoded by FGFR2-BICC1 type2, the protein encoded by FGFR2-TXLNA and the protein encoded by FGFR2-KCTD1 are shown in SEQ ID NOs: 6, 2 and 4, respectively.

For the obtained total proteins, the downstream signal of the fusion gene was analyzed by Western blot analysis using various antibodies.

Apparatus:
WesternBreeze chemilumiscent immunodetection kit (Lifetechnologies)
FGFR Inhibitors:
BGJ398 (52183, Selleck Chemicals), stored in 10 mM DMSO solution
PD173074 (S1264, Selleck Chemicals), stored in 10 mM DMSO solution
Compound A (stored in 20 mM DMSO solution)
Antibodies:
FLAG (#635691, Clontech Laboratories, Inc.)
phospho FGFR-Y653/654 (#3476, Cell Signaling Technology Japan, K.K.)
phospho AKT1-S473 (#4060, Cell Signaling Technology Japan, K.K.)
AKT-pan (#4691, Cell Signaling Technology Japan, K.K.)
phospho STAT3-Y705 (#9145, Cell Signaling Technology Japan, K.K.)
STAT3 (#610189, Becton Dickinson and Company)
phospho MAPK-T202/Y204 (#9106, Cell Signaling Technology Japan, K.K.)
MAPK (#4695, Cell Signaling Technology Japan, K.K.)
beta-actin (#A5441, Sigma-Aldrich Co. LLC).
Antibody Array:
PathScan RTK signaling antibody array (Chemiluminescent Readout) (#7982, Cell Signaling Technology Japan, K.K.)

Figure 2:
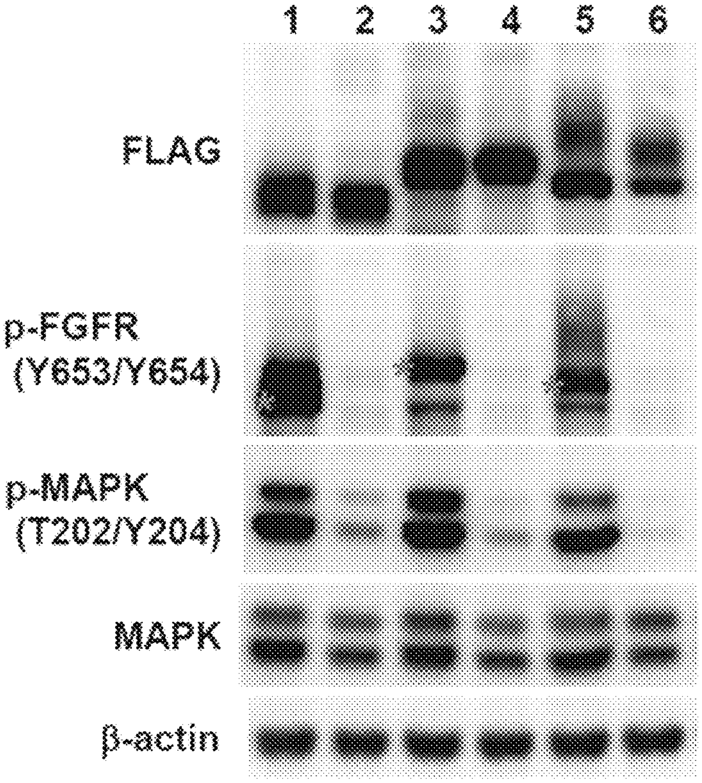
FIG. 2 is a diagram showing the results of Western blot analysis of proteins obtained by culturing mouse fibroblast cell line NIH3T3 transfected with various FGFR2 fusion genes.

The obtained results are shown in FIG. 2. As shown in FIG. 2, it was found that the phosphorylation of the MAPK gene (activation of the MAPK gene) occurred depending on the FGFR2 kinase activity. That is, the NIH3T3 cell transfected with the FGFR2 fusion gene had anchorage independent growth capacity. In FIG. 2, "wild" means the wild-type FGFR2 fusion gene, and "KD" means the KD mutant FGFR2 fusion gene.

Next, the NIH3T3 cell line transfected with the FGFR2 fusion gene was subjected to Western blot analysis after adding the FGFR inhibitor to the cell line (the final concentration of the FGFR inhibitor: 0.2 μM or 0.5 μM) and extracting the total proteins similarly.

Figure 3:
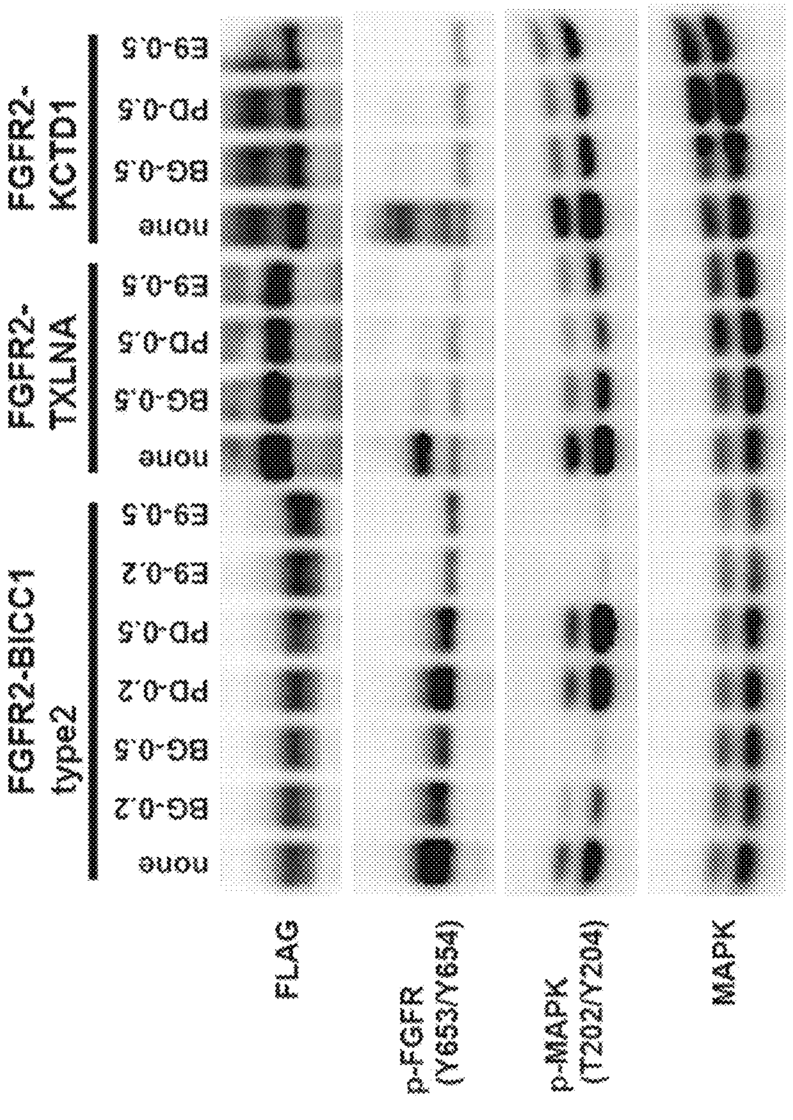
FIG. 3 is a diagram showing the results of Western blot analysis of proteins obtained by culturing NIH3T3 cell line transfected with FGFR2 fusion genes.

The obtained results are shown in FIG. 3. As shown in FIG. 3, by treatment with the FGFR inhibitor, phosphorylation of FGFR was suppressed, and the phosphorylation of MAPK was significantly suppressed. In FIG. 3, "BG" refers to BGJ398, "PD" refers to PD173074, and "E9" refers to Compound A. Specifically, for example, "BG-0.2" means that BGJ398 was added so that the final concentration was 0.2 μM.

Furthermore, the total proteins were similarly extracted from the NIH3T3 cell line not transfected with the FGFR2 fusion gene and from the NIH3T3 cell line transfected with the FGFR2-BICC1 type2, FGFR2-TXLNA or FGFR2-KCTD1. 90 μg of the total proteins extracted was used to analyze the expressed protein with the PathScan (R) array.

Figure 4:
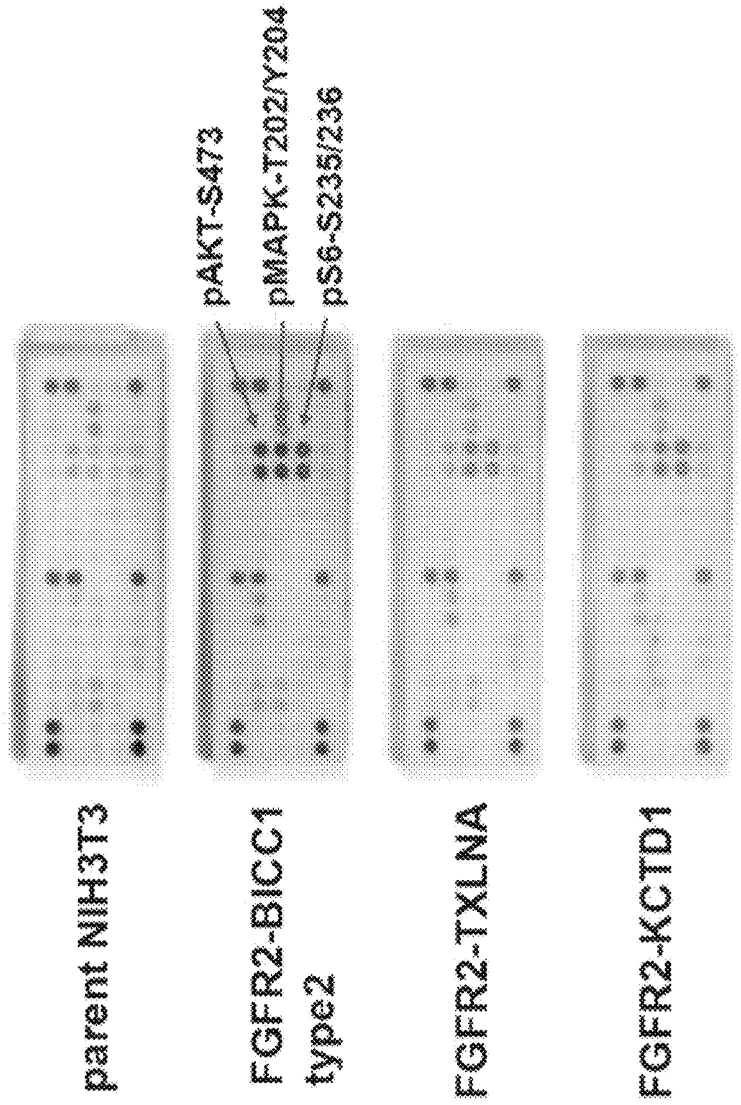
FIG. 4 is a diagram showing the results of analysis of proteins obtained by culturing NIH3T3 cell line transfected with various FGFR2 fusion genes.

As shown in FIG. 4, the phosphorylated Akt (pAkt-S473), phosphorylated MAPK (pMAPK-T202/Y204) and phosphorylated S6 ribosomal protein (pS6-5235/236) were detected.

Test Example 2: Colony Formation Assay

Using the following apparatus, the activity of FGFR inhibitors on the transformation capacity of FGFR2 fusion polypeptide was evaluated. That is, the NIH3T3 cell line transfected with the FGFR2 fusion gene was seeded in a soft agar culture medium (the concentration of agar in the culture medium: 4 mg/mL), and an FGFR inhibitor was added to the culture medium (the final concentration of the FGFR inhibitor: 0.2 μM), and the anchorage independent colony forming capacity was evaluated.

Apparatus:
CytoSelect 96-Well Cell Transformation Assay kit (CBA-130, CellBiolabs)
FGFR Inhibitors:
BGJ398 (S2183, Selleck Chemicals), stored in 10 mM DMSO solution
PD173074 (S1264, Selleck Chemicals), stored in 10 mM DMSO solution
Compound A (stored in 20 mM DMSO solution)

Figure 5:
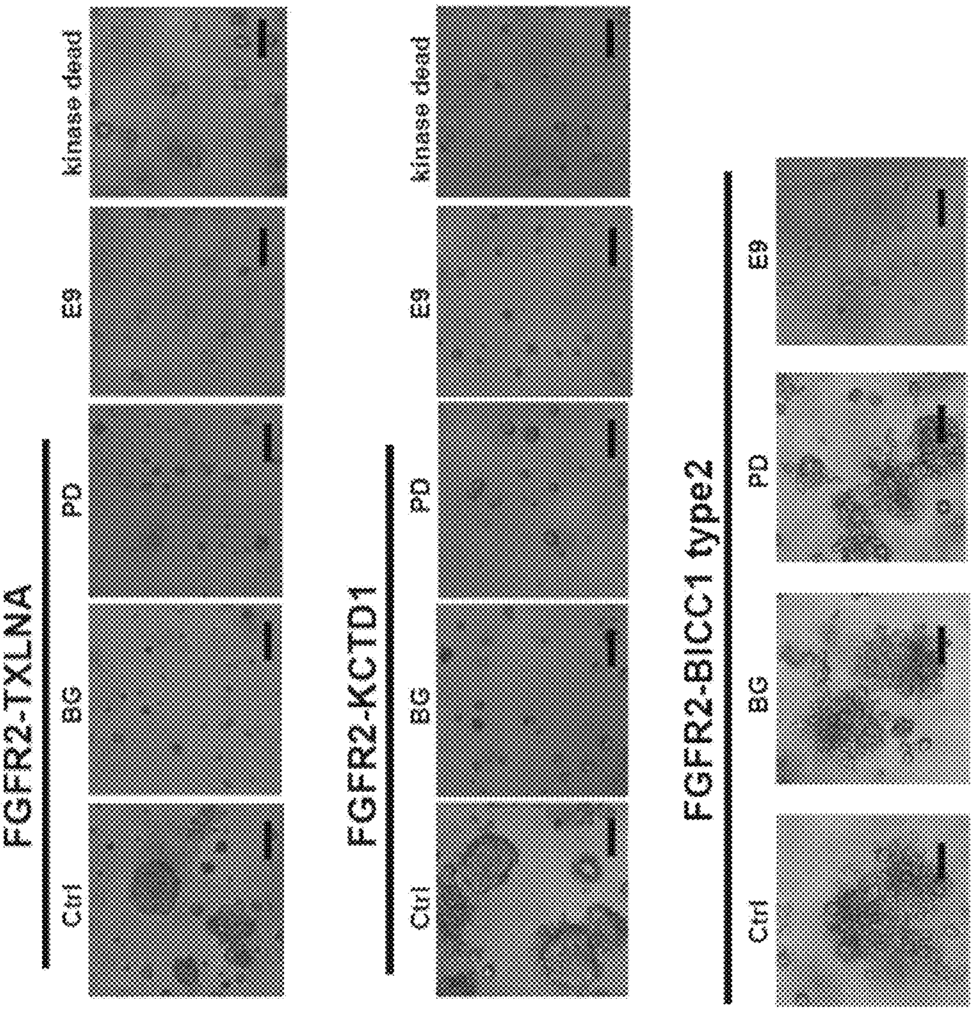
FIG. 5 is a diagram showing the activity of FGFR inhibitors on the growth capacity of NIH3T3 cell line transfected with FGFR2 fusion genes.
Figure 6:
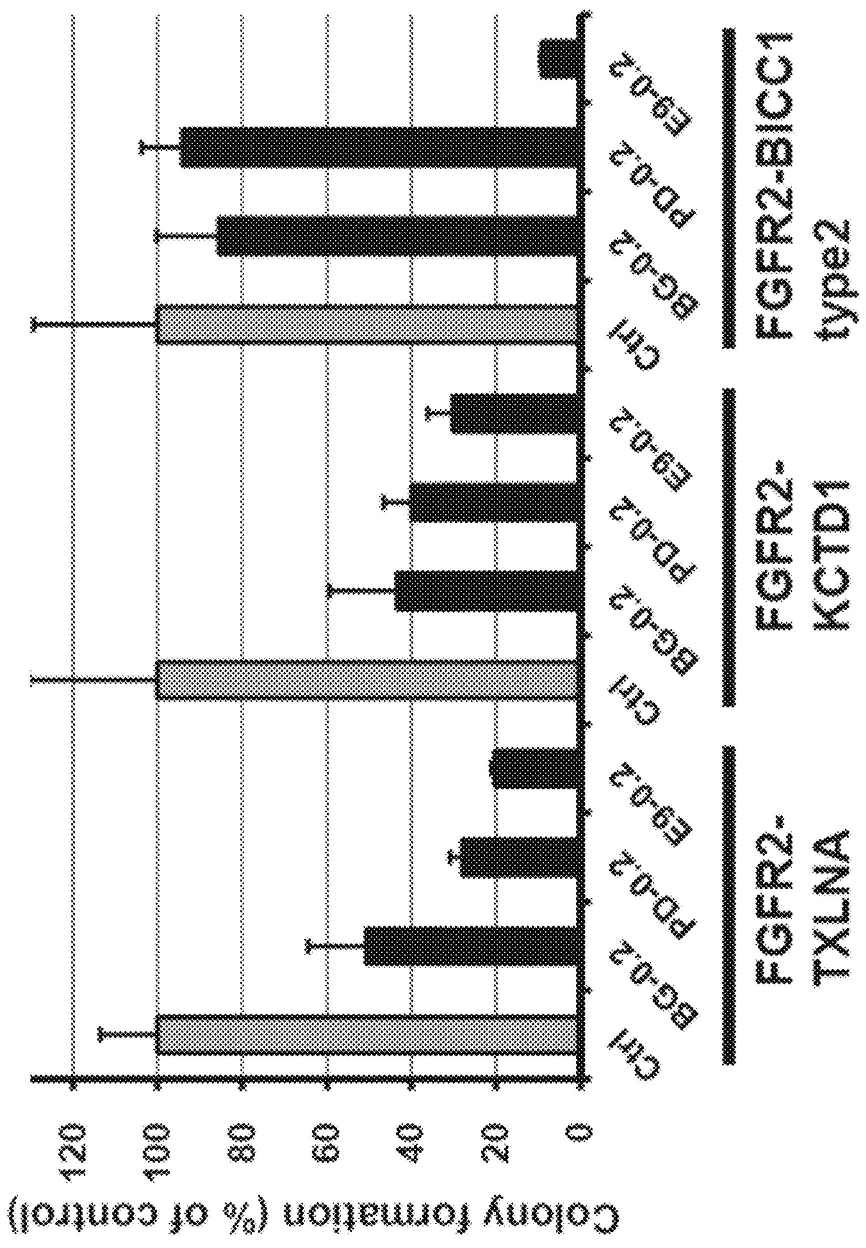
FIG. 6 is a graph showing the activity of FGFR inhibitors on the growth capacity of NIH3T3 cell line transfected with FGFR2 fusion genes.

The obtained results are shown in FIG. 5 and FIG. 6. As shown in FIG. 5 and FIG. 6, among the FGFR2 fusion genes, the anchorage independent growth of the NIH3T3 cells transfected with the FGFR2-TXLNA and FGFR2-KCTD1 was significantly suppressed by the addition of the FGFR inhibitor. On the other hand, the anchorage independent growth of the NIH3T3 cell transfected with FGFR2-BICC1 type2 was little suppressed when using BGJ398 or PD173074 as an FGFR inhibitor, while it was significantly suppressed when using Compound A as an FGFR inhibitor. In FIG. 5 and FIG. 6, "BG" refers to BGJ398, "PD" refers to PD173074, and "E9" refers to Compound A.

Figure 7:
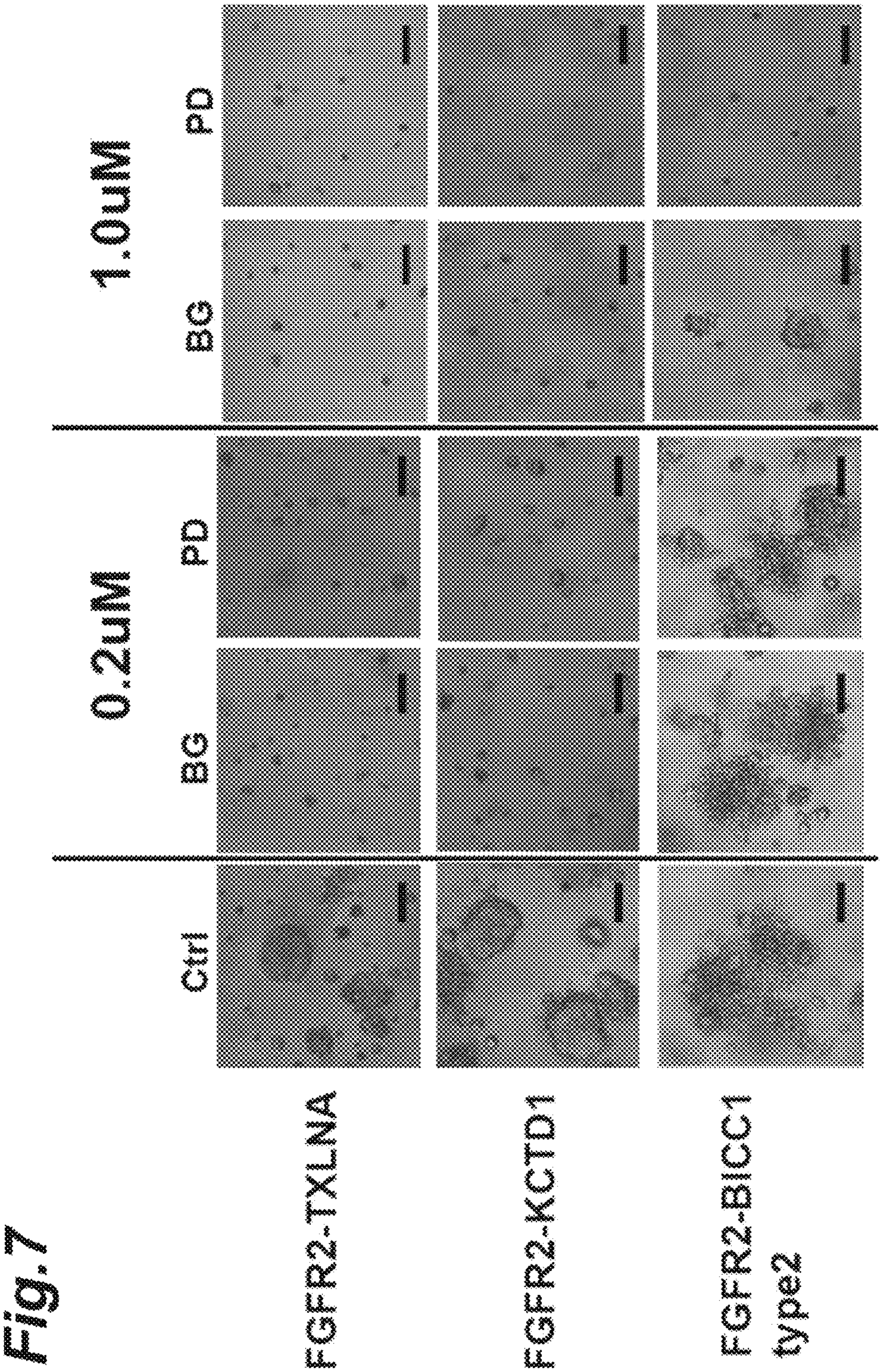
FIG. 7 is a diagram showing the activity of FGFR inhibitors on the growth capacity of NIH3T3 cell line transfected with FGFR2 fusion genes.

As shown in FIG. 7, when BGJ398 or PD173074 was increased so that the final concentration was 1.0 μM, the anchorage independent growth was suppressed. In FIG. 7, "BG" refers to BGJ398, and "PD" refers to PD173074.

Test Example 3: Calculation of $IC_{50}$ Values by Colony Formation Assay

Various NIH3T3 cell lines transfected with the FGFR2 fusion gene were cultured and maintained with D-MEM (Wako Pure Chemical Industries) culture medium containing 10% FBS and penicillin/streptomycin (Wako Pure Chemical Industries) in a 5% $CO_2$ incubator (37° C.). To each well of a 96-well plate (Sumitomo Bakelite) was added 50 μL of D-MEM medium (SIGMA) (containing 10% FBS and penicillin/streptomycin) containing 0.66% agar culture medium (DIFCO Agar Noble, Japan Becton Dickinson). The cell suspension prepared so that the cell number was $4\times10^4$ cells/mL (prepared so that the cell number of FGFR2-TXLNA expressing cells was $8\times10^4$ cells/mL) was mixed with 0.66% agar medium solution in equal amounts, and the layers of 50 μL each of the resulting mixture were piled up and set by cooling at 4° C. for about 30 minutes. After returning the plate to room temperature, layers of 50 μL each of 0.66% agar medium solution were further piled up. 50 μL of Compound A diluted with DMEM culture medium containing 10% FBS was added to each well, and cultured in the 5% $CO_2$ incubator (37° C.) for 14 days. 10 μL of cytometry kit (Cell Counting Kit-8, DOJINDO LABORATORIES) was added to each well and cultured in the 5% $CO_2$ incubator (37° C.) for 1 to 2 hours to result in color development. Absorbance at 450 nm was measured by a multi-label reader (ARVO, PerkinElmer, Inc.). The absorbance in the presence of Compound A was determined assuming that the absorbance in the absence of Compound A was 100% and the absorbance of the well free of cells was 0%. The concentration of Compound A necessary to inhibit cell growth by 50% ($IC_{50}$ value) was determined and shown in Table 1.

TABLE 1

| Name of Cell Line | $IC_{50}$ (nM) |
|---|---|
| FGFR2-BICC1 type2 | 17.3 |
| FGFR2-TXLNA | 1.3 |
| FGFR2-KCTD1 | 5.0 |

Test Example 4: Antitumor Activity in Subcutaneously Transplanted Model Mice (1) Preparation of Subcutaneously Transplanted Model Mice The NIH3T3 cell line transfected with each FGFR2 fusion gene (FGFR2-BICC1 type2, FGFR2-KCTD1, FGFR2-TXLNA) was cultured in DMEM culture media containing 10% FBS and penicillin/streptomycin.

D-PBS (−) (Wako Pure Chemical Industries) was added to the obtained culture media so that the cell number was $1\times10^7$ cells/mL to prepare each cell suspension.

100 μL each of these cell suspensions was transplanted subcutaneously in the right flank region of 7-week-old nude mice (strain: BALB/cAJc1-nu/nu, female, CLEA Japan, Inc.) to prepare FGFR2-BICC1 type2 transplant model mice, FGFR2-KCTD1 transplant model mice and FGFR2-TXLNA transplant model mice. Six days after the transplantation, the width and length of the tumor were measured with a digital caliper (trade name: Digimatic™ Caliper, Mitutoyo Corporation). The tumor volume was calculated based on the width and length of the tumor by the following calculation formula.

$$\text{Tumor volume}(mm^3)=\text{length}(mm)\times\text{width}(mm)\times\text{width}(mm)/2$$

(2) Preparation of Compound A solution

Compound A was dissolved in water for injection and stored at 4° C. under protection from light until just before administration. The solution was prepared so that the dosage of Compound A was 6.25, 12.5, 25 and 50 mg/kg when administered to a mouse at a dose of 20 mL/kg.

(3) Administration of Drug Solution

Based on the tumor volume on the first day of administration, the mice were grouped so that mean values of the tumor volume of the groups were nearly equal to each other. The number of mice per group was 5. The Compound A solution was continuously administered orally to the mice in the Compound A administration group once a day at a dosage of 20 mL/kg. On the other hand, only the solvent (water for injection) was similarly administered to the mice in the control group. The Administration was carried out to FGFR2-BICC1 type2 or FGFR2-KCTD1 transplant model mice for 7 days and to FGFR2-TXLNA transplant model mice for 11 days.

On the first day and the last day of the administration, body weight was measured for each mice in the control group and the Compound A administration group. The ratio of the body weight on the last day to the body weight on the first day (relative body weight: RBW) was calculated. When the RBW of the Compound A administration group/the RBW of the control group was 0.9 or more, the dosage was judged as safe. The corresponding dosage was 6.25, 12.5, 25 and 50 mg/kg.

The tumor volume was also measured on the last day of administration. Percentage of the tumor volume of the mice in the Compound A administration group to the tumor volume of the mice in the control group (T/C) (%) was calculated.

The results of T/C (%) in each transplant model mice was shown in Table 2 to Table 4.

TABLE 2

| FGFR2-BICC1 type 2 transplant model mice | |
|---|---|
| Compound A | T/C (%) |
| 6.25 mg/kg | 80* |
| 12.5 mg/kg | 71** |
| 25 mg/kg | 68** |
| 50 mg/kg | 52** |

Statistically significant
*$p < 0.05$
**$p < 0.01$

TABLE 3

| FGFR2-TXLNA transplant model mice | |
|---|---|
| Compound A | T/C (%) |
| 6.25 mg/kg | 54** |
| 12.5 mg/kg | 43** |
| 25 mg/kg | 15** |
| 50 mg/kg | 6** |

Statistically significant
**$p < 0.01$

TABLE 4

| FGFR2-KCTD1 transplant model mice | |
|---|---|
| Compound A | T/C (%) |
| 6.25 mg/kg | 89 |
| 12.5 mg/kg | 56 |
| 25 mg/kg | 39* |
| 50 mg/kg | 19** |

Statistically significant
*p < 0.05
**p < 0.01

The invention claimed is:

1. A method for treating bile duct cancer, comprising administering to a patient in need thereof a pharmacologically effective amount of 5-((2-(4-(1-(2-hydroxyethyl)piperidin-4-yl)benzamide)pyridin-4-yl)oxy)-6-(2-methoxyethoxy)-N-methyl-1H-indole-1-carboxamide or a pharmaceutically acceptable salt thereof, wherein the patient has been confirmed to have a gene encoding FGFR 2-fusion protein before the administration.

2. The method according to claim 1, wherein the gene encoding the FGFR 2-fusion protein is FGFR2-AHCYL1, FGFR2-BICC1 type1, FGFR2-BICC1 type2, FGFR2-TXLNA or FGFR2-KCTD1.

3. The method according to claim 1, wherein the bile duct cancer is intrahepatic bile duct cancer.

4. The method according to claim 2, wherein the bile duct cancer is intrahepatic bile duct cancer.

5. The method according to claim 1, wherein the gene encoding the FGFR 2-fusion protein is FGFR2-AHCYL1.

6. The method according to claim 1, wherein the gene encoding the FGFR 2-fusion protein is FGFR2-BICC1 type 1.

7. The method according to claim 1, wherein the gene encoding the FGFR 2-fusion protein is FGFR2-BICC1 type 2.

8. The method according to claim 1, wherein the gene encoding the FGFR 2-fusion protein is FGFR2-TXLNA.

9. The method according to claim 1, wherein the gene encoding the FGFR 2-fusion protein is FGFR2-KCTD1.

* * * * *

SEQUENCE LISTING

```
<160> NUMBER OF SEQ ID NOS: 14

<210> SEQ ID NO 1
<211> LENGTH: 2832
<212> TYPE: DNA
<213> ORGANISM: Homo sapiens

<400> SEQUENCE: 1

atggtcagct ggggtcgttt catctgcctg gtcgtggtca ccatggcaac cttgtccctg      60

gcccggccct ccttcagttt agttgaggat accacattag agccagaagg agcaccatac     120

tggaccaaca cagaaaagat ggaaaagcgg ctccatgctg tgcctgcggc caacactgtc     180

aagtttcgct gcccagccgg ggggaaccca atgccaacca tgcggtggct gaaaaacggg     240

aaggagttta agcaggagca tcgcattgga ggctacaagg tacgaaacca gcactggagc     300

ctcattatgg aaagtgtggt cccatctgac aagggaaatt atacctgtgt ggtggagaat     360

gaatacgggt ccatcaatca cacgtaccac ctggatgttg tggagcgatc gcctcaccgg     420

cccatcctcc aagccggact gccggcaaat gcctccacag tggtcggagg agacgtagag     480

tttgtctgca aggtttacag tgatgcccag ccccacatcc agtggatcaa gcacgtggaa     540

aagaacggca gtaaatacgg gcccgacggg ctgccctacc tcaaggttct caagcactcg     600

gggataaata gttccaatgc agaagtgctg gctctgttca atgtgaccga ggcggatgct     660

ggggaatata tatgtaaggt ctccaattat atagggcagg ccaaccagtc tgcctggctc     720

actgtcctgc caaaacagca agcgcctgga agagaaaagg agattacagc ttccccagac     780

tacctggaga tagccattta ctgcataggg gtcttcttaa tcgcctgtat ggtggtaaca     840

gtcatcctgt gccgaatgaa gaacacgacc aagaagccag acttcagcag ccagccggct     900

gtgcacaagc tgaccaaacg tatccccctg cggagacagg taacagtttc ggctgagtcc     960

agctcctcca tgaactccaa caccccgctg gtgaggataa caacacgcct ctcttcaacg    1020

gcagacaccc ccatgctggc aggggtctcc gagtatgaac ttccagagga cccaaaatgg    1080

gagtttccaa gagataagct gacactgggc aagcccctgg gagaaggttg ctttgggcaa    1140

gtggtcatgg cggaagcagt gggaattgac aaagacaagc ccaaggaggc ggtcaccgtg    1200

gccgtgaaga tgttgaaaga tgatgccaca gagaaagacc tttctgatct ggtgtcagag    1260

atggagatga tgaagatgat tgggaaacac aagaatatca taaatcttct tggagcctgc    1320

acacaggatg ggcctctcta tgtcatagtt gagtatgcct ctaaaggcaa cctccgagaa    1380

tacctccgag cccggaggcc acccgggatg gagtactcct atgacattaa ccgtgttcct    1440

gaggagcaga tgaccttcaa ggacttggtg tcatgcacct accagctggc cagaggcatg    1500

gagtacttgg cttcccaaaa atgtattcat cgagatttag cagccagaaa tgttttggta    1560
```

-continued

```
acagaaaaca atgtgatgaa aatagcagac tttggactcg ccagagatat caacaatata   1620

gactattaca aaaagaccac caatgggcgg cttccagtca agtggatggc tccagaagcc   1680

ctgtttgata gagtatacac tcatcagagt gatgtctggt ccttcggggt gttaatgtgg   1740

gagatcttca ctttaggggg ctcgccctac ccagggattc ccgtggagga actttttaag   1800

ctgctgaagg aaggacacag aatggataag ccagccaact gcaccaacga actgtacatg   1860

atgatgaggg actgttggca tgcagtgccc tcccagagac caacgttcaa gcagttggta   1920

gaagacttgg atcgaattct cactctcaca accaatgagg aagaaggtgt gcagcgggcc   1980

cgggaggagg aggagaagcg caaggaggtg acctcgcact tccaggtgac actgaatgac   2040

attcagctgc agatggaaca gcacaatgag cgcaactcca agctgcgcca agagaacatg   2100

gagctggctg agaggctcaa gaagctgatt gagcagtatg agctgcgcga ggagcatatc   2160

gacaaagtct tcaaacacaa ggacctacaa cagcagctgg tggatgccaa gctccagcag   2220

gcccaggaga tgctaaagga ggcagaagag cggcaccagc gggagaagga ttttctcctg   2280

aaagaggcag tagagtccca gaggatgtgt gagctgatga agcagcaaga gacccacctg   2340

aagcaacagc ttgccctata cacagagaag tttgaggagt tccagaacac actttccaaa   2400

agcagcgagg tattcaccac attcaagcag gagatggaaa agatgactaa gaagatcaag   2460

aagctggaga aagaaaccac catgtaccgg tcccggtggg agagcagcaa caaggccctg   2520

cttgagatgg ctgaggagaa aacagtccgg gataaagaac tggagggcct gcaggtaaaa   2580

atccaacggc tggagaagct gtgccgggca ctgcagacag agcgcaatga cctgaacaag   2640

agggtacagg acctgagtgc tggtggccag ggctccctca ctgacagtgg ccctgagagg   2700

aggccagagg ggcctggggc tcaagcaccc agctccccca gggtcacaga agcgccttgc   2760

tacccaggag caccgagcac agaagcatca ggccagactg ggcctcaaga gcccacctcc   2820

gccagggcct ag                                                       2832
```

<210> SEQ ID NO 2
<211> LENGTH: 943
<212> TYPE: PRT
<213> ORGANISM: Homo sapiens

<400> SEQUENCE: 2

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140
```

-continued

```
Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys His Ser Gly Ile Asn Ser Ser Asn Ala Glu
        195                 200                 205

Val Leu Ala Leu Phe Asn Val Thr Glu Ala Asp Ala Gly Glu Tyr Ile
    210                 215                 220

Cys Lys Val Ser Asn Tyr Ile Gly Gln Ala Asn Gln Ser Ala Trp Leu
225                 230                 235                 240

Thr Val Leu Pro Lys Gln Gln Ala Pro Gly Arg Glu Lys Glu Ile Thr
                245                 250                 255

Ala Ser Pro Asp Tyr Leu Glu Ile Ala Ile Tyr Cys Ile Gly Val Phe
            260                 265                 270

Leu Ile Ala Cys Met Val Val Thr Val Ile Leu Cys Arg Met Lys Asn
        275                 280                 285

Thr Thr Lys Lys Pro Asp Phe Ser Ser Gln Pro Ala Val His Lys Leu
    290                 295                 300

Thr Lys Arg Ile Pro Leu Arg Arg Gln Val Thr Val Ser Ala Glu Ser
305                 310                 315                 320

Ser Ser Ser Met Asn Ser Asn Thr Pro Leu Val Arg Ile Thr Thr Arg
                325                 330                 335

Leu Ser Ser Thr Ala Asp Thr Pro Met Leu Ala Gly Val Ser Glu Tyr
            340                 345                 350

Glu Leu Pro Glu Asp Pro Lys Trp Glu Phe Pro Arg Asp Lys Leu Thr
        355                 360                 365

Leu Gly Lys Pro Leu Gly Glu Gly Cys Phe Gly Gln Val Val Met Ala
    370                 375                 380

Glu Ala Val Gly Ile Asp Lys Asp Lys Pro Lys Glu Ala Val Thr Val
385                 390                 395                 400

Ala Val Lys Met Leu Lys Asp Asp Ala Thr Glu Lys Asp Leu Ser Asp
                405                 410                 415

Leu Val Ser Glu Met Glu Met Met Lys Met Ile Gly Lys His Lys Asn
            420                 425                 430

Ile Ile Asn Leu Leu Gly Ala Cys Thr Gln Asp Gly Pro Leu Tyr Val
        435                 440                 445

Ile Val Glu Tyr Ala Ser Lys Gly Asn Leu Arg Glu Tyr Leu Arg Ala
    450                 455                 460

Arg Arg Pro Pro Gly Met Glu Tyr Ser Tyr Asp Ile Asn Arg Val Pro
465                 470                 475                 480

Glu Glu Gln Met Thr Phe Lys Asp Leu Val Ser Cys Thr Tyr Gln Leu
                485                 490                 495

Ala Arg Gly Met Glu Tyr Leu Ala Ser Gln Lys Cys Ile His Arg Asp
            500                 505                 510

Leu Ala Ala Arg Asn Val Leu Val Thr Glu Asn Asn Val Met Lys Ile
        515                 520                 525

Ala Asp Phe Gly Leu Ala Arg Asp Ile Asn Asn Ile Asp Tyr Tyr Lys
    530                 535                 540

Lys Thr Thr Asn Gly Arg Leu Pro Val Lys Trp Met Ala Pro Glu Ala
545                 550                 555                 560

Leu Phe Asp Arg Val Tyr Thr His Gln Ser Asp Val Trp Ser Phe Gly
```

-continued

```
                565                 570                 575

Val Leu Met Trp Glu Ile Phe Thr Leu Gly Gly Ser Pro Tyr Pro Gly
            580                 585                 590

Ile Pro Val Glu Glu Leu Phe Lys Leu Leu Lys Glu Gly His Arg Met
        595                 600                 605

Asp Lys Pro Ala Asn Cys Thr Asn Glu Leu Tyr Met Met Met Arg Asp
    610                 615                 620

Cys Trp His Ala Val Pro Ser Gln Arg Pro Thr Phe Lys Gln Leu Val
625                 630                 635                 640

Glu Asp Leu Asp Arg Ile Leu Thr Leu Thr Thr Asn Glu Glu Glu Gly
                645                 650                 655

Val Gln Arg Ala Arg Glu Glu Glu Glu Lys Arg Lys Glu Val Thr Ser
            660                 665                 670

His Phe Gln Val Thr Leu Asn Asp Ile Gln Leu Gln Met Glu Gln His
        675                 680                 685

Asn Glu Arg Asn Ser Lys Leu Arg Gln Glu Asn Met Glu Leu Ala Glu
    690                 695                 700

Arg Leu Lys Lys Leu Ile Glu Gln Tyr Glu Leu Arg Glu Glu His Ile
705                 710                 715                 720

Asp Lys Val Phe Lys His Lys Asp Leu Gln Gln Gln Leu Val Asp Ala
                725                 730                 735

Lys Leu Gln Gln Ala Gln Glu Met Leu Lys Glu Ala Glu Glu Arg His
            740                 745                 750

Gln Arg Glu Lys Asp Phe Leu Leu Lys Glu Ala Val Glu Ser Gln Arg
        755                 760                 765

Met Cys Glu Leu Met Lys Gln Gln Glu Thr His Leu Lys Gln Gln Leu
    770                 775                 780

Ala Leu Tyr Thr Glu Lys Phe Glu Glu Phe Gln Asn Thr Leu Ser Lys
785                 790                 795                 800

Ser Ser Glu Val Phe Thr Thr Phe Lys Gln Glu Met Glu Lys Met Thr
                805                 810                 815

Lys Lys Ile Lys Lys Leu Glu Lys Glu Thr Thr Met Tyr Arg Ser Arg
            820                 825                 830

Trp Glu Ser Ser Asn Lys Ala Leu Leu Glu Met Ala Glu Glu Lys Thr
        835                 840                 845

Val Arg Asp Lys Glu Leu Glu Gly Leu Gln Val Lys Ile Gln Arg Leu
    850                 855                 860

Glu Lys Leu Cys Arg Ala Leu Gln Thr Glu Arg Asn Asp Leu Asn Lys
865                 870                 875                 880

Arg Val Gln Asp Leu Ser Ala Gly Gly Gln Gly Ser Leu Thr Asp Ser
                885                 890                 895

Gly Pro Glu Arg Arg Pro Glu Gly Pro Gly Ala Gln Ala Pro Ser Ser
            900                 905                 910

Pro Arg Val Thr Glu Ala Pro Cys Tyr Pro Gly Ala Pro Ser Thr Glu
        915                 920                 925

Ala Ser Gly Gln Thr Gly Pro Gln Glu Pro Thr Ser Ala Arg Ala
    930                 935                 940
```

<210> SEQ ID NO 3
<211> LENGTH: 2826
<212> TYPE: DNA
<213> ORGANISM: Homo sapiens

<400> SEQUENCE: 3

-continued

```
atggtcagct ggggtcgttt catctgcctg gtcgtggtca ccatggcaac cttgtccctg     60
gcccggccct ccttcagttt agttgaggat accacattag agccagaaga tgccatctca    120
tccggagatg atgaggatga caccgatggt gcggaagatt ttgtcagtga gaacagtaac    180
aacaagagag caccatactg gaccaacaca gaaaagatgg aaaagcggct ccatgctgtg    240
cctgcggcca acactgtcaa gtttcgctgc ccagccgggg ggaacccaat gccaaccatg    300
cggtggctga aaaacgggaa ggagtttaag caggagcatc gcattggagg ctacaaggta    360
cgaaaccagc actggagcct cattatggaa agtgtggtcc catctgacaa gggaaattat    420
acctgtgtgg tggagaatga atacgggtcc atcaatcaca cgtaccacct ggatgttgtg    480
gagcgatcgc ctcaccggcc catcctccaa gccggactgc cggcaaatgc ctccacagtg    540
gtcggaggag acgtagagtt tgtctgcaag gtttacagtg atgcccagcc ccacatccag    600
tggatcaagc acgtggaaaa gaacggcagt aaatacgggc ccgacgggct gccctacctc    660
aaggttctca agcactcggg gataaatagt tccaatgcag aagtgctggc tctgttcaat    720
gtgaccgagg cggatgctgg ggaatatata tgtaaggtct ccaattatat agggcaggcc    780
aaccagtctg cctggctcac tgtcctgcca aaacagcaag cgcctggaag agaaaaggag    840
attacagctt ccccagacta cctggagata gccatttact gcatagggggt cttcttaatc    900
gcctgtatgg tggtaacagt catcctgtgc cgaatgaaga acacgaccaa gaagccagac    960
ttcagcagcc agccggctgt gcacaagctg accaaacgta tccccctgcg gagacaggta   1020
acagtttcgg ctgagtccag ctcctccatg aactccaaca ccccgctggt gaggataaca   1080
acacgcctct cttcaacggc agacaccccc atgctggcag gggtctccga gtatgagctt   1140
ccagaggacc caaaatggga gtttccaaga gataagctga cactgggcaa gcccctggga   1200
gaaggttgct ttgggcaagt ggtcatggcg gaagcagtgg gaattgacaa agacaagccc   1260
aaggaggcgg tcaccgtggc cgtgaagatg ttgaaagatg atgccacaga gaaagacctt   1320
tctgatctgg tgtcagagat ggagatgatg aagatgattg ggaaacacaa gaatatcata   1380
aatcttcttg gagcctgcac acaggatggg cctctctatg tcatagttga gtatgcctct   1440
aaaggcaacc tccgagaata cctccgagcc cggaggccac ccgggatgga gtactcctat   1500
gacattaacc gtgttcctga ggagcagatg accttcaagg acttggtgtc atgcacctac   1560
cagctggcca gaggcatgga gtacttggct tcccaaaaat gtattcatcg agatttagca   1620
gccagaaatg ttttggtaac agaaaacaat gtgatgaaaa tagcagactt tggactcgcc   1680
agagatatca acaatataga ctattacaaa aagaccacca atgggcggct tccagtcaag   1740
tggatggctc cagaagccct gtttgataga gtatacactc atcagagtga tgtctggtcc   1800
ttcggggtgt taatgtggga gatcttcact ttagggggct cgccctaccc agggattccc   1860
gtggaggaac tttttaagct gctgaaggaa ggacacagaa tggataagcc agccaactgc   1920
accaacgaac tgtacatgat gatgagggac tgttggcatg cagtgccctc ccagagacca   1980
acgttcaagc agttggtaga agacttggat cgaattctca ctctcacaac caatgaggac   2040
agtcggccca atatgtcaag acctctgatc actagatccc ctgcatctcc actgaacaac   2100
caaggcatcc ctactccagc acaactcaca aaatccaatg cgcctgtcca cattgatgtg   2160
ggcggccaca tgtacaccag cagcctggcc accctcacca aataccctga atccagaatc   2220
ggaagacttt ttgatggtac agagcccatt gttttggaca gtctcaaaca gcactatttc   2280
attgacagag atggacagat gttcagatat atcttgaatt ttctacgaac atccaaactc   2340
ctcattcctg atgatttcaa ggactacact ttgttatatg aagaggcaaa atattttcag   2400
```

-continued

```
cttcagccca tgttgttgga gatggaaaga tggaagcagg acagagaaac tggtcgattt   2460

tcaaggccct gtgagtgcct cgtcgtgcgt gtggccccag acctcggaga aaggatcacg   2520

ctaagcggtg acaaatcctt gatagaagaa gtatttccag agatcggcga cgtgatgtgt   2580

aactctgtca atgcaggctg gaatcacgac tcgacgcacg tcatcaggtt tccactaaat   2640

ggctactgtc acctcaactc agtccaggtc ctcgagaggt tgcagcaaag aggatttgaa   2700

atcgtgggct cctgtggggg aggagtagac tcgtcccagt tcagcgaata cgtccttcgg   2760

cgggaactga ggcggacgcc ccgtgtaccc tccgtcatcc ggataaagca agagcctctg   2820

gactaa                                                              2826

<210> SEQ ID NO 4
<211> LENGTH: 941
<212> TYPE: PRT
<213> ORGANISM: Homo sapiens

<400> SEQUENCE: 4

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

His Ser Gly Ile Asn Ser Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
            260                 265                 270

Gln Ala Pro Gly Arg Glu Lys Glu Ile Thr Ala Ser Pro Asp Tyr Leu
        275                 280                 285
```

-continued

```
Glu Ile Ala Ile Tyr Cys Ile Gly Val Phe Leu Ile Ala Cys Met Val
    290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Thr Val Ser Ala Glu Ser Ser Ser Ser Met Asn Ser
            340                 345                 350

Asn Thr Pro Leu Val Arg Ile Thr Thr Arg Leu Ser Ser Thr Ala Asp
        355                 360                 365

Thr Pro Met Leu Ala Gly Val Ser Glu Tyr Glu Leu Pro Glu Asp Pro
    370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
            420                 425                 430

Asp Asp Ala Thr Glu Lys Asp Leu Ser Asp Leu Val Ser Glu Met Glu
        435                 440                 445

Met Met Lys Met Ile Gly Lys His Lys Asn Ile Ile Asn Leu Leu Gly
    450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
            500                 505                 510

Lys Asp Leu Val Ser Cys Thr Tyr Gln Leu Ala Arg Gly Met Glu Tyr
        515                 520                 525

Leu Ala Ser Gln Lys Cys Ile His Arg Asp Leu Ala Ala Arg Asn Val
    530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Lys Thr Thr Asn Gly Arg
                565                 570                 575

Leu Pro Val Lys Trp Met Ala Pro Glu Ala Leu Phe Asp Arg Val Tyr
            580                 585                 590

Thr His Gln Ser Asp Val Trp Ser Phe Gly Val Leu Met Trp Glu Ile
        595                 600                 605

Phe Thr Leu Gly Gly Ser Pro Tyr Pro Gly Ile Pro Val Glu Glu Leu
    610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
                645                 650                 655

Ser Gln Arg Pro Thr Phe Lys Gln Leu Val Glu Asp Leu Asp Arg Ile
            660                 665                 670

Leu Thr Leu Thr Thr Asn Glu Asp Ser Arg Pro Asn Met Ser Arg Pro
        675                 680                 685

Leu Ile Thr Arg Ser Pro Ala Ser Pro Leu Asn Asn Gln Gly Ile Pro
    690                 695                 700

Thr Pro Ala Gln Leu Thr Lys Ser Asn Ala Pro Val His Ile Asp Val
```

-continued

```
705                 710                 715                 720

Gly Gly His Met Tyr Thr Ser Ser Leu Ala Thr Leu Thr Lys Tyr Pro
                725                 730                 735

Glu Ser Arg Ile Gly Arg Leu Phe Asp Gly Thr Glu Pro Ile Val Leu
            740                 745                 750

Asp Ser Leu Lys Gln His Tyr Phe Ile Asp Arg Asp Gly Gln Met Phe
        755                 760                 765

Arg Tyr Ile Leu Asn Phe Leu Arg Thr Ser Lys Leu Leu Ile Pro Asp
    770                 775                 780

Asp Phe Lys Asp Tyr Thr Leu Leu Tyr Glu Glu Ala Lys Tyr Phe Gln
785                 790                 795                 800

Leu Gln Pro Met Leu Leu Glu Met Glu Arg Trp Lys Gln Asp Arg Glu
                805                 810                 815

Thr Gly Arg Phe Ser Arg Pro Cys Glu Cys Leu Val Val Arg Val Ala
            820                 825                 830

Pro Asp Leu Gly Glu Arg Ile Thr Leu Ser Gly Asp Lys Ser Leu Ile
        835                 840                 845

Glu Glu Val Phe Pro Glu Ile Gly Asp Val Met Cys Asn Ser Val Asn
    850                 855                 860

Ala Gly Trp Asn His Asp Ser Thr His Val Ile Arg Phe Pro Leu Asn
865                 870                 875                 880

Gly Tyr Cys His Leu Asn Ser Val Gln Val Leu Glu Arg Leu Gln Gln
                885                 890                 895

Arg Gly Phe Glu Ile Val Gly Ser Cys Gly Gly Gly Val Asp Ser Ser
            900                 905                 910

Gln Phe Ser Glu Tyr Val Leu Arg Arg Glu Leu Arg Arg Thr Pro Arg
        915                 920                 925

Val Pro Ser Val Ile Arg Ile Lys Gln Glu Pro Leu Asp
    930                 935                 940


<210> SEQ ID NO 5
<211> LENGTH: 2508
<212> TYPE: DNA
<213> ORGANISM: Homo sapiens

<400> SEQUENCE: 5

atggtcagct ggggtcgttt catctgcctg gtcgtggtca ccatggcaac cttgtccctg      60

gcccggccct ccttcagttt agttgaggat accacattag agccagaagg agcaccatac     120

tggaccaaca cagaaaagat ggaaaagcgg ctccatgctg tgcctgcggc caacactgtc     180

aagtttcgct gcccagccgg ggggaaccca atgccaacca tgcggtggct gaaaaacggg     240

aaggagttta agcaggagca tcgcattgga ggctacaagg tacgaaacca gcactggagc     300

ctcattatgg aaagtgtggt cccatctgac aagggaaatt atacctgtgt ggtggagaat     360

gaatacgggt ccatcaatca cacgtaccac ctggatgttg tggagcgatc gcctcaccgg     420

cccatcctcc aagccggact gccggcaaat gcctccacag tggtcggagg agacgtagag     480

tttgtctgca aggtttacag tgatgcccag ccccacatcc agtggatcaa gcacgtggaa     540

aagaacggca gtaaatacgg gcccgacggg ctgccctacc tcaaggttct caagcactcg     600

gggataaata gttccaatgc agaagtgctg gctctgttca atgtgaccga ggcggatgct     660

ggggaatata tatgtaaggt ctccaattat atagggcagg ccaaccagtc tgcctggctc     720

actgtcctgc caaaacagca agcgcctgga agagaaaagg agattacagc ttccccagac     780

tacctggaga tagccattta ctgcataggg gtcttcttaa tcgcctgtat ggtggtaaca     840
```

-continued

```
gtcatcctgt gccgaatgaa gaacacgacc aagaagccag acttcagcag ccagccggct    900
gtgcacaagc tgaccaaacg tatccccctg cggagacagg taacagtttc ggctgagtcc    960
agctcctcca tgaactccaa caccccgctg gtgaggataa caacacgcct ctcttcaacg   1020
gcagacaccc ccatgctggc aggggtctcc gagtatgaac ttccagagga cccaaaatgg   1080
gagtttccaa gagataagct gacactgggc aagcccctgg gagaaggttg ctttgggcaa   1140
gtggtcatgg cggaagcagt gggaattgac aaagacaagc ccaaggaggc ggtcaccgtg   1200
gccgtgaaga tgttgaaaga tgatgccaca gagaaagacc tttctgatct ggtgtcagag   1260
atggagatga tgaagatgat tggggaaacac aagaatatca taaatcttct tggagcctgc   1320
acacaggatg ggcctctcta tgtcatagtt gagtatgcct ctaaaggcaa cctccgagaa   1380
tacctccgag cccggaggcc acccgggatg gagtactcct atgacattaa ccgtgttcct   1440
gaggagcaga tgaccttcaa ggacttggtg tcatgcacct accagctggc cagaggcatg   1500
gagtacttgg cttcccaaaa atgtattcat cgagatttag cagccagaaa tgttttggta   1560
acagaaaaca atgtgatgaa aatagcagac tttggactcg ccagagatat caacaatata   1620
gactattaca aaaagaccac caatgggcgg cttccagtca agtggatggc tccagaagcc   1680
ctgtttgata gagtatacac tcatcagagt gatgtctggt ccttcggggt gttaatgtgg   1740
gagatcttca ctttaggggg ctcgccctac ccagggattc ccgtggagga actttttaag   1800
ctgctgaagg aaggacacag aatggataag ccagccaact gcaccaacga actgtacatg   1860
atgatgaggg actgttggca tgcagtgccc tcccagagac caacgttcaa gcagttggta   1920
gaagacttgg atcgaattct cactctcaca accaatgagg gctcatccat gtccctttca   1980
cggtccaaca gtcgtgagca cttgggaggt ggaagcgaat ctgataactg gagagaccga   2040
aatggaattg gacctggaag tcatagtgaa tttgcagctt ctattggcag ccctaagcgt   2100
aaacaaaaca aatcaacgga acactatctc agcagtagca attacatgga ctgcatttcc   2160
tcgctgacag gaagcaatgg ctgtaactta aatagctctt tcaaaggttc tgacctccct   2220
gagctcttca gcaaactggg cctgggcaaa tacacagatg ttttccagca acaagagatc   2280
gatcttcaga cattcctcac tctcacagat caggatctga aggagctggg aataactact   2340
tttggtgcca ggaggaaaat gctgcttgca atttcagaac taaataaaaa ccgaagaaag   2400
ctttttgaat cgccaaatgc acgcacctct ttcctggaag gtggagcgag tggaaggcta   2460
ccccgtcagt atcactcaga cattgctagt gtcagtggcc gctggtag                2508
```

<210> SEQ ID NO 6
<211> LENGTH: 835
<212> TYPE: PRT
<213> ORGANISM: Homo sapiens

<400> SEQUENCE: 6

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80
```

-continued

```
Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys His Ser Gly Ile Asn Ser Ser Asn Ala Glu
        195                 200                 205

Val Leu Ala Leu Phe Asn Val Thr Glu Ala Asp Ala Gly Glu Tyr Ile
    210                 215                 220

Cys Lys Val Ser Asn Tyr Ile Gly Gln Ala Asn Gln Ser Ala Trp Leu
225                 230                 235                 240

Thr Val Leu Pro Lys Gln Gln Ala Pro Gly Arg Glu Lys Glu Ile Thr
                245                 250                 255

Ala Ser Pro Asp Tyr Leu Glu Ile Ala Ile Tyr Cys Ile Gly Val Phe
            260                 265                 270

Leu Ile Ala Cys Met Val Val Thr Val Ile Leu Cys Arg Met Lys Asn
        275                 280                 285

Thr Thr Lys Lys Pro Asp Phe Ser Ser Gln Pro Ala Val His Lys Leu
    290                 295                 300

Thr Lys Arg Ile Pro Leu Arg Arg Gln Val Thr Val Ser Ala Glu Ser
305                 310                 315                 320

Ser Ser Ser Met Asn Ser Asn Thr Pro Leu Val Arg Ile Thr Thr Arg
                325                 330                 335

Leu Ser Ser Thr Ala Asp Thr Pro Met Leu Ala Gly Val Ser Glu Tyr
            340                 345                 350

Glu Leu Pro Glu Asp Pro Lys Trp Glu Phe Pro Arg Asp Lys Leu Thr
        355                 360                 365

Leu Gly Lys Pro Leu Gly Glu Gly Cys Phe Gly Gln Val Val Met Ala
    370                 375                 380

Glu Ala Val Gly Ile Asp Lys Asp Lys Pro Lys Glu Ala Val Thr Val
385                 390                 395                 400

Ala Val Lys Met Leu Lys Asp Asp Ala Thr Glu Lys Asp Leu Ser Asp
                405                 410                 415

Leu Val Ser Glu Met Glu Met Met Lys Met Ile Gly Lys His Lys Asn
            420                 425                 430

Ile Ile Asn Leu Leu Gly Ala Cys Thr Gln Asp Gly Pro Leu Tyr Val
        435                 440                 445

Ile Val Glu Tyr Ala Ser Lys Gly Asn Leu Arg Glu Tyr Leu Arg Ala
    450                 455                 460

Arg Arg Pro Pro Gly Met Glu Tyr Ser Tyr Asp Ile Asn Arg Val Pro
465                 470                 475                 480

Glu Glu Gln Met Thr Phe Lys Asp Leu Val Ser Cys Thr Tyr Gln Leu
                485                 490                 495
```

-continued

```
Ala Arg Gly Met Glu Tyr Leu Ala Ser Gln Lys Cys Ile His Arg Asp
            500                 505                 510

Leu Ala Ala Arg Asn Val Leu Val Thr Glu Asn Asn Val Met Lys Ile
        515                 520                 525

Ala Asp Phe Gly Leu Ala Arg Asp Ile Asn Asn Ile Asp Tyr Tyr Lys
    530                 535                 540

Lys Thr Thr Asn Gly Arg Leu Pro Val Lys Trp Met Ala Pro Glu Ala
545                 550                 555                 560

Leu Phe Asp Arg Val Tyr Thr His Gln Ser Asp Val Trp Ser Phe Gly
                565                 570                 575

Val Leu Met Trp Glu Ile Phe Thr Leu Gly Gly Ser Pro Tyr Pro Gly
            580                 585                 590

Ile Pro Val Glu Glu Leu Phe Lys Leu Leu Lys Glu Gly His Arg Met
        595                 600                 605

Asp Lys Pro Ala Asn Cys Thr Asn Glu Leu Tyr Met Met Met Arg Asp
    610                 615                 620

Cys Trp His Ala Val Pro Ser Gln Arg Pro Thr Phe Lys Gln Leu Val
625                 630                 635                 640

Glu Asp Leu Asp Arg Ile Leu Thr Leu Thr Thr Asn Glu Gly Ser Ser
                645                 650                 655

Met Ser Leu Ser Arg Ser Asn Ser Arg Glu His Leu Gly Gly Gly Ser
            660                 665                 670

Glu Ser Asp Asn Trp Arg Asp Arg Asn Gly Ile Gly Pro Gly Ser His
        675                 680                 685

Ser Glu Phe Ala Ala Ser Ile Gly Ser Pro Lys Arg Lys Gln Asn Lys
    690                 695                 700

Ser Thr Glu His Tyr Leu Ser Ser Ser Asn Tyr Met Asp Cys Ile Ser
705                 710                 715                 720

Ser Leu Thr Gly Ser Asn Gly Cys Asn Leu Asn Ser Ser Phe Lys Gly
                725                 730                 735

Ser Asp Leu Pro Glu Leu Phe Ser Lys Leu Gly Leu Gly Lys Tyr Thr
            740                 745                 750

Asp Val Phe Gln Gln Gln Glu Ile Asp Leu Gln Thr Phe Leu Thr Leu
        755                 760                 765

Thr Asp Gln Asp Leu Lys Glu Leu Gly Ile Thr Thr Phe Gly Ala Arg
    770                 775                 780

Arg Lys Met Leu Leu Ala Ile Ser Glu Leu Asn Lys Asn Arg Arg Lys
785                 790                 795                 800

Leu Phe Glu Ser Pro Asn Ala Arg Thr Ser Phe Leu Glu Gly Gly Ala
                805                 810                 815

Ser Gly Arg Leu Pro Arg Gln Tyr His Ser Asp Ile Ala Ser Val Ser
            820                 825                 830

Gly Arg Trp
        835


<210> SEQ ID NO 7
<211> LENGTH: 4657
<212> TYPE: DNA
<213> ORGANISM: Homo sapiens

<400> SEQUENCE: 7

ggcggcggct ggaggagagc gcggtggaga gccgagcggg cgggcggcgg gtgcggagcg      60

ggcgagggag cgcgcgcggc cgccacaaag ctcgggcgcc gcggggctgc atgcggcgta     120

cctggcccgg cgcggcgact gctctccggg ctggcggggg ccggccgcga gccccggggg     180
```

-continued

```
ccccgaggcc gcagcttgcc tgcgcgctct gagccttcgc aactcgcgag caaagtttgg    240
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc ggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaagcact cggggataaa tagttccaat gcagaagtgc   1620
tggctctgtt caatgtgacc gaggcggatg ctggggaata tatatgtaag gtctccaatt   1680
atatagggca ggccaaccag tctgcctggc tcactgtcct gccaaaacag caagcgcctg   1740
gaagagaaaa ggagattaca gcttccccag actacctgga gatagccatt tactgcatag   1800
gggtcttctt aatcgcctgt atggtggtaa cagtcatcct gtgccgaatg aagaacacga   1860
ccaagaagcc agacttcagc agccagccgg ctgtgcacaa gctgaccaaa cgtatccccc   1920
tgcggagaca ggtaacagtt tcggctgagt ccagctcctc catgaactcc aacaccccgc   1980
tggtgaggat aacaacacgc ctctcttcaa cggcagacac ccccatgctg gcaggggtct   2040
ccgagtatga acttccagag gacccaaaat gggagtttcc aagagataag ctgacactgg   2100
gcaagcccct gggagaaggt tgctttgggc aagtggtcat ggcggaagca gtgggaattg   2160
acaaagacaa gcccaaggag gcggtcaccg tggccgtgaa gatgttgaaa gatgatgcca   2220
cagagaaaga cctttctgat ctggtgtcag agatggagat gatgaagatg attgggaaac   2280
acaagaatat cataaatctt cttggagcct gcacacagga tgggcctctc tatgtcatag   2340
ttgagtatgc ctctaaaggc aacctccgag aatacctccg agcccggagg ccacccggga   2400
tggagtactc ctatgacatt aaccgtgttc ctgaggagca gatgaccttc aaggacttgg   2460
tgtcatgcac ctaccagctg gccagaggca tggagtactt ggcttcccaa aaatgtattc   2520
```

```
atcgagattt agcagccaga aatgttttgg taacagaaaa caatgtgatg aaaatagcag   2580
actttggact cgccagagat atcaacaata tagactatta caaaaagacc accaatgggc   2640
ggcttccagt caagtggatg gctccagaag ccctgtttga tagagtatac actcatcaga   2700
gtgatgtctg gtccttcggg gtgttaatgt gggagatctt cactttaggg ggctcgccct   2760
acccagggat tcccgtggag gaacttttta agctgctgaa ggaaggacac agaatggata   2820
agccagccaa ctgcaccaac gaactgtaca tgatgatgag ggactgttgg catgcagtgc   2880
cctcccagag accaacgttc aagcagttgg tagaagactt ggatcgaatt ctcactctca   2940
caaccaatga ggaatacttg gacctcagcc aacctctcga acagtattca cctagttacc   3000
ctgacacaag aagttcttgt tcttcaggag atgattctgt tttttctcca gaccccatgc   3060
cttacgaacc atgccttcct cagtatccac acataaacgg cagtgttaaa acatgaatga   3120
ctgtgtctgc ctgtccccaa acaggacagc actgggaacc tagctacact gagcagggag   3180
accatgcctc ccagagcttg ttgtctccac ttgtatatat ggatcagagg agtaaataat   3240
tggaaaagta atcagcatat gtgtaaagat ttatacagtt gaaaacttgt aatcttcccc   3300
aggaggagaa gaaggtttct ggagcagtgg actgccacaa gccaccatgt aacccctctc   3360
acctgccgtg cgtactggct gtggaccagt aggactcaag gtggacgtgc gttctgcctt   3420
ccttgttaat tttgtaataa ttggagaaga tttatgtcag cacacactta cagagcacaa   3480
atgcagtata taggtgctgg atgtatgtaa atatattcaa attatgtata aatatatatt   3540
atatatttac aaggagttat tttttgtatt gattttaaat ggatgtccca atgcacctag   3600
aaaattggtc tctctttttt taatagctat ttgctaaatg ctgttcttac acataatttc   3660
ttaattttca ccgagcagag gtggaaaaat actttttgctt tcagggaaaa tggtataacg   3720
ttaatttatt aataaattgg taatatacaa aacaattaat catttatagt ttttttgta    3780
atttaagtgg catttctatg caggcagcac agcagactag ttaatctatt gcttggactt   3840
aactagttat cagatccttt gaaaagagaa tatttacaat atatgactaa tttggggaaa   3900
atgaagtttt gatttatttg tgtttaaatg ctgctgtcag acgattgttc ttagacctcc   3960
taaatgcccc atattaaaag aactcattca taggaaggtg tttcattttg gtgtgcaacc   4020
ctgtcattac gtcaacgcaa cgtctaactg gacttcccaa gataaatggt accagcgtcc   4080
tcttaaaaga tgccttaatc cattccttga ggacagacct tagttgaaat gatagcagaa   4140
tgtgcttctc tctggcagct ggccttctgc ttctgagttg cacattaatc agattagcct   4200
gtattctctt cagtgaattt tgataatggc ttccagactc tttggcgttg gagacgcctg   4260
ttaggatctt caagtcccat catagaaaat tgaaacacag agttgttctg ctgatagttt   4320
tggggatacg tccatctttt taagggattg ctttcatcta attctggcag gacctcacca   4380
aaagatccag cctcatacct acatcagaca aaatatcgcc gttgttcctt ctgtactaaa   4440
gtattgtgtt ttgctttgga aacacccact cactttgcaa tagccgtgca agatgaatgc   4500
agattacact gatcttatgt gttacaaaat tggagaaagt atttaataaa acctgttaat   4560
ttttatactg acaataaaaa tgtttctaca gatattaatg ttaacaagac aaaataaatg   4620
tcacgcaact tattttttta ataaaaaaaa aaaaaaa                            4657
```

<210> SEQ ID NO 8
<211> LENGTH: 822
<212> TYPE: PRT
<213> ORGANISM: Homo sapiens

<400> SEQUENCE: 8

-continued

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415
```

-continued

```
His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820
```

-continued

<210> SEQ ID NO 9
<211> LENGTH: 1706
<212> TYPE: DNA
<213> ORGANISM: Homo sapiens

<400> SEQUENCE: 9
gaggtgggga agccatcgga cgtcggcggt gaggatcttc tcctgaccca gcatcgctca 60
tcacaatgaa gaaccaagac aaaaagaacg gggctgccaa acaatccaat ccaaaaagca 120
gcccaggaca accggaagca ggacccgagg gagcccagga gcggcccagc caggcggctc 180
ctgcagtaga agcagaaggt cccggcagca gccaggctcc tcggaagccg gagggggctc 240
aagccagaac ggctcagtct ggggcccttc gtgatgtctc tgaggagctg agccgccaac 300
tggaagacat actgagcaca tactgtgtgg acaataacca gggggccccc ggcgaggatg 360
gggcacaggg tgagccggct gaacccgaag atgcagagaa gtcccggacc tatgtggcaa 420
ggaatgggga gcctgaacca actccagtag tcaatggaga gaaggaaccc tccaaggggg 480
atccaaacac agaagagatc cggcagagtg acgaggtcgg agaccgagac catcgaaggc 540
cacaggagaa gaaaaaagcc aagggtttgg ggaaggagat cacgttgctg atgcagacat 600
tgaatactct gagtacccca gaggagaagc tggctgctct gtgcaagaag tatgctgaac 660
tgctggagga gcaccggaat tcacagaagc agatgaagct cctacagaaa aagcagagcc 720
agctggtgca agagaaggac cacctgcgcg gtgagcacag caaggccgtc ctggcccgca 780
gcaagcttga gagcctatgc cgtgagctgc agcggcacaa ccgctccctc aaggaagaag 840
gtgtgcagcg ggcccgggag gaggaggaga agcgcaagga ggtgacctcg cacttccagg 900
tgacactgaa tgacattcag ctgcagatgg aacagcacaa tgagcgcaac tccaagctgc 960
gccaagagaa catggagctg gctgagaggc tcaagaagct gattgagcag tatgagctgc 1020
gcgaggagca tatcgacaaa gtcttcaaac acaaggacct acaacagcag ctggtggatg 1080
ccaagctcca gcaggcccag gagatgctaa aggaggcaga agagcggcac cagcgggaga 1140
aggattttct cctgaaagag gcagtagagt cccagaggat gtgtgagctg atgaagcagc 1200
aagagaccca cctgaagcaa cagcttgccc tatacacaga gaagtttgag gagttccaga 1260
acacactttc caaaagcagc gaggtattca ccacattcaa gcaggagatg gaaaagatga 1320
ctaagaagat caagaagctg gagaaagaaa ccaccatgta ccggtcccgg tgggagagca 1380
gcaacaaggc cctgcttgag atggctgagg agaaaacagt ccgggataaa gaactggagg 1440
gcctgcaggt aaaaatccaa cggctggaga agctgtgccg ggcactgcag acagagcgca 1500
atgacctgaa caagagggta caggacctga gtgctggtgg ccagggctcc ctcactgaca 1560
gtggccctga gaggaggcca gaggggcctg gggctcaagc acccagctcc cccagggtca 1620
cagaagcgcc ttgctaccca ggagcaccga gcacagaagc atcaggccag actgggcctc 1680
aagagcccac ctccgccagg gcctag 1706

<210> SEQ ID NO 10
<211> LENGTH: 546
<212> TYPE: PRT
<213> ORGANISM: Homo sapiens

<400> SEQUENCE: 10

Met Lys Asn Gln Asp Lys Lys Asn Gly Ala Ala Lys Gln Ser Asn Pro
1               5                   10                  15

Lys Ser Ser Pro Gly Gln Pro Glu Ala Gly Pro Glu Gly Ala Gln Glu
            20                  25                  30

-continued

```
Arg Pro Ser Gln Ala Ala Pro Ala Val Glu Ala Glu Gly Pro Gly Ser
        35                  40                  45

Ser Gln Ala Pro Arg Lys Pro Glu Gly Ala Gln Ala Arg Thr Ala Gln
    50                  55                  60

Ser Gly Ala Leu Arg Asp Val Ser Glu Glu Leu Ser Arg Gln Leu Glu
65                  70                  75                  80

Asp Ile Leu Ser Thr Tyr Cys Val Asp Asn Asn Gln Gly Gly Pro Gly
                85                  90                  95

Glu Asp Gly Ala Gln Gly Glu Pro Ala Glu Pro Glu Asp Ala Glu Lys
            100                 105                 110

Ser Arg Thr Tyr Val Ala Arg Asn Gly Glu Pro Glu Pro Thr Pro Val
        115                 120                 125

Val Asn Gly Glu Lys Glu Pro Ser Lys Gly Asp Pro Asn Thr Glu Glu
    130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Glu Lys Arg Lys Glu
            260                 265                 270

Val Thr Ser His Phe Gln Val Thr Leu Asn Asp Ile Gln Leu Gln Met
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350

Glu Arg His Gln Arg Glu Lys Asp Phe Leu Leu Lys Glu Ala Val Glu
        355                 360                 365

Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
            420                 425                 430

Arg Ser Arg Trp Glu Ser Ser Asn Lys Ala Leu Leu Glu Met Ala Glu
        435                 440                 445

Glu Lys Thr Val Arg Asp Lys Glu Leu Glu Gly Leu Gln Val Lys Ile
```

-continued

```
    450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Ser Leu
                485                 490                 495

Thr Asp Ser Gly Pro Glu Arg Arg Pro Glu Gly Pro Gly Ala Gln Ala
            500                 505                 510

Pro Ser Ser Pro Arg Val Thr Glu Ala Pro Cys Tyr Pro Gly Ala Pro
        515                 520                 525

Ser Thr Glu Ala Ser Gly Gln Thr Gly Pro Gln Glu Pro Thr Ser Ala
    530                 535                 540

Arg Ala
545


<210> SEQ ID NO 11
<211> LENGTH: 3431
<212> TYPE: DNA
<213> ORGANISM: Homo sapiens

<400> SEQUENCE: 11

atggcgagaa tgcctggcag cggggactgt aacaccagcg cgggcggcag cgccagcgct      60

gccgccgccg ccgccgagaa caatggggag cggggcgagg gcgagcgcgg cgcgggggc     120

cgcggccgcc gccacagccg tccgcactac tgcagcgcgg gcgaggagga ggaggaagag    180

gaggaggagg acgagatcca ggaggtgcag ataacggggg acgaggagga ggaggaggac    240

ggaggtgggg ggctggagga ggacgaggag gaggaggaag aggaggagat ggggctggac    300

tgggacgagc ccctggagcc cgaggactcg gccggggagg agctggagcc cgagccggtc    360

catatgatca atatggacca gagcgccgcg ctggagcccg aggcgccgcc gcgactgctg    420

gcgccccggg cccgcggtgg gccgcccggg gacggctccg agctggaccc cgacgtgctg    480

cagcgccccg agcgggcccg gctgagcgag aacacccggc tggccacccg ctacgccgtg    540

cgcatcttcc gggagtacct gagcgagaag gcgcagagcc cggacttcga gaccatggac    600

aagggggcgc tgtgccgcgt gctgcgctcc ttctatgccg aggcccgctc caaaagcggc    660

cagctctaca gcaagtcgtc gctcatcagc atccgcagct ccctcaaccg ctacctcaat    720

gagcccccgt actgccgcac gctcgacctc accaaggacc ccgagctgcg cagcgccaac    780

ctgacgctgg ccgcggtcat ccgcaagctc gaggagcagg gcgccgggcc ggtggtgcag    840

aagcaagcca tcacgcgcgc cgacctgcgc aagctgtaca cctccagcgt cttcagcacc    900

aacacgccct tcgggctgct caacaaggtc tggttcgaga cgtgcatgta cttctgtacc    960

cgcggccgcg agaaccagcg tgagttggag gaggactctt ttgggctggc catggacgag   1020

gacggtcgca agttcgtcta cttcaagtcc ctcgggccct accacaagtc gcgctcgtcg   1080

tcgtggagca agaagcgcgc cgagagcagc gacgaggaga acttgccccg catgtatgag   1140

acgggcaccg agttctgccc ctacgccagc ttcgtcaagt acctgtcgaa acgcaaccct   1200

ctctgcaagg cgttcttcca gcggccccgg gaccactgca gcgagggcga tgtgacctgg   1260

tacgagaaca aagccatcgg caagaacttg ctaggcactc ggatgcagat gctctccaag   1320

gcggccaagc tctccaagac ctacaccaac cactgcatcg gcgccgtctc catcgccacg   1380

ctcaacagca tcgcgggcat tggcaccaag ctgggctcgc ccgccccgca gggctgctac   1440

gccgaggctc tgaacggggc ggcacggcac cactcccacc acccccccac ccatccctcc   1500

caccaccacc gcccccagcc gccctcgctg ggaacactt acatcctccc caaagacagc     1560
```

caggtcgggc ccgacgtgaa atccgaggct gcgcccaagc gcgccctgta cgagtctgtg 1620
ttcgggtcgg gggaaatctg cggccccact tcccccaaaa gactttgtat ccgcccctcg 1680
gagcctgtgg atgcggtggt ggtggtttcc gtgaaacacg accccctgcc tcttcttcca 1740
gaagccaatg ggcacagaag caccaattct cccacaatag tttcacctgc tattgtttcc 1800
cccacccagg acagtcggcc caatatgtca agacctctga tcactagatc ccctgcatct 1860
ccactgaaca accaaggcat ccctactcca gcacaactca caaaatccaa tgcgcctgtc 1920
cacattgatg tgggcggcca catgtacacc agcagcctgg ccaccctcac caaataccct 1980
gaatccagaa tcggaagact tttgatggt acagagccca ttgttttgga cagtctcaaa 2040
cagcactatt tcattgacag agatggacag atgttcagat atatcttgaa ttttctacga 2100
acatccaaac tcctcattcc tgatgatttc aaggactaca ctttgttata tgaagaggca 2160
aaatattttc agcttcagcc catgttgttg gagatggaaa gatggaagca ggacagagaa 2220
actggtcgat tttcaaggcc ctgtgagtgc ctcgtcgtgc gtgtggcccc agacctcgga 2280
gaaaggatca cgctaagcgg tgacaaatcc ttgatagaag aagtatttcc agagatcggc 2340
gacgtgatgt gtaactctgt caatgcaggc tggaatcacg actcgacgca cgtcatcagg 2400
tttccactaa atggctactg tcacctcaac tcagtccagg tcctcgagag gttgcagcaa 2460
agaggatttg aaatcgtggg ctcctgtggg ggaggagtag actcgtccca gttcagcgaa 2520
tacgtccttc ggcgggaact gaggcggacg ccccgtgtac cctccgtcat ccggataaag 2580
caagagcctc tggactaaat ggacatattt cttatgcaaa aaggaaaaca cacacaacca 2640
ataactcaaa caaaaaaggg acatttatgt gcagttggga cagcaaacca agtcctggac 2700
gtaaaatcga ataaaagaca catttatatc caatagagac cacacctgta ttcatatggg 2760
aacaattgga atagtgatat cctcaaggtg taaaaaatat ataaatatat atatatatgt 2820
caaaaggtag gaaatgcaaa aaagaaaaaa aaaaaaggtg acagccgcag ttggtgctgt 2880
gatggccgtg aagtgtcctg ggccttccga ggcctctgac aaataaacaa gccatgagtg 2940
gtgaggacac agtctcctta cagtttccat tgccaacaac agccatccat atttcttttt 3000
tcctttgtct ttctttttcc ttttttttta aaaaaacaaa acaaacaaaa caccttgaat 3060
caagtttgtt tgtatatgga ggttccacgt ctttctttag gcagggacca ggcaggactt 3120
cagaaaaacc ctcatgagca cattgcaaag atgttagaca tgaaatttta aatgtagttt 3180
gtacagaagt cacacttttt tgtccacctc acagatgtga actttacttt gttttaaaac 3240
tgatcagttt tgccaagggg ccagaattat tccttgttag aattgctcca gttcaagtct 3300
gctgctttcc tacaattttt caaattttat aatgtattaa atacaataaa ctctgtttaa 3360
aaaataaggt ctgtgtgaaa cacacatgtg ggggtgaggc tggattaaag tgaaattttt 3420
tctttttgaa a 3431

<210> SEQ ID NO 12
<211> LENGTH: 865
<212> TYPE: PRT
<213> ORGANISM: Homo sapiens

<400> SEQUENCE: 12

Met Ala Arg Met Pro Gly Ser Gly Asp Cys Asn Thr Ser Ala Gly Gly
1 5 10 15

Ser Ala Ser Ala Ala Ala Ala Ala Ala Glu Asn Asn Gly Glu Arg Gly
20 25 30

-continued

```
Glu Gly Glu Arg Gly Ala Gly Gly Arg Gly Arg Arg His Ser Arg Pro
        35                  40                  45

His Tyr Cys Ser Ala Gly Glu Glu Glu Glu Glu Glu Glu Glu Glu Asp
    50                  55                  60

Glu Ile Gln Glu Val Gln Ile Thr Gly Asp Glu Glu Glu Glu Glu Asp
65                  70                  75                  80

Gly Gly Gly Gly Leu Glu Glu Asp Glu Glu Glu Glu Glu Glu Glu Glu
                85                  90                  95

Met Gly Leu Asp Trp Asp Glu Pro Leu Glu Pro Glu Asp Ser Ala Gly
            100                 105                 110

Glu Glu Leu Glu Pro Glu Pro Val His Met Ile Asn Met Asp Gln Ser
        115                 120                 125

Ala Ala Leu Glu Pro Glu Ala Pro Pro Arg Leu Leu Ala Pro Arg Ala
    130                 135                 140

Arg Gly Gly Pro Pro Gly Asp Gly Ser Glu Leu Asp Pro Asp Val Leu
145                 150                 155                 160

Gln Arg Pro Glu Arg Ala Arg Leu Ser Glu Asn Thr Arg Leu Ala Thr
                165                 170                 175

Arg Tyr Ala Val Arg Ile Phe Arg Glu Tyr Leu Ser Glu Lys Ala Gln
            180                 185                 190

Ser Pro Asp Phe Glu Thr Met Asp Lys Gly Ala Leu Cys Arg Val Leu
        195                 200                 205

Arg Ser Phe Tyr Ala Glu Ala Arg Ser Lys Ser Gly Gln Leu Tyr Ser
    210                 215                 220

Lys Ser Ser Leu Ile Ser Ile Arg Ser Ser Leu Asn Arg Tyr Leu Asn
225                 230                 235                 240

Glu Pro Pro Tyr Cys Arg Thr Leu Asp Leu Thr Lys Asp Pro Glu Leu
                245                 250                 255

Arg Ser Ala Asn Leu Thr Leu Ala Ala Val Ile Arg Lys Leu Glu Glu
            260                 265                 270

Gln Gly Ala Gly Pro Val Val Gln Lys Gln Ala Ile Thr Arg Ala Asp
        275                 280                 285

Leu Arg Lys Leu Tyr Thr Ser Ser Val Phe Ser Thr Asn Thr Pro Phe
    290                 295                 300

Gly Leu Leu Asn Lys Val Trp Phe Glu Thr Cys Met Tyr Phe Cys Thr
305                 310                 315                 320

Arg Gly Arg Glu Asn Gln Arg Glu Leu Glu Glu Asp Ser Phe Gly Leu
                325                 330                 335

Ala Met Asp Glu Asp Gly Arg Lys Phe Val Tyr Phe Lys Ser Leu Gly
            340                 345                 350

Pro Tyr His Lys Ser Arg Ser Ser Ser Trp Ser Lys Lys Arg Ala Glu
        355                 360                 365

Ser Ser Asp Glu Glu Asn Leu Pro Arg Met Tyr Glu Thr Gly Thr Glu
    370                 375                 380

Phe Cys Pro Tyr Ala Ser Phe Val Lys Tyr Leu Ser Lys Arg Asn Pro
385                 390                 395                 400

Leu Cys Lys Ala Phe Phe Gln Arg Pro Arg Asp His Cys Ser Glu Gly
                405                 410                 415

Asp Val Thr Trp Tyr Glu Asn Lys Ala Ile Gly Lys Asn Leu Leu Gly
            420                 425                 430

Thr Arg Met Gln Met Leu Ser Lys Ala Ala Lys Leu Ser Lys Thr Tyr
        435                 440                 445

Thr Asn His Cys Ile Gly Ala Val Ser Ile Ala Thr Leu Asn Ser Ile
```

-continued

```
    450                 455                 460

Ala Gly Ile Gly Thr Lys Leu Gly Ser Pro Ala Pro Gln Gly Cys Tyr
465                 470                 475                 480

Ala Glu Ala Leu Asn Gly Ala Ala Arg His His Ser His His Pro Pro
                485                 490                 495

Thr His Pro Ser His His His Arg Pro Gln Pro Pro Ser Leu Gly Asn
            500                 505                 510

Thr Tyr Ile Leu Pro Lys Asp Ser Gln Val Gly Pro Asp Val Lys Ser
        515                 520                 525

Glu Ala Ala Pro Lys Arg Ala Leu Tyr Glu Ser Val Phe Gly Ser Gly
    530                 535                 540

Glu Ile Cys Gly Pro Thr Ser Pro Lys Arg Leu Cys Ile Arg Pro Ser
545                 550                 555                 560

Glu Pro Val Asp Ala Val Val Val Val Ser Val Lys His Asp Pro Leu
                565                 570                 575

Pro Leu Leu Pro Glu Ala Asn Gly His Arg Ser Thr Asn Ser Pro Thr
            580                 585                 590

Ile Val Ser Pro Ala Ile Val Ser Pro Thr Gln Asp Ser Arg Pro Asn
        595                 600                 605

Met Ser Arg Pro Leu Ile Thr Arg Ser Pro Ala Ser Pro Leu Asn Asn
    610                 615                 620

Gln Gly Ile Pro Thr Pro Ala Gln Leu Thr Lys Ser Asn Ala Pro Val
625                 630                 635                 640

His Ile Asp Val Gly Gly His Met Tyr Thr Ser Ser Leu Ala Thr Leu
                645                 650                 655

Thr Lys Tyr Pro Glu Ser Arg Ile Gly Arg Leu Phe Asp Gly Thr Glu
            660                 665                 670

Pro Ile Val Leu Asp Ser Leu Lys Gln His Tyr Phe Ile Asp Arg Asp
        675                 680                 685

Gly Gln Met Phe Arg Tyr Ile Leu Asn Phe Leu Arg Thr Ser Lys Leu
    690                 695                 700

Leu Ile Pro Asp Asp Phe Lys Asp Tyr Thr Leu Leu Tyr Glu Glu Ala
705                 710                 715                 720

Lys Tyr Phe Gln Leu Gln Pro Met Leu Leu Glu Met Glu Arg Trp Lys
                725                 730                 735

Gln Asp Arg Glu Thr Gly Arg Phe Ser Arg Pro Cys Glu Cys Leu Val
            740                 745                 750

Val Arg Val Ala Pro Asp Leu Gly Glu Arg Ile Thr Leu Ser Gly Asp
        755                 760                 765

Lys Ser Leu Ile Glu Glu Val Phe Pro Glu Ile Gly Asp Val Met Cys
    770                 775                 780

Asn Ser Val Asn Ala Gly Trp Asn His Asp Ser Thr His Val Ile Arg
785                 790                 795                 800

Phe Pro Leu Asn Gly Tyr Cys His Leu Asn Ser Val Gln Val Leu Glu
                805                 810                 815

Arg Leu Gln Gln Arg Gly Phe Glu Ile Val Gly Ser Cys Gly Gly Gly
            820                 825                 830

Val Asp Ser Ser Gln Phe Ser Glu Tyr Val Leu Arg Arg Glu Leu Arg
        835                 840                 845

Arg Thr Pro Arg Val Pro Ser Val Ile Arg Ile Lys Gln Glu Pro Leu
    850                 855                 860

Asp
865
```

<210> SEQ ID NO 13
<211> LENGTH: 5486
<212> TYPE: DNA
<213> ORGANISM: Homo sapiens

<400> SEQUENCE: 13
atggccgccc agggagagcc cggctacctg gcggcgcagt cggaccccgg ctccaacagc 60
gagcgcagca ccgactcccc agtgcccggc tccgaggacg acttggtcgc cggggcgacc 120
ctgcacagcc cggagtggag cgaggagcgc ttccgcgtgg acaggaagaa acttgaggcc 180
atgttacaag ctgctgctga agggaaaggc agaagtgggg aagacttttt tcaaaagatc 240
atggaggaaa caaatacgca gattgcttgg ccatcaaaac tgaagatcgg agccaaatcc 300
aagaaagatc cccatattaa ggtttctgga aagaaagaag atgttaaaga agccaaggaa 360
atgatcatgt ctgtcttaga cacaaaaagc aatcgagtca cactgaagat ggatgtttca 420
catacagaac attcacatgt aatcggcaaa ggtggcaaca atattaaaaa agtgatggaa 480
gaaaccggat gccatatcca ctttccagat tccaacagga ataaccaagc agaaaaaagc 540
aaccaggtat ctatagcggg acaaccagca ggagtagaat ctgcccgagt tagaattcgg 600
gagctgcttc ctttggtgct gatgtttgag ctaccaattg ctggaattct tcaaccggtt 660
cctgatccta attccccctc tattcagcat atatcacaaa cgtacaatat ttcagtatca 720
tttaaacagc gttcccgaat gtatggtgct actgtcatag tacgagggtc tcagaataac 780
actagtgctg tgaaggaagg aactgccatg ctgttagaac atcttgctgg gagcttagca 840
tcagctattc ctgtgagcac acaactagat attgcagctc aacatcatct ctttatgatg 900
ggtcgaaatg ggagcaacat caaacatatc atgcagagaa caggtgctca gatccacttt 960
cctgatccca gtaatccaca aaagaaatct accgtctacc tccagggcac cattgagtct 1020
gtctgtcttg caaggcaata tctcatgggt tgtcttcctc ttgtgttgat gtttgatatg 1080
aaggaagaaa ttgaagtaga tccacaattc attgcgcagt tgatggaaca gcttgatgtc 1140
ttcatcagta ttaaaccaaa gcccaaacag ccaagcaagt ctgtgattgt gaaaagtgtt 1200
gagcgaaatg ccttaaatat gtatgaagca aggaaatgtc tcctcggact tgaaagcagt 1260
ggggttacca tagcaaccag tccatcccca gcatcctgcc ctgccggcct ggcatgtccc 1320
agcctggata tcttagcttc agcaggcctt ggactcactg gactaggtct tttgggaccc 1380
accaccttat ctctgaacac ttcaacaacc ccaaactcac tcttgaatgc tcttaatagc 1440
tcagtcagtc ctttgcaaag tccaagttct ggtacaccca gccccacatt atgggcaccc 1500
ccacttgcta atacttcaag tgccacaggt ttttctgcta taccacacct tatgattcca 1560
tctactgccc aagccacatt aactaatatt ttgttgtctg gagtgcccac ctatgggcac 1620
acagctccat ctcccccctcc tggcttgact cctgttgatg tccatatcaa cagtatgcag 1680
accgaaggca aaaaaatctc tgctgcttta aatggacatg cacagtctcc agatataaaa 1740
tatggtgcaa tatccacttc atcacttgga gaaaaagtgc tgagtgcaaa tcacggggat 1800
ccgtccatcc agacaagtgg gtctgagcag acatctccca aatcaagccc cactgaaggt 1860
tgtaatgatg cttttgttga agtaggcatg cctcgaagtc cttcccattc tgggaatgct 1920
ggtgacttga aacagatgat gtgtccctcc aaggtttcct gtgccaaaag gcagacagtg 1980
gaactattgc aaggcacgaa aaactcacac ttacacagca ctgacaggtt gctctcagac 2040
cctgaactga gtgctaccga aagccctttg gctgacaaga aggctccagg gagtgagcgc 2100

-continued gctgcagaga gggcagcagc tgcccagcaa aactccgaaa gggcccacct tgctccacgg 2160
tcatcatatg tcaacatgca ggcatttgac tatgaacaga agaagctatt agccaccaaa 2220
gctatgttaa agaaaccagt ggtgacggag gtcagaacgc ccacaaatac ctggagtggc 2280
ctgggttttt ctaaatccat gccagctgaa actatcaagg agttgagaag ggccaatcat 2340
gtgtcctata agcccacaat gacaaccact tatgagggct catccatgtc cctttcacgg 2400
tccaacagtc gtgagcactt gggaggtgga agcgaatctg ataactggag agaccgaaat 2460
ggaattggac ctggaagtca tagtgaattt gcagcttcta ttggcagccc taagcgtaaa 2520
caaaacaaat caacggaaca ctatctcagc agtagcaatt acatggactg catttcctcg 2580
ctgacaggaa gcaatggctg taacttaaat agctctttca aaggttctga cctccctgag 2640
ctcttcagca aactgggcct gggcaaatac acagatgttt tccagcaaca agagatcgat 2700
cttcagacat tcctcactct cacagatcag gatctgaagg agctgggaat aactactttt 2760
ggtgccagga ggaaaatgct gcttgcaatt tcagaactaa ataaaaaccg aagaaagctt 2820
tttgaatcgc caaatgcacg cacctctttc ctggaaggtg gagcgagtgg aaggctaccc 2880
cgtcagtatc actcagacat tgctagtgtc agtggccgct ggtagcagca ccctcttggc 2940
acatgcccgc tgactaactg taaagtggac acaggagatg tatgaacagc cttcacagca 3000
caccatcctt agcactctgg gtgtctggta tcaggaccaa agcattttat tcgcacctgt 3060
actttatggc aaaaaggaag aagagagaga agatgttctt atgatgtcat acagaacacc 3120
aaatatggat tacttttta aaatggcagt tggacagaat ttgcaatata aggatagggc 3180
tttatttcct gtttttattt acctatataa catatgcact gatgattttt ttttttttt 3240
ttttttttt ttttttactt aaaatgaagg atgaattgac atctgggatg ccagaagact 3300
tagaagttat tttgtttgct tgttttgttt gggtatttgg ggatttttaa aaaataatca 3360
aagtggaatt ttctggtact gctttaaaat aattattgtg gtctttcagc actttacacg 3420
ttctaatttc ttgtcctatg gaagttctcg ctgtctccat ctctctcatt tttgtgtcac 3480
ctaatatgtt ggtacagata agagttagtc acatttttct gactgcatca aacttttatt 3540
tgaaatggta ctggatctta gtttctgtgc agaatattct gtgattttgg gaaatgtaag 3600
tgagtccact tgcttctgga ccaattctgt ttcatgtatg ttagcatcct agaaacacct 3660
agcaatggac ctagttcaca gtaataggtg caaagaaaga ccaaatggac tttgcagtat 3720
taaccctttg cagtcgtcat acttagctgc tgcctgtaat gctaaaatga ttttaatggt 3780
tgtctggagg caaagggctg ttttttagta tattgccact aaaggacatt tatttatatc 3840
aaacttttat ttttagatat tataagcata cagtacataa ttgatgaaat tgatatttac 3900
tagagattta tggtagagaa tggacgacat tcaataactg gagcccgaga ttgtcacttt 3960
atttaaaaag acaaataatc atctgacaag acagcactgt tgccattata aggagaaata 4020
gattacaatc cttatcatgt acacgttagc tatgttccgt atggccacag gactttcctg 4080
aaaccgtatc tgtctgcttg aagtagactt atgtttgttg agaatgaaca ggcttatttg 4140
agcctccagg gtggcagttc ataaagacag ctaagttctg aaggaaaaaa aaaatatatc 4200
tttttaagtg gctagagtca ttattacaat cttatactgt gaaagtccaa gaaatcaggc 4260
aacattgttt cctgggtctt ttcagagatc ttatagattt atgaagtgtt tttaatccat 4320
gaagaaacac taaagtgcct ttctttcttc aaagcaatat tatttccaag tatattaatt 4380
tgttagaaaa ctttcccata ggaaatgttg tcaagttacc tgtactgtaa agagttattt 4440
atgttcagta gtcaagattt tctacatgga cataaaccac tctcacgtgc tctcagcaga 4500

-continued

```
aggcattaga taagcatata caagaattgg gtacttttat acaaatatgg gataagaaat   4560

acttgcctga cacttttcca tggctgagtc tgaccattac agtaagaaca agaattgaag   4620

aggcattttg cacacagaaa cattctcact ttaaaaaatg gtattggtta ccttgaaggc   4680

atagataatg ggcctgtcat aaaattatca attataactg gcaccgaggg actgcccttt   4740

ttaagctaaa ctaagcctta tctgcttaag gatgttgaac tgaatcactc cctttactca   4800

tcctgtgcat atgtgtacaa atggtcatgt ggatcatgtg atgatcatcc atcttatttg   4860

attgtattaa tgcatcatgc taaacatgta gtacaggtta acaataccag atttatgtcc   4920

tgttcaacaa ctcagtactc taaatgttgt tatgctttta ataagacctt cccagataat   4980

aatcttggag ctcttttccc agctgtctac catgcatttg caacaggagg aagatgtaat   5040

gaatatgcag tattaagttg atttatgaac agtgctttga tatgccaaag ggaaaactgt   5100

cccacttaaa ttagattaag tagggtggct aaaaataaat aaaaacactg gaaattcttt   5160

ctctcacttt ctcttgatgc aatgaaggga atatgacact acagtataca gagttgttgt   5220

tatatgatgc acaaaatatt ttgatgattt gaataaatgt taacttttaa tctgcgcctt   5280

aataatgact ggttatctgt aaatatagaa cagatacaga ttgtattttt ctgtgggttt   5340

ttgtcctttt agtgattttt ttccaaaaac gagagatgga attaacattg aaaatgggaa   5400

atttttctaa ctgaatcaat tgttacatga aaaataaatt tatataaccc ctttgtattg   5460

ctcttgctat aaaaaaaaaa aaaaaa                                         5486
```

<210> SEQ ID NO 14
<211> LENGTH: 974
<212> TYPE: PRT
<213> ORGANISM: Homo sapiens

<400> SEQUENCE: 14

```
Met Ala Ala Gln Gly Glu Pro Gly Tyr Leu Ala Ala Gln Ser Asp Pro
1               5                   10                  15

Gly Ser Asn Ser Glu Arg Ser Thr Asp Ser Pro Val Pro Gly Ser Glu
            20                  25                  30

Asp Asp Leu Val Ala Gly Ala Thr Leu His Ser Pro Glu Trp Ser Glu
        35                  40                  45

Glu Arg Phe Arg Val Asp Arg Lys Lys Leu Glu Ala Met Leu Gln Ala
    50                  55                  60

Ala Ala Glu Gly Lys Gly Arg Ser Gly Glu Asp Phe Phe Gln Lys Ile
65                  70                  75                  80

Met Glu Glu Thr Asn Thr Gln Ile Ala Trp Pro Ser Lys Leu Lys Ile
                85                  90                  95

Gly Ala Lys Ser Lys Lys Asp Pro His Ile Lys Val Ser Gly Lys Lys
            100                 105                 110

Glu Asp Val Lys Glu Ala Lys Glu Met Ile Met Ser Val Leu Asp Thr
        115                 120                 125

Lys Ser Asn Arg Val Thr Leu Lys Met Asp Val Ser His Thr Glu His
    130                 135                 140

Ser His Val Ile Gly Lys Gly Gly Asn Asn Ile Lys Lys Val Met Glu
145                 150                 155                 160

Glu Thr Gly Cys His Ile His Phe Pro Asp Ser Asn Arg Asn Asn Gln
                165                 170                 175

Ala Glu Lys Ser Asn Gln Val Ser Ile Ala Gly Gln Pro Ala Gly Val
            180                 185                 190
```

-continued

```
Glu Ser Ala Arg Val Arg Ile Arg Glu Leu Leu Pro Leu Val Leu Met
        195                 200                 205

Phe Glu Leu Pro Ile Ala Gly Ile Leu Gln Pro Val Pro Asp Pro Asn
    210                 215                 220

Ser Pro Ser Ile Gln His Ile Ser Gln Thr Tyr Asn Ile Ser Val Ser
225                 230                 235                 240

Phe Lys Gln Arg Ser Arg Met Tyr Gly Ala Thr Val Ile Val Arg Gly
                245                 250                 255

Ser Gln Asn Asn Thr Ser Ala Val Lys Glu Gly Thr Ala Met Leu Leu
            260                 265                 270

Glu His Leu Ala Gly Ser Leu Ala Ser Ala Ile Pro Val Ser Thr Gln
        275                 280                 285

Leu Asp Ile Ala Ala Gln His His Leu Phe Met Met Gly Arg Asn Gly
    290                 295                 300

Ser Asn Ile Lys His Ile Met Gln Arg Thr Gly Ala Gln Ile His Phe
305                 310                 315                 320

Pro Asp Pro Ser Asn Pro Gln Lys Lys Ser Thr Val Tyr Leu Gln Gly
                325                 330                 335

Thr Ile Glu Ser Val Cys Leu Ala Arg Gln Tyr Leu Met Gly Cys Leu
            340                 345                 350

Pro Leu Val Leu Met Phe Asp Met Lys Glu Glu Ile Glu Val Asp Pro
        355                 360                 365

Gln Phe Ile Ala Gln Leu Met Glu Gln Leu Asp Val Phe Ile Ser Ile
    370                 375                 380

Lys Pro Lys Pro Lys Gln Pro Ser Lys Ser Val Ile Val Lys Ser Val
385                 390                 395                 400

Glu Arg Asn Ala Leu Asn Met Tyr Glu Ala Arg Lys Cys Leu Leu Gly
                405                 410                 415

Leu Glu Ser Ser Gly Val Thr Ile Ala Thr Ser Pro Ser Pro Ala Ser
            420                 425                 430

Cys Pro Ala Gly Leu Ala Cys Pro Ser Leu Asp Ile Leu Ala Ser Ala
        435                 440                 445

Gly Leu Gly Leu Thr Gly Leu Gly Leu Leu Gly Pro Thr Thr Leu Ser
    450                 455                 460

Leu Asn Thr Ser Thr Thr Pro Asn Ser Leu Leu Asn Ala Leu Asn Ser
465                 470                 475                 480

Ser Val Ser Pro Leu Gln Ser Pro Ser Ser Gly Thr Pro Ser Pro Thr
                485                 490                 495

Leu Trp Ala Pro Pro Leu Ala Asn Thr Ser Ser Ala Thr Gly Phe Ser
            500                 505                 510

Ala Ile Pro His Leu Met Ile Pro Ser Thr Ala Gln Ala Thr Leu Thr
        515                 520                 525

Asn Ile Leu Leu Ser Gly Val Pro Thr Tyr Gly His Thr Ala Pro Ser
    530                 535                 540

Pro Pro Pro Gly Leu Thr Pro Val Asp Val His Ile Asn Ser Met Gln
545                 550                 555                 560

Thr Glu Gly Lys Lys Ile Ser Ala Ala Leu Asn Gly His Ala Gln Ser
                565                 570                 575

Pro Asp Ile Lys Tyr Gly Ala Ile Ser Thr Ser Ser Leu Gly Glu Lys
            580                 585                 590

Val Leu Ser Ala Asn His Gly Asp Pro Ser Ile Gln Thr Ser Gly Ser
        595                 600                 605

Glu Gln Thr Ser Pro Lys Ser Ser Pro Thr Glu Gly Cys Asn Asp Ala
```

-continued

```
    610                 615                 620

Phe Val Glu Val Gly Met Pro Arg Ser Pro Ser His Ser Gly Asn Ala
625                 630                 635                 640

Gly Asp Leu Lys Gln Met Met Cys Pro Ser Lys Val Ser Cys Ala Lys
                645                 650                 655

Arg Gln Thr Val Glu Leu Leu Gln Gly Thr Lys Asn Ser His Leu His
            660                 665                 670

Ser Thr Asp Arg Leu Leu Ser Asp Pro Glu Leu Ser Ala Thr Glu Ser
        675                 680                 685

Pro Leu Ala Asp Lys Lys Ala Pro Gly Ser Glu Arg Ala Ala Glu Arg
    690                 695                 700

Ala Ala Ala Ala Gln Gln Asn Ser Glu Arg Ala His Leu Ala Pro Arg
705                 710                 715                 720

Ser Ser Tyr Val Asn Met Gln Ala Phe Asp Tyr Glu Gln Lys Lys Leu
                725                 730                 735

Leu Ala Thr Lys Ala Met Leu Lys Lys Pro Val Val Thr Glu Val Arg
            740                 745                 750

Thr Pro Thr Asn Thr Trp Ser Gly Leu Gly Phe Ser Lys Ser Met Pro
        755                 760                 765

Ala Glu Thr Ile Lys Glu Leu Arg Arg Ala Asn His Val Ser Tyr Lys
    770                 775                 780

Pro Thr Met Thr Thr Thr Tyr Glu Gly Ser Ser Met Ser Leu Ser Arg
785                 790                 795                 800

Ser Asn Ser Arg Glu His Leu Gly Gly Gly Ser Glu Ser Asp Asn Trp
                805                 810                 815

Arg Asp Arg Asn Gly Ile Gly Pro Gly Ser His Ser Glu Phe Ala Ala
            820                 825                 830

Ser Ile Gly Ser Pro Lys Arg Lys Gln Asn Lys Ser Thr Glu His Tyr
        835                 840                 845

Leu Ser Ser Ser Asn Tyr Met Asp Cys Ile Ser Ser Leu Thr Gly Ser
    850                 855                 860

Asn Gly Cys Asn Leu Asn Ser Ser Phe Lys Gly Ser Asp Leu Pro Glu
865                 870                 875                 880

Leu Phe Ser Lys Leu Gly Leu Gly Lys Tyr Thr Asp Val Phe Gln Gln
                885                 890                 895

Gln Glu Ile Asp Leu Gln Thr Phe Leu Thr Leu Thr Asp Gln Asp Leu
            900                 905                 910

Lys Glu Leu Gly Ile Thr Thr Phe Gly Ala Arg Arg Lys Met Leu Leu
        915                 920                 925

Ala Ile Ser Glu Leu Asn Lys Asn Arg Arg Lys Leu Phe Glu Ser Pro
    930                 935                 940

Asn Ala Arg Thr Ser Phe Leu Glu Gly Gly Ala Ser Gly Arg Leu Pro
945                 950                 955                 960

Arg Gln Tyr His Ser Asp Ile Ala Ser Val Ser Gly Arg Trp
                965                 970
```